United States Patent
Fujita et al.

(10) Patent No.: US 7,842,700 B2
(45) Date of Patent: Nov. 30, 2010

(54) CRYSTALS OF ISOPROPYL ESTER OF N-(2,6-DICHLOROBENZOYL)-4-[6-(METHYLAMINO)METHYL-1-METHYL-2,4-DIOXO-1,4-DIHYDROQUINAZOLINE-3(2H)-YL]-L-PHENYLALANINE HYDROCHLORIDE, PRODUCTION METHOD THEREOF AND USE THEREOF

(75) Inventors: Koichi Fujita, Kawasaki (JP);
Shinichiro Takahashi, Kawasaki (JP);
Tatsuya Okuzumi, Kawasaki (JP);
Tatsuhiro Yamada, Kawasaki (JP);
Kotaro Okado, Kawasaki (JP);
Noriyasu Kataoka, Kawasaki (JP);
Haruko Hirashima, Kawasaki (JP);
Hideyuki Yamaguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/963,192

(22) Filed: Dec. 21, 2007

(65) Prior Publication Data
US 2008/0108637 A1 May 8, 2008

Related U.S. Application Data

(63) Continuation of application No. PCT/JP2006/312432, filed on Jun. 21, 2006.

(30) Foreign Application Priority Data
Jun. 21, 2005 (JP) ............................. 2005-181219

(51) Int. Cl.
*A61K 31/517* (2006.01)
(52) U.S. Cl. .................................. 514/266.3; 544/285
(58) Field of Classification Search .............. 514/266.3; 544/285
See application file for complete search history.

(56) References Cited

U.S. PATENT DOCUMENTS 7,153,963 B2   12/2006   Makino et al.

2005/0222141 A1   10/2005   Sagi et al.
2006/0009476 A1   1/2006   Kataoka et al.
2006/0223836 A1   10/2006   Makino et al.
2007/0018172 A1   1/2007   Takahashi et al.

FOREIGN PATENT DOCUMENTS

| WO | WO 02/16329 | 2/2002 |
|----|----|----|
| WO | WO 03/070709 | 8/2003 |
| WO | WO 2004/074264 | 9/2004 |
| WO | WO 2005/051925 | 6/2005 |
| WO | WO 2005/061466 | 7/2005 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Chawla, et al. Curr. Res. & Info. Pharm. Sci. (CRIPS), 5, 1, 2004, 9-12.*
Hackam, et al. JAMA, 296(14), 2006, 1731-1732.*
Edited by CSJ: The Chemical Society of Japan, "4th edition, Jikken Kagaku Koza 1, Kihon Sosa 1", pp. 184 to 186, Heisei 2 Nen 11 Gatsu 5 Nichi published, Maruzen Co., Ltd., 1990.
"The Chemical Society of Japan, ed. *Dai-4-han Jikken Kagaku Kouza 1* (the Fourth Series of Experimental Chemistry Guide Book 1) Basic Operations I, p. 184-186, Nov. 5, 1990, Maruzen, Co., Ltd." ( Submitting English abstract only, reference previously filed Dec. 21, 2007).
U.S. Appl. No. 11/963,144, filed Dec. 21, 2007, Sagi, et al.
U.S. Appl. No. 12/470,846, filed May 22, 2009, Kataoka, et al.
U.S. Appl. No. 12/697,816, filed Feb. 1, 2010, Takahashi, et al.

* cited by examiner

*Primary Examiner*—James O Wilson
*Assistant Examiner*—Douglas M Willis
(74) *Attorney, Agent, or Firm*—Oblon, Spivak, McClelland, Maier & Neustadt, L.L.P.

(57) ABSTRACT

Crystals of isopropyl ester of N-(2,6-dichlorobenzoyl)-4-[6-(methylamino)methyl-1-methyl-2,4-dioxo-1,4-dihydroquinazoline-3(2H)-yl]-L-phenylalanine hydrochloride are useful as α4 integrin inhibitors.

15 Claims, 55 Drawing Sheets

CRYSTALS OF ISOPROPYL ESTER OF N-(2,6-DICHLOROBENZOYL)-4-[6-(METHYLAMINO)METHYL-1-METHYL-2,4-DIOXO-1,4-DIHYDROQUINAZOLINE-3(2H)-YL]-L-PHENYLALANINE HYDROCHLORIDE, PRODUCTION METHOD THEREOF AND USE THEREOF

CROSS REFERENCES TO RELATED APPLICATIONS

This application is a continuation of International Patent Application No. PCT/JP2006/312432, filed on Jun. 21, 2006, and claims priority to Japanese Patent Application No. 2005-181219, filed on Jun. 21, 2005.

BACKGROUND OF THE INVENTION

1. Field of the Invention

The present invention relates to crystals of phenylalanine derivatives which have a specific structural formula, production method thereof and use thereof, and particularly the use thereof as an active ingredient of pharmaceutical compositions.

2. Discussion of the Background

It is already known that phenylalanine derivatives have α4 integrin inhibiting action and they are useful compounds as therapeutic agents for inflammatory bowel diseases or the like (Patent Literatures 1 and 2).

In response, the inventors have found that specific novel phenylalanine derivatives which are not specifically described in the above patent literatures have particularly high α4 integrin inhibiting activity under the existence of serum; the total clearance thereof is low; the area under the plasma concentration-time curve and bioavailability thereof are high in oral administration; and α4 integrin inhibiting activity thereof in vivo is also high in oral administration. The PCT application was filed (PCT/JP2004/019704) based on these findings.

A compound of the following formula (I) (hereinafter also referred to as a compound (I)) disclosed in Example 151 of the above PCT application or pharmaceutically acceptable salts thereof is a prodrug of a compound of the following formula (II) disclosed in Example 99 of the PCT application. The compound of the formula (II) which is the active compound has extremely excellent α4 integrin inhibiting activity, and the total clearance thereof is low (which means that it is excellent in retention in plasma). Thus, it is the compound valuable in the actual use. However, the compound of the following formula (I) disclosed in Example 151 of the PCT application is obtained by the method comprising the steps of: stirring a mixture of a corresponding carboxylic acid, corresponding alcohol and a 4M hydrogen chloride dioxane solution at 90° C. for several hours; removing the solvent and purifying the obtained crude material with high-performance liquid chromatography (water/acetonitrile, each containing 0.1% TFA); and then collecting the compound by freeze-drying (which is the method in accordance with Method C of Examples 101 to 121 or Process 3 of Example 53). Namely, the obtained compound was an inferior crystalline form of trifluoroacetate salt.

In general, when preserving a drug substance, or manufacturing or preserving a preparation, drug substances inferior in crystallinity such as amorphia and noncrystalline solid substances are physically and chemically unstable against environmental conditions such as temperature, humidity and air, and they are highly hygroscopic. Therefore, such drug substances tend to have problems upon developing pharmaceutical compositions wherein the high purity of the substance is required, and they also tend to be accompanied by difficulties upon manufacturing on the industrial scale.

Further, in general, since drug substances inferior in crystallinity such as amorphia and noncrystalline solid substances have the degradability by moisture absorption, solvents which can be used upon manufacturing a preparation are limited to anhydrides, and, therefore, it may cause the increase in preparation cost.

Patent Literature 1: WO 02/16329

Patent Literature 2: WO03/070709

Patent Literature 3: WO2004/074264

BRIEF SUMMARY OF THE INVENTION

The object of the present invention is to provide a compound (I) or salts thereof in a crystalline form excellent in usability.

The further object of the present invention is to provide a crystal excellent in preservation stability, humidity resistance or solubility as the compound (I) or salts thereof.

The additional object of the present invention is to provide a crystal which can be manufactured on the industrial scale as the compound (I).

The inventors thoroughly searched to solve the above problems and examined crystalline forms of the compound (I) or pharmaceutically acceptable salts thereof. As a result, they found that various crystalline forms are produced by heating the compound in a specific solvent(s) and then cooling it down to the specific temperature; and that the above problems can be solved by using such crystals. The present invention has been completed based on this finding.

Namely, the present invention is as follows.

(1) A crystal of a compound of the formula (I) or salts thereof.

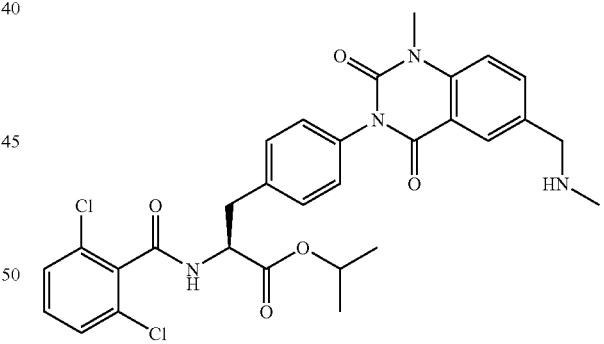

(I)

(2) The crystal according to (1), wherein the crystal of the compound of the formula (I) is either crystal form A, crystal form B, crystal form D, crystal form E or crystal form F, each of which shows the peak at the following diffraction angles (2θ) in the powder X-ray diffraction pattern.

| A | B | D | E | F |
|---|---|---|---|---|
| 8.5 | 9.7 | 4.4 | 5.9 | 5.5 |
| 10.4 | 11.4 | 5.2 | 14.3 | 8.0 |
| 15.4 | 14.5 | 9.2 | 20.1 | 18.2 |

-continued

| A | B | D | E | F |
|---|---|---|---|---|
| 16.9 | 20.0 | 20.6 | 23.0 | 19.4 |
| 23.5 | 23.8 | | | 21.9 |

(3) The crystal according to (1), wherein the crystal of a hydrochloride salt of the compound of the formula (I) is either crystal form Cl1, crystal form Cl2, crystal form Cl3, crystal form Cl4 or crystal form Cl5, each of which shows the peak at the following diffraction angles (2θ) in the powder X-ray diffraction pattern.

| Cl1 | Cl2 | Cl3 | Cl4 | Cl5 |
|---|---|---|---|---|
| 2.9 | 8.5 | 3.6 | 4.9 | 8.2 |
| 7.7 | 10.5 | 8.9 | 17.5 | 11.2 |
| 11.6 | 16.0 | 12.4 | | 12.4 |
| 20.3 | 17.0 | | | 14.3 |
| | 23.6 | | | 15.6 |

(4) The crystal according to (1), wherein the crystal of a hydrochloride salt of the compound of the formula (I) is either crystal form NW1, crystal form NW2, crystal form NW4, crystal form NW5, crystal form N1, crystal form N2, crystal form N3, crystal form N4, crystal form N5, crystal form Cl6, crystal form Cl7 or crystal form Cl8, each of which shows the peak at the following diffraction angles (2θ) in the powder X-ray diffraction pattern.

| NW1 | NW2 | NW4 | NW5 | N1 | N2 | N3 | N4 | N5 | Cl6 | Cl7 | Cl8 |
|---|---|---|---|---|---|---|---|---|---|---|---|
| 9.1 | 8.6 | 5.8 | 9.2 | 6.0 | 6.4 | 8.4 | 5.5 | 5.4 | 8.7 | 8.5 | 8.9 |
| 12.6 | 10.4 | 7.6 | 11.2 | 6.7 | 8.5 | 9.2 | 8.3 | 10.7 | 12.1 | 11.9 | 12.5 |
| 13.0 | 12.0 | 8.7 | 15.0 | 12.4 | 9.3 | 14.7 | 11.3 | 17.1 | 17.8 | 14.0 | 17.8 |
| 13.6 | 12.4 | 10.4 | 19.9 | 13.4 | 12.9 | 15.2 | 13.7 | 19.0 | 19.3 | 17.9 | |
| 24.1 | 13.0 | 22.5 | 22.4 | 13.5 | 14.8 | | 17.5 | | 25.5 | 19.4 | |
| | 15.0 | | 24.9 | 13.9 | 15.3 | | 19.2 | | | | |
| | 15.5 | | 25.6 | | | | | | | | |
| | 24.2 | | 25.9 | | | | | | | | |

(5) The crystal according to (1), wherein the crystal of a sulfate salt of the compound of the formula (I) is either crystal form Su1, crystal form Su2 or crystal form Su3, each of which shows the peak at the following diffraction angles (2θ) in the powder X-ray diffraction pattern.

| Su1 | Su2 | Su3 |
|---|---|---|
| 3.8 | 2.3 | 4.7 |
| 7.7 | 12.6 | 9.1 |
| 11.4 | 18.2 | |
| 13.3 | 23.1 | |
| 22.6 | | |

(6) The crystal according to (1), wherein the crystal of a hydrobromide salt of the compound of the formula (I) is either crystal form Br1, crystal form Br2, crystal form Br3, crystal form Br4 or crystal form Br5, each of which shows the peak at the following diffraction angles (2θ) in the powder X-ray diffraction pattern.

| Br1 | Br2 | Br3 | Br4 | Br5 |
|---|---|---|---|---|
| 5.7 | 3.6 | 8.4 | 7.7 | 5.0 |
| 10.1 | 4.4 | 11.5 | 10.1 | 9.5 |
| | 8.9 | 17.2 | 16.4 | 12.2 |
| | | | 20.1 | 13.4 |
| | | | | 14.2 |
| | | | | 14.9 |

(7) The crystal according to (1), wherein the crystal of a phosphate salt of the compound of the formula (I) is either crystal form Pho1, crystal form Pho2, crystal form Pho3 or crystal form Pho4, each of which shows the peak at the following diffraction angles (2θ) in the powder X-ray diffraction pattern.

| Pho1 | Pho2 | Pho3 | Pho4 |
|---|---|---|---|
| 2.5 | 4.3 | 3.5 | 4.1 |
| 11.9 | 6.9 | 5.1 | 6.4 |
| 17.2 | 10.1 | 6.9 | 7.6 |
| 18.3 | 16.9 | 14.0 | 11.5 |
| | | | 12.1 |
| | | | 12.7 |

(8) The crystal according to (1), wherein the crystal of a maleate salt of the compound of the formula (I) is either crystal form Mal1, crystal form Mal2 or crystal form Mal3, each of which shows the peak at the following diffraction angles (2θ) in the powder X-ray diffraction pattern.

| Mal1 | Mal2 | Mal3 |
|---|---|---|
| 3.7 | 2.8 | 8.2 |
| 7.7 | 4.8 | 10.8 |
| 8.5 | 7.3 | |
| 9.4 | 13.8 | |
| | 14.6 | |
| | 15.3 | |

(9) The crystal according to (1), wherein the crystal of an acetate salt of the compound of the formula (I) is either crystal form Aca1, crystal form Aca2 or crystal form Aca3, each of which shows the peak at the following diffraction angles (2θ) in the powder X-ray diffraction pattern.

| Aca1 | Aca2 | Aca3 |
|---|---|---|
| 5.7 | 3.8 | 4.9 |
| 8.1 | 4.7 | 18.5 |
| 8.5 | 9.2 | 19.3 |
| 11.3 | 12.4 | |
| 17.7 | | |
| 18.3 | | |
| 19.1 | | |

(10) The crystal according to (1), wherein the crystal of a D-tartrate salt of the compound of the formula (I) is either crystal form Tar1 or crystal form Tar2, each of which shows the peak at the following diffraction angles (2θ) in the powder X-ray diffraction pattern.

| Tar1 | Tar2 |
|---|---|
| 2.4 | 4.0 |
| 8.5 | 8.0 |
| 14.5 | 9.3 |
| 16.6 | 11.0 |
| 18.5 | 17.9 |

(11) The crystal according to (1), wherein the crystal of an L-tartrate salt of the compound of the formula (I) is either crystal form L-Tar1 or crystal form L-Tar2, each of which shows the peak at the following diffraction angles (2θ) in the powder X-ray diffraction pattern.

| L-Tar1 | L-Tar2 |
|---|---|
| 7.1 | 7.2 |
| 8.9 | 9.5 |
| 11.8 | 16.8 |
| 12.9 | 18.3 |

(12) The crystal according to (1), wherein the crystal of a methanesulfonate salt of the compound of the formula (I) is either crystal form Ms1, crystal form Ms2, crystal form Ms3, crystal form Ms4 or crystal form Ms5, each of which shows the peak at the following diffraction angles (2θ) in the powder X-ray diffraction pattern.

| Ms1 | Ms2 | Ms3 | Ms4 | Ms5 |
|---|---|---|---|---|
| 13.3 | 9.8 | 9.5 | 9.4 | 8.1 |
| 19.2 | 15.7 | 13.9 | 13.1 | 9.4 |
| 22.9 | 17.5 | 16.9 | 23.4 | 13.2 |
| 25.7 | 18.0 | | 23.9 | 17.5 |
| | 18.4 | | | |

(13) The crystal according to (1), wherein the crystal of a citrate salt of the compound of the formula (I) is either crystal form Ca1, crystal form Ca2, crystal form Ca3 or crystal form Ca4, each of which shows the peak at the following diffraction angles (2θ) in the powder X-ray diffraction pattern.

| Ca1 | Ca2 | Ca3 | Ca4 |
|---|---|---|---|
| 6.7 | 8.3 | 6.8 | 9.5 |
| 17.3 | 11.8 | 16.2 | 12.9 |
| 17.9 | 17.2 | 20.5 | 18.1 |
| 20.6 | | 22.7 | 19.9 |
| 26.0 | | | |

(14) The crystal according to (1) which shows the peak at the diffraction angles (2θ) of 8.2, 11.2, 14.3 and 15.6 in the powder X-ray diffraction pattern.

(15) The crystal according to (1) which has a 13C-NMR spectrum of FIG. 20.

(16) The crystal according to (1) which has an infrared spectrum of FIG. 21.

(17) The crystal according to any one of (14) to (16), which is a crystal of a hydrochloride salt of the compound of the formula (I).

(18) The crystal according to (1) which shows the peak at the diffraction angles (2θ) of 6.4, 9.3, 12.9 and 15.3 in the powder X-ray diffraction pattern.

(19) The crystal according to (1) which has a 13C-NMR spectrum of FIG. 28.

(20) The crystal according to (1) which has an infrared spectrum of FIG. 29.

(21) The crystal according to any one of (18) to (20), which is a crystal of a hydrochloride salt of the compound of the formula (I).

(22) A production method of the crystal according to (2), which comprises the steps of: heating the compound of the formula (I) in a solvent selected from the group consisting of methanol, ethanol, propanol, butanol, amyl alcohol, dimethylformamide, dimethyl sulfoxide, dichloromethane, diethyl ether and pyridine; and then cooling it down to 0 to 30° C.

(23) A production method of the crystal according to (3) or (4), which comprises the steps of: heating the hydrochloride salt of the compound of the formula (I) in a solvent selected from the group consisting of methanol, ethanol, propanol, butanol, acetone, diethyl ether, nitromethane, 1,2-dimethoxyethane, isopropyl acetate, ethyl acetate, acetonitrile, tetrahydrofuran, 4-trifluoromethyl toluene and pyridine; and then cooling it down to 0 to 30° C.

(24) A production method of the crystal according to (5), which comprises the steps of: heating the sulfate salt of the compound of the formula (I) in a solvent selected from the group consisting of methanol, ethanol, 1,2-ethanediol, acetone, nitromethane, ethyl acetate, 1,2-dimethoxyethane, diethyl ether, dichloromethane, cyclohexanone, n-heptane, tetrahydrofuran and pyridine; and then cooling it down to 0 to 30° C.

(25) A production method of the crystal according to (6), which comprises the steps of: heating the hydrobromide salt of the compound of the formula (I) in a solvent selected from the group consisting of water, ethanol, propanol, butanol, acetone, diisopropyl ether, acetonitrile, ethyl acetate, 1,2-dimethoxyethane, cyclohexanone and tetrahydrofuran; and then cooling it down to 0 to 30° C.

(26) A production method of the crystal according to (7), which comprises the steps of: heating the phosphate salt of the compound of the formula (I) in a solvent selected from the group consisting of water, methanol, propanol, acetone, diisopropyl ether, diethyl ether, acetonitrile, ethyl acetate, isopropyl acetate, 1,2-dimethoxyethane, 1,1,2,2-tetrachloroethane, nitromethane, dichloromethane, 2,2,2-trifluoroethanol, N,N-dimethylacetamide, cyclohexanone, n-heptane, tetrahydrofuran and pyridine; and then cooling it down to 0 to 30° C.

(27) A production method of the crystal according to (8), which comprises the steps of: heating the maleate salt of the compound of the formula (I) in a solvent selected from the group consisting of ethanol, propanol, butanol, acetone, acetonitrile, ethyl acetate, isopropyl acetate, 1,2-dimethoxyethane and nitromethane; and then cooling it down to 0 to 30° C.

(28) A production method of the crystal according to (9), which comprises the steps of: heating the acetate salt of the compound of the formula (I) in a solvent selected from the group consisting of propanol, butanol, acetone, acetonitrile, ethyl acetate, isopropyl acetate and nitromethane; and then cooling it down to 0 to 30° C.

(29) A production method of the crystal according to (10), which comprises the steps of: heating the D-tartrate salt of the compound of the formula (I) in a solvent selected from the group consisting of methanol, acetone, 1,2-dimethoxyethane, nitromethane and cyclohexanone; and then cooling it down to 0 to 30° C.

(30) A production method of the crystal according to (11), which comprises the steps of: heating the L-tartrate salt of the compound of the formula (I) in a solvent selected from the group consisting of acetone and 1,2-dimethoxyethane; and then cooling it down to 0 to 30° C.

(31) A production method of the crystal according to (12), which comprises the steps of: heating the methanesulfonate salt of the compound of the formula (I) in a solvent selected from the group consisting of methanol, acetone, 1,2-dimethoxyethane, tetrahydrofuran and tert-butyl methyl ether; and then cooling it down to 0 to 30° C.

(32) A production method of the crystal according to (13), which comprises the steps of: heating the citrate salt of the compound of the formula (I) in a solvent selected from the group consisting of acetone, 1,2-dimethoxyethane, butanol and propanol; and then cooling it down to 0 to 30° C.

(33) A production method of the crystal according to any one of (14) to (17), which comprises the step of adding a hydrogen chloride to a mixture comprising the compound of the formula (I) and acetone.

(34) A production method of the crystal according to any one of (14) to (17), which comprises the steps of: heating the hydrochloride salt of the compound of the formula (I) in a solvent comprising acetone and water; adding an acetone solvent thereto; and then cooling it down.

(35) A production method of the crystal according to any one of (14) to (17), which comprises the step of: mixing the hydrochloride salt of the compound of the formula (I) and two or more solvents selected from the group consisting of acetone, water, tetrahydrofuran, acetonitrile, methanol, ethanol, propanol and isopropyl acetate to obtain a suspension thereof.

(36) A production method of the crystal according to any one of (18) to (21), which comprises the steps of: heating the hydrochloride salt of the compound of the formula (I) in a solvent comprising acetonitrile and water; adding an acetone solvent thereto; and then cooling it down.

(37) A pharmaceutical composition which contains the crystal according to any one of (1) to (21).

(38) An α4 integrin inhibitor which contains the crystal according to any one of (1) to (21).

(39) A therapeutic agent or preventive agent for inflammatory diseases in which α4 integrin-depending adhesion process participates in the pathology, which contains the crystal according to any one of (1) to (21) as an active ingredient.

(40) A therapeutic agent or preventive agent for either rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis or transplantation rejection, which contains the crystal according to any one of (1) to (21) as an active ingredient.

(41) A hydrochloride salt of the compound of the formula (I), hydrobromide thereof or maleate thereof.

DETAILED DESCRIPTION OF THE PREFERRED EMBODIMENTS

Figure 1:
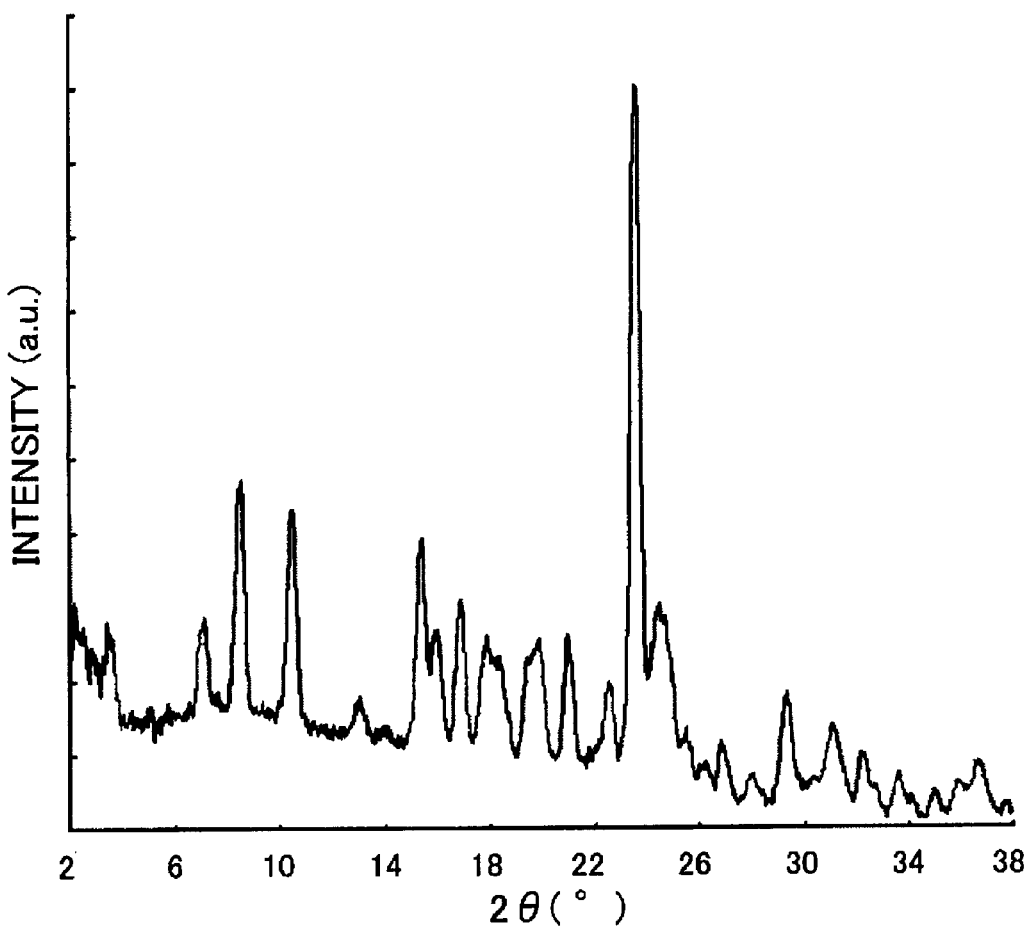
FIG. 1 shows a powder X-ray diffraction pattern of crystal form A of the compound (free form) of the formula (I) of the present invention.

The compound of the above formula (I) in the present invention is a prodrug of an active form of the following formula (II).

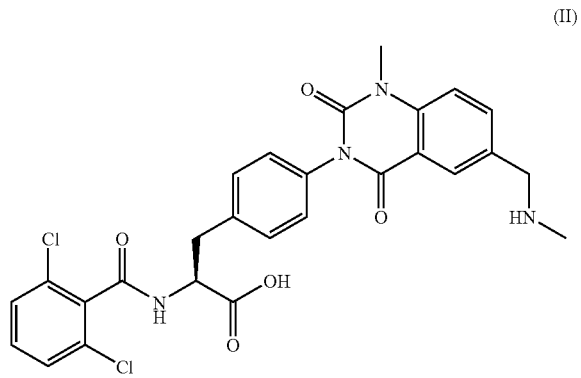

In the crystal of (1), salts of the compound of the formula (I) are preferably a hydrochloride salt, hydrobromide salt and maleate salt, and a hydrochloride salt is particularly preferable.

The crystal of the compound of the above formula (I) may be crystals of the free form, or a hydrate or solvate thereof. Examples of these crystals are crystal form A, crystal form B, crystal form D, crystal form E and crystal form F as mentioned in above (2), each of which shows the peak at the specific diffraction angles (2θ) in the powder X-ray diffraction pattern.

Among them, crystal form A can be obtained by the method comprising the steps of: heating the compound of the formula (I) preferably at 50 to 80° C. and more preferably at 60° C., preferably in dimethylformamide or pyridine, and more preferably in pyridine; quickly cooling it down (for example, at a cooling rate of 20 to 40° C./hour and preferably 30° C./hour) to 2 to 20° C. and preferably to 5° C.; aging the compound at the same temperature for about 24 hours; and collecting the precipitated crystal. The crystal obtained as above is usually in the form of hydrates.

Crystal form B can be obtained by the method comprising the steps of: heating the compound of the formula (I) preferably at 50 to 80° C. and more preferably at 60° C., preferably in 1-butanol, t-butanol, 2-butanol, 1-propanol, 2-propanol, ethanol, diethyl ether or dimethyl sulfoxide, and more preferably in 1-butanol, t-butanol or ethanol; quickly (for example, at a cooling rate of 20 to 40° C./hour and preferably 30° C./hour) or slowly (at a cooling rate of 0.5 to 3° C./hour and preferably 1° C./hour) cooling it down to 2 to 20° C. and preferably to 5° C.; aging the compound at the same temperature for about 24 hours; and collecting the precipitated crystal.

Crystal form D can be obtained by the method comprising the steps of: heating the compound of the formula (I) preferably at 50 to 80° C. and more preferably at 60° C., preferably in ethanol; quickly (for example, at a cooling rate of 20 to 40° C./hour and preferably 30° C./hour) or slowly (at a cooling rate of 0.5 to 3° C./hour and preferably 1° C./hour) cooling it down to 2 to 20° C. and preferably to 5° C.; aging the compound at the same temperature for about 24 hours; and collecting the precipitated crystal.

Crystal form E can be obtained by the method comprising the steps of: heating the compound of the formula (I) preferably at 50 to 80° C. and more preferably at 60° C., preferably in ethanol, dichloromethane or diethyl ether, and more preferably in ethanol; then, slowly (at a cooling rate of 0.5 to 3° C./hour and preferably 1° C./hour) cooling it down to 2 to 20° C. and preferably to 5° C.; aging the compound at the same temperature for about 24 hours; and collecting the precipitated crystal. The crystal obtained as above is usually in the form of anhydrides.

Crystal form F can be obtained by the method comprising the steps of: heating the compound of the formula (I) preferably at 50 to 80° C. and more preferably at 60° C., preferably in t-amyl alcohol; then, slowly (at a cooling rate of 0.5 to 3° C./hour and preferably 1° C./hour) cooling it down to 2 to 20° C. and preferably to 5° C.; aging the compound at the same temperature for about 24 hours; and collecting the precipitated crystal.

The crystal of the hydrochloride salt of the compound of the formula (I) is either crystal form Cl1, crystal form Cl2, crystal form Cl3, crystal form Cl4 or crystal form Cl5, each of which shows the peak at the specific diffraction angles (2θ) in the powder X-ray diffraction pattern as mentioned in above (3). Further, the crystal of the hydrochloride salt of the compound of the formula (I) is either crystal form NW1, crystal form NW2, crystal form NW4, crystal form NW5, crystal form N1, crystal form N2, crystal form N3, crystal form N4, crystal form N5, crystal form Cl6, crystal form Cl7 or crystal form Cl8, each of which shows the peak at the specific diffraction angles (2θ) in the powder X-ray diffraction pattern as mentioned in above (4). Crystal form Cl5 is also specified by the peak at the specific diffraction angles (2θ) in the powder X-ray diffraction pattern of above (14), the 13C-NMR spectrum of FIG. 20, and/or the infrared spectrum of FIG. 21 as mentioned in above (14) to (17). Further, crystal form N2 is also specified by the peak at the specific diffraction angles (2θ) in the powder X-ray diffraction pattern of above (18), the 13C-NMR spectrum of FIG. 28, and/or the infrared spectrum of FIG. 29 as mentioned in above (18) to (21).

Among them, crystal form Cl1 can be obtained by the method comprising the steps of: heating the hydrochloride salt of the compound of the formula (I) preferably at 50 to 80° C. and more preferably at 60° C., preferably in 4-trifluoromethyl toluene, pyridine or acetone and more preferably in pyridine; then, slowly (at a cooling rate of 0.5 to 3° C./hour and preferably 1° C./hour) cooling it down to 2 to 20° C. and preferably to 5° C.; aging the compound at the same temperature for about 1 hour or 72 hours; and collecting the precipitated crystal.

Crystal form Cl2 can be obtained by the method comprising the steps of: heating the hydrochloride salt of the compound of the formula (I) preferably at 50 to 80° C. and more preferably at 60° C., preferably in nitromethane or diethyl ether and more preferably in nitromethane; then, slowly (at a cooling rate of 0.5 to 3° C./hour and preferably 1° C./hour) cooling it down to 2 to 20° C. and preferably to 5° C.; aging the compound at the same temperature for about 1 hour or 72 hours; and collecting the precipitated crystal.

Crystal form Cl3 can be obtained by the method comprising the steps of: heating the hydrochloride salt of the compound of the formula (I) preferably at 50 to 80° C. and more preferably at 60° C., preferably in 2-butanol or 1,2-dimethoxyethane and more preferably in 2-butanol; then, slowly (at a cooling rate of 0.5 to 3° C./hour and preferably 1°

C./hour) cooling it down to 2 to 20° C. and preferably to 5° C.; aging the compound at the same temperature for about 1 hour or 72 hours; and collecting the precipitated crystal.

Crystal form Cl4 can be obtained by the method comprising the steps of: heating the hydrochloride salt of the compound of the formula (I) preferably at 50 to 80° C. and more preferably at 60° C., preferably in isopropyl acetate or methanol; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. In the case of using 2-propanol, acetonitrile, ethanol or ethyl acetate and preferably 2-propanol as a solvent, crystal form Cl4 can be obtained by the same method as mentioned above provided that the aging time becomes about 72 hours.

Crystal form Cl5 can be obtained by the method comprising the steps of: heating the hydrochloride salt of the compound of the formula (I) preferably at 50 to 80° C. and more preferably at 60° C., preferably in tetrahydrofuran (THF); then, at a cooling rate of 0.5 to 10° C./hour and preferably slowly (at a cooling rate of 0.5 to 3° C./hour and preferably 1° C./hour) cooling it down to 2 to 20° C. and preferably to 5° C.; aging the compound at the same temperature for about 1 hour or 72 hours; and collecting the precipitated crystal.

Crystal form Cl5 is a particularly preferable crystal.

Crystal form Cl5 can also be obtained by the production method comprising the step of adding a hydrogen chloride to a mixture comprising the compound of the formula (I) and acetone. In the case of adding the hydrogen chloride, it is possible to use hydrogen chloride gas, a hydrochloric acid or alcohols having 1 to 6 carbon atom(s) which comprise hydrogen chloride, for example.

More specifically, crystal form Cl5 can be obtained by the method comprising the steps of: preparing a hydrochloric acid by diluting it with acetone to become 0.05 to 1.00 mmol/mL in hydrogen chloride concentration; adding it to an acetone solution of the compound (free form) of the formula (I); heating the mixture with stirring preferably to 50 to 80° C. and more preferably to 60° C.; then, comparatively slowly (at a cooling rate of 0.5 to 10° C./hour) cooling it down to 2 to 20° C. and preferably to 5° C.; aging the compound at the same temperature for about 1 to 72 hour(s); and filtering out the precipitated crystal and drying it at 60 to 85° C. under reduced pressure.

Crystal form Cl5 can also be obtained by the production method comprising the steps of: heating the hydrochloride salt of the compound of the formula (I) in a mixed solvent comprising acetone and water; adding an acetone solvent thereto; and then cooling it down.

More specifically, crystal form Cl5 can be obtained by the method comprising the steps of: heating a mixture of a mixed solvent comprising acetone and water and the hydrochloride salt of the compound of the formula (I) preferably to 50 to 80° C. and more preferably to 65° C. to dissolve the compound; filtering the dissolved solution under heating; adding acetone dropwise to a filtrate and also adding a seed crystal thereto if necessary; then cooling down the obtained slurry to 2 to 20° C. and preferably to 10° C.; and filtering out the precipitated crystal and drying it at 60 to 85° C. and preferably at 80° C. under reduced pressure.

Crystal form Cl5 can also be obtained by the production method comprising the step of: mixing the hydrochloride salt of the compound of the formula (I) and two or more solvents selected from the group consisting of acetone, water, THF, acetonitrile, methanol, ethanol, propanol and isopropyl acetate to obtain a suspension thereof.

More specifically, crystal form Cl5 can be obtained by the method comprising the steps of: suspending the hydrochloride salt of the compound of the formula (I) other than crystal form Cl5 to acetone; stirring the suspension at 10 to 55° C. and preferably at 25° C.; and filtering out the precipitated crystal and drying it at 60 to 85° C. and preferably at 80° C. under reduced pressure.

Crystal form NW1, crystal form NW2 and crystal form NW5 can be obtained, for example, by the method comprising the steps of: mixing the hydrochloride salt of the compound of the formula (I) and a mixed solution of acetonitrile/water and then cooling down the mixture, or heating the mixture and then cooling it down; adding acetonitrile or acetone dropwise thereto; and separating the precipitated crystal from the slurry. In this method, each of crystal form NW1, crystal form NW2 and crystal form NW5 can be obtained by adjusting a quantitative ratio of the hydrochloride salt of the compound of the formula (I) and a mixed solution of acetonitrile/water, the subsequent cooling or heating temperature, or the kind of a solvent added dropwise.

Crystal form N1 can be obtained by drying crystal form NW1 under reduced pressure. Crystal form N2 can be obtained by drying crystal form NW2 under reduced pressure. Meanwhile, crystal form N3 can be obtained by drying crystal form NW2 under reduced pressure, depending on the condition of the solvent adhesion to crystal form NW2. Crystal form N5 can be obtained by drying crystal form NW5 under reduced pressure.

Crystal form N2 can also be obtained by the production method comprising the steps of: heating the hydrochloride salt of the compound of the formula (I) in a solvent comprising acetonitrile and water; adding an acetone solvent thereto; and then cooling it down.

For example, crystal form N2 can be obtained by the method comprising the steps of: mixing the hydrochloride salt of the compound (I) and preferably 55 to 95 vol. % and more preferably 75 vol. % of a mixed solution of acetonitrile/water, and heating the mixture preferably to 55 to 85° C. and more preferably to 70° C. to dissolve it; cooling down the solution preferably to 25 to 35° C. and more preferably 30° C. and adding acetone dropwise thereto and stirring it overnight; then separating the precipitated crystal from the slurry; and then drying the obtained wet crystal under reduced pressure with heating it preferably to 70 to 90° C. and more preferably to 80° C.

Crystal form NW4 can be obtained, for example, by the method comprising the steps of: mixing acetonitrile and the hydrochloride salt of the compound of the formula (I) and then cooling down the mixture, or heating the mixture and then cooling it down; and separating the precipitated crystal from the slurry. In this method, crystal form NW4 can be obtained by adjusting a quantitative ratio of acetonitrile and the hydrochloride salt of the compound of the formula (I), or the subsequent cooling or heating temperature.

Crystal form N4 can be obtained by drying crystal form NW4 under reduced pressure.

Each of crystal form Cl6, crystal form Cl7 and crystal form Cl8 can be obtained by the method comprising the steps of: using diethyl ether, 1,2-dimethoxyethane (DME), and 2-propanol as a solvent, respectively, and diluting a hydrochloric acid with each solvent to prepare it to become 0.05 to 1.00 mmol/mL in concentration; adding the diluent to the compound (free form) of the formula (I) and heating the mixture with stirring preferably to 50 to 80° C. and more preferably to 60° C.; then, comparatively slowly (at a cooling rate of 0.5 to 10° C./hour) cooling it down to 2 to 20° C. and preferably to 5° C.; aging the compound at the same temperature for about 1 to 72 hour(s); and filtering out the precipitated crystal and drying it at room temperature for 24 hours or more under reduced pressure.

The crystal of a sulfate salt of the compound of the formula (I) is either crystal form Su1, crystal form Su2 or crystal form Su3, each of which shows the peak at the specific diffraction angles (2θ) in the powder X-ray diffraction pattern as mentioned in above (5).

Among them, crystal form Su1 can be obtained by the method comprising the steps of: heating the sulfate salt of the compound of the formula (I) preferably at 50 to 80° C. and more preferably at 60° C., preferably in 1,2-ethanediol, cyclohexanone, pyridine or n-heptane and more preferably in pyridine; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal.

Crystal form Su2 can be obtained by the method comprising the steps of: heating the sulfate salt of the compound of the formula (I) preferably at 50 to 80° C. and more preferably at 60° C., preferably in nitromethane or ethyl acetate and more preferably in nitromethane; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal.

Crystal form Su3 can be obtained by the method comprising the steps of: heating the sulfate salt of the compound of the formula (I) preferably at 50 to 80° C. and more preferably at 60° C., preferably in 1,2-dimethoxyethane, ethanol, tetrahydrofuran, acetone or dichloromethane; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. In the case of using ethyl acetate, methanol or diethyl ether as a solvent, crystal form Su3 can also be obtained by the same method as mentioned above provided that the aging time becomes about 72 hours.

The crystal of a hydrobromide salt of the compound of the formula (I) is either crystal form Br1, crystal form Br2, crystal form Br3, crystal form Br4 or crystal form Br5, each of which shows the peak at the specific diffraction angles (2θ) in the powder X-ray diffraction pattern as mentioned in above (6).

Among them, crystal form Br1 can be obtained by the method comprising the steps of: heating the hydrobromide salt of the compound of the formula (I) preferably at 50 to 80° C. and more preferably at 60° C., preferably in cyclohexanone; then, slowly (at a cooling rate of 0.5 to 3° C./hour and preferably 1° C./hour) cooling it down to 2 to 20° C. and preferably to 5° C.; aging the compound at the same temperature for about 1 hour or 72 hours; and collecting the precipitated crystal.

Crystal form Br2 can be obtained by the method comprising the steps of: heating the hydrobromide salt of the compound of the formula (I) preferably at 50 to 80° C. and more preferably at 60° C., preferably in water; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. However, it is preferable to obtain crystal form Br2 by the same method as mentioned above provided that water or ethanol is used as a solvent and the aging time becomes about 72 hours.

Crystal form Br3 can be obtained by the method comprising the steps of: heating the hydrobromide salt of the compound of the formula (I) preferably at 50 to 80° C. and more preferably at 60° C., preferably in acetone, acetonitrile or 2-propanol and more preferably in acetonitrile; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal.

Crystal form Br4 can be obtained by the method comprising the steps of: heating the hydrobromide salt of the compound of the formula (I) preferably at 50 to 80° C. and more preferably at 60° C., preferably in 2-butanol, 2-propanol or tetrahydrofuran and more preferably in tetrahydrofuran; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. However, it is preferable to obtain crystal form Br4 by the same method as mentioned above provided that the above solvents, acetonitrile or diisopropylether is used as a solvent and the aging time becomes about 72 hours. In such a case, it is particularly preferable to use 2-butanol or tetrahydrofuran.

Crystal form Br5 can be obtained by the method comprising the steps of: heating the hydrobromide salt of the compound of the formula (I) preferably at 50 to 80° C. and more preferably at 60° C., preferably in ethyl acetate, acetone or 1,2-dimethoxyethane and more preferably in ethyl acetate or 1,2-dimethoxyethane; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. However, it is preferable to obtain crystal form Br5 by the same method as mentioned above provided that ethyl acetate or 1,2-dimethoxyethane is used as a solvent and the aging time becomes about 72 hours.

The crystal of a phosphate salt of the compound of the formula (I) is either crystal form Pho1, crystal form Pho2, crystal form Pho3 or crystal form Pho4, each of which shows the peak at the specific diffraction angles (2θ) in the powder X-ray diffraction pattern as mentioned in above (7).

Among them, crystal form Pho1 can be obtained by the method comprising the steps of: heating the phosphate salt of the compound of the formula (I) preferably at 50 to 80° C. and more preferably at 60° C., preferably in cyclohexanone, pyridine, acetone or dichloromethane and more preferably in cyclohexanone, pyridine or acetone; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. However, it is also preferable to obtain crystal form Pho1 by the same method as mentioned above provided that N,N-dimethylacetamide or acetone is used as a solvent and the aging time becomes about 72 hours.

Crystal form Pho2 can be obtained by the method comprising the steps of: heating the phosphate salt of the compound of the formula (I) preferably at 50 to 80° C. and more preferably at 60° C., preferably in 1,1,2,2-tetrachloroethane, 1,2-dimethoxyethane, nitromethane, water, n-heptane, isopropyl acetate, acetonitrile, ethyl acetate, diisopropyl ether, tetrahydrofuran or diethyl ether and more preferably in water; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal.

Crystal form Pho3 can be obtained by the method comprising the steps of: heating the phosphate salt of the compound of the formula (I) preferably at 50 to 80° C. and more preferably at 60° C., preferably in methanol; then, slowly (at a cooling rate of 0.5 to 3° C./hour and preferably 1° C./hour) cooling it down to 2 to 20° C. and preferably to 5° C.; aging the compound at the same temperature for about 1 hour or 72 hours; and collecting the precipitated crystal.

Crystal form Pho4 can be obtained by the method comprising the steps of: heating the phosphate salt of the compound of the formula (I) preferably at 50 to 80° C. and more preferably at 60° C., preferably in 2,2,2-trifluoroethanol; then, slowly (at a cooling rate of 0.5 to 3° C./hour and preferably 1° C./hour) cooling it down to 2 to 20° C. and preferably to 5° C.; aging the compound at the same temperature for about 1 hour or 72 hours; and collecting the precipitated crystal.

The crystal of a maleate salt of the compound of the formula (I) is either crystal form Mal1, crystal form Mal2 or crystal form Mal3, each of which shows the peak at the specific diffraction angles (2θ) in the powder X-ray diffraction pattern as mentioned in above (8).

Among them, crystal form Mal1 can be obtained by the method comprising the steps of: heating the maleate salt of the compound of the formula (I) preferably at 50 to 80° C. and more preferably at 60° C., preferably in nitromethane, 2-butanol, isopropyl acetate, 2-propanol or ethanol and more preferably in 2-butanol, 2-propanol or ethanol; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal.

Crystal form Mal2 can be obtained by the method comprising the steps of: heating the maleate salt of the compound of the formula (I) preferably at 50 to 80° C. and more preferably at 60° C., preferably in 1,2-dimethoxyethane, acetonitrile or ethyl acetate; then, slowly (at a cooling rate of 0.5 to 3° C./hour and preferably 1° C./hour) cooling it down to 2 to 20° C. and preferably to 5° C.; aging the compound at the same temperature for about 1 hour or 72 hours; and collecting the precipitated crystal.

Crystal form Mal3 can be obtained by the method comprising the steps of: heating the maleate salt of the compound of the formula (I) preferably at 50 to 80° C. and more preferably at 60° C., preferably in acetone; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal.

The crystal of an acetate salt of the compound of the formula (I) is either crystal form Aca1, crystal form Aca2 or crystal form Aca3, each of which shows the peak at the specific diffraction angles (2θ) in the powder X-ray diffraction pattern as mentioned in above (9).

Among them, crystal form Aca1 can be obtained by the method comprising the steps of: heating the acetate salt of the compound of the formula (I) preferably at 50 to 80° C. and more preferably at 60° C., preferably in nitromethane, acetonitrile or acetone and more preferably in acetone; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. However, it is preferable to obtain crystal form Aca1 by the same method as mentioned above provided that isopropyl acetate, acetonitrile or acetone is used as a solvent and the aging time becomes about 72 hours.

Crystal form Aca2 can be obtained by the method comprising the steps of: heating the acetate salt of the compound of the formula (I) preferably at 50 to 80° C. and more preferably at 60° C., preferably in 2-butanol; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal.

Crystal form Aca3 can be obtained by the method comprising the steps of: heating the acetate salt of the compound of the formula (I) preferably at 50 to 80° C. and more preferably at 60° C., preferably in ethyl acetate; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. However, it is preferable to obtain crystal form Aca by the same method as mentioned above provided that 2-propanol is used as a solvent and the aging time becomes about 72 hours.

The crystal of a D-tartrate salt of the compound of the formula (I) is either crystal form Tar1 or crystal form Tar2, each of which shows the peak at the specific diffraction angles (2θ) in the powder X-ray diffraction pattern as mentioned in above (10).

Among them, crystal form Tar1 can be obtained by the method comprising the steps of: heating the D-tartrate salt of the compound of the formula (I) preferably at 50 to 80° C. and more preferably at 60° C., preferably in cyclohexanone, nitromethane, 1,2-dimethoxyethane or acetone and more preferably in cyclohexanone; then, slowly (at a cooling rate of 0.5 to 3° C./hour and preferably 1° C./hour) cooling it down to 2 to 20° C. and preferably to 5° C.; aging the compound at the same temperature for about 1 hour; and collecting the precipitated crystal. However, it is preferable to obtain crystal form Tar1 by the same method as mentioned above provided that cyclohexanone is used as a solvent and the aging time becomes about 72 hours.

Crystal form Tar2 can be obtained by the method comprising the steps of: heating the D-tartrate salt of the compound of the formula (I) preferably at 50 to 80° C. and more preferably at 60° C., preferably in methanol; then, slowly (at a cooling rate of 0.5 to 3° C./hour and preferably 1° C./hour) cooling it down to 2 to 20° C. and preferably to 5° C.; aging the compound at the same temperature for about 1 hour or 72 hours; and collecting the precipitated crystal.

The crystal of an L-tartrate salt of the compound of the formula (I) is either crystal form L-Tar1 or crystal form L-Tar2, each of which shows the peak at the specific diffraction angles (2θ) in the powder X-ray diffraction pattern as mentioned in above (11).

These crystals can be obtained by the method comprising the steps of: dissolving the compound of the formula (I) together with an L-tartaric acid preferably in 1,2-dimethoxyethane (for crystal form L-Tar1) or acetone (for crystal form L-Tar2); heating the dissolved solution preferably at 50 to 80° C. and more preferably at 60° C.; then, comparatively slowly (at a cooling rate of 0.5 to 10° C./hour and preferably 1° C./hour) cooling it down to 2 to 20° C. and preferably to 5° C.; aging the compound at the same temperature; and filtering out the precipitated crystal and drying it under reduced pressure.

The crystal of a methanesulfonate salt of the compound of the formula (I) is either crystal form Ms1, crystal form Ms2, crystal form Ms3, crystal form Ms4 or crystal form Ms5, each of which shows the peak at the specific diffraction angles (2θ) in the powder X-ray diffraction pattern as mentioned in above (12).

These crystals can be obtained by the method comprising the steps of: dissolving the compound of the formula (I) together with a methanesulfonic acid preferably in methanol (for crystal form Ms1), THF (for crystal form Ms2), t-butyl methyl ether (for crystal form Ms3), DME (for crystal form Ms4) or acetone (for crystal form Ms5); heating the dissolved solution preferably at 50 to 80° C. and more preferably at 60° C.; then, comparatively slowly (at a cooling rate of 0.5 to 10° C./hour and preferably 1° C./hour) cooling it down to 2 to 20° C. and preferably to 5° C.; aging the compound at the same temperature; and filtering out the precipitated crystal and drying it under reduced pressure.

The crystal of a citrate salt of the compound of the formula (I) is either crystal form Ca1, crystal form Ca2, crystal form Ca3 or crystal form Ca4, each of which shows the peak at the specific diffraction angles (2θ) in the powder X-ray diffraction pattern as mentioned in above (13).

These crystals can be obtained by the method comprising the steps of: dissolving the compound of the formula (I) together with a citric acid preferably in IPA (2-propanol) (for crystal form Ca1), 1-butanol (for crystal form Ca2), DME (for crystal form Ca3) or acetone (for crystal form Ca4); heating the dissolved solution preferably at 50 to 80° C. and more preferably at 60° C.; then, comparatively slowly (at a cooling rate of 0.5 to 10° C./hour and preferably 1° C./hour) cooling it down to 2 to 20° C. and preferably to 5° C.; aging the compound at the same temperature; and filtering out the precipitated crystal and drying it under reduced pressure.

In the present specification, "propanol" means 1-propanol or 2-propanol and preferably 2-propanol. Similarly, "butanol" means 1-butanol, 2-butanol, 2-methyl-1-propanol or tert-butanol and preferably 1-butanol.

Meanwhile, the peaks of the diffraction angles (2θ) in the powder X-ray diffraction pattern can slightly change due to nuances such as the measurement condition or the like. The diffraction angles described in the present specification can accept such error.

Further, the overall pattern is important in 13C-NMR spectra, infrared spectra or DSC data in order to identify the crystals. Such spectra can slightly change due to the measurement condition or the like.

In the above production methods, the aging time of 1 hour can be changed to 30 minutes to 5 hours. Similarly, about 72 hours can be changed to 48 hours or more, and preferably 48 to 120 hours.

Crystal form Cl5, crystal form Br3, crystal form Br4, crystal form Br5 and crystal form Mal2 are preferable among the above crystals. Crystal form Cl5 and crystal form Br5 are particularly preferable. In addition to them, crystal form N2 is also particularly preferable.

Salts of the compound of the formula (I) used for producing the crystals of the present invention may be those which are salts before they are added to a solvent, or they may become salts in the reaction when the free form is added to a solvent and then a corresponding acid is further added thereto.

When preparing the above salts, it is preferable to add a hydrochloric acid or the like to the compound (free form) of the formula (I) so that an acid such as a hydrogen chloride, hydrogen bromide and an acetic acid becomes 1:1 or more in a molar ratio, preferably around 1:1.05 to 1:1.2 in a molar ratio and more preferably 1:1.1 in a molar ratio.

Salts of the compound of the formula (I), particularly a hydrochloride salt, hydrobromide salt and maleate salt thereof are useful in itself in that they become raw materials of the above preferable crystals.

Further, the amount of a solvent for precipitating crystals can be optional. When the compound (free form) of the formula (I) or salts thereof is 1 part by weight, the solvent is preferably 2 to 1000 parts by weight and particularly preferably 5 to 40 parts by weight.

In the production methods of the present invention, another crystal may be produced by another production method of the present invention by using the crystal which is prepared by using amorphia or an amorphous solid substance, as well as the production method by using amorphia or an amorphous solid substance itself.

The crystals of the present invention are easy to be used and excellent in "preservation stability" or "humidity resistance" of drug substances or drug products and, therefore, they are useful in that they are crystals which can be manufactured on the industrial scale. In addition to them, such crystals are also excellent in solubility.

The compound of the above formula (I) which is a prodrug of the compound of the above formula (II) has an excellent durability of the effect particularly after the oral administration. Besides, since its membrane permeability is good, the area under the plasma concentration-time curve and bioavailability thereof are high in oral administration. The compound is also excellent in safety.

Thus, the crystals of the present invention can be used as excellent a 4 integrin inhibitors. Further, they can be effectively used as an active ingredient of therapeutic agents or preventive agents for inflammatory diseases in which a 4 integrin-depending adhesion process participates in the pathology, such as rheumatoid arthritis, inflammatory bowel diseases (including Crohn's disease and ulcerative colitis), systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis or transplantation rejection.

In addition, the crystals can be effectively used as an active ingredient of therapeutic agents or preventive agents for preeclampsia, ischemic cerebrovascular disorders (including cerebral infarction), systemic sclerosis, ankylosing spondylitis, arthritis psoriatica, sarcoidosis, giant cell arteritis, uveitides, fibroid lung, chronic obstructive pulmonary disease, osteoarthritis, Alzheimer's disease, spinal cord injury, traumatic brain injury, primary sclerosing cholangitis, liver cirrhosis caused by hepatitis C, active chronic hepatitis, sacroiliitis, ankylosing spondylitis, episceritis, iritis, uveitis, erythema nodosum, pyoderma gangrenosum and autoimmune hepatitis.

Further, the crystals can be effectively used as an active ingredient of therapeutic agents or preventive agents for the diseases in which α14 integrin may participate in the pathology in addition to the above diseases.

The administered dose used for the above purposes is determined by the intended therapeutic effect, administration method, treatment period, age, body weight and the like. For example, by an oral or parenteral route (such as intravenous, intra-arterial, subcutaneous or intramuscular administration, suppositories, enema administration, ointment, patch, sublingual administration, eye-drops, inhalation and the like), the dose is usually 1 µg to 5 g and preferably 1 mg to 1 g a day for adults in the oral administration, and 0.01 µg to 1 g a day for adults in the parenteral administration.

The crystals of the present invention can be applied to various dosage forms, and they can be prepared to pharmaceutical compositions without change or with various pharmaceutically acceptable carriers.

The pharmaceutical compositions comprising the crystal (s) of the present invention preferably contain the crystal(s) of the present invention more than the ratio in which the practical therapeutic effect can be produced. The ratio in which the practical therapeutic effect can be produced is determined by the administered dose of the above pharmaceutical composition, the intended therapeutic effect, or the like.

Examples of pharmaceutically acceptable carriers include various common organic or inorganic carriers as materials for preparation, such as excipients, lubricants, binders, disintegrating agents, water-soluble polymers, and basic inorganic salts in solid preparations; and solvents, solubilizing agents, suspending agents, tonicity agents, buffers, and soothing agents in liquid preparations. If necessary, it is possible to use common additives such as antiseptic agents, antioxidants, coloring agents, sweetening agents, acidulants, foaming agents, flavoring agents, or the like.

The dosage forms of such pharmaceutical compositions are, for example, tablets, powders, pills, granules, capsules, suppositories, solutions, sugar-coated tablets, depots, syrups, suspending agents, emulsions, troches, sublingual agents, patches, oral disintegrating agents (tablets), inhalers, enema agents, ointments, patches, adhesives and eye-drops. They can be prepared with ordinary preparation additives by ordinary methods.

The above pharmaceutical compositions can be produced by common methods in the preparation technical field and, for instance, by the methods described in Japanese Pharmacopoeia. The production methods of preparations are described below in detail.

For example, when the crystals of the present invention are prepared as oral preparations, excipients and, if necessary, binders, disintegrating agents, lubricants, coloring agents, flavoring and freshening substance are added to the crystals. Then, they are formed as tablets, powders, pills, granules, capsules, suppositories, solutions, sugar-coated tablets, depots, syrups, suspending agents, emulsions, troches, sublingual agents, oral disintegrating agents (tablets), inhalers or the like in accordance with ordinary methods. Examples of excipients include lactose, corn starch, sucrose, glucose, sorbit and crystalline cellulose. Examples of binders include polyvinyl alcohol, polyvinyl ether, ethylcellulose, methylcellulose, gum arabic, tragacanth, gelatin, shellac, hydroxypropylcellulose, hydroxypropylstarch and polyvinyl pyrrolidone. Examples of disintegrating agents are starch, agar, gelatin powder, crystalline cellulose, calcium carbonate, sodium hydrogen carbonate, calcium citrate, dextran and pectin. Examples of lubricants are magnesium stearate, tarc, polyethylene glycol, silica, hydrogenated vegetable oil. Examples of coloring agents are those which are permitted to be added to pharmaceutical compositions. Further, cocoa powder, menthol, aromatic acids, peppermint oil, borneol, cinnamon powder and the like are used as flavoring and freshening substance. These tablets or granules may be coated, if necessary, with sugar, gelatin and the like.

When injectable agents are prepared, pH adjusters, buffers, stabilizing agents, preservatives or the like are added thereto, if necessary, and then they are prepared as subcutaneously, intramuscularly or intravenously injectable agents in accordance with ordinary methods.

Next, Examples will further illustrate the production of the crystals of the present invention. They only explain the present invention and do not particularly limit the invention.

REFERENTIAL EXAMPLE 1

Synthesis of the Compound (Free Form) of the Formula (I)

Process 1: Synthesis of isopropyl ester of 4-nitro-N-(2,6-dichlorobenzoyl)-L-phenylalanine Isopropanol (130 mL), tetrahydrofuran (50 mL) and a sulfuric acid (0.44 mL) were added to 4-nitro-N-(2,6-dichlorobenzoyl)-L-phenylalanine (Patent Literature 3: WO2004/074264) (2.95 g, 7.70 mmol) and stirred at 50° C. for 5 days. After removing the solvent under reduced pressure, the obtained solid substance was washed with water and dried to obtain the title compound (3.28 g).

MS (ESI) m/z 425 (MH+)

Process 2: Synthesis of isopropyl ester of 4-amino-N-(2,6-dichlorobenzoyl)-L-phenylalanine (Namely, Synthesis of isopropyl ester of (S)-2-(2,6-dichlorobenzoylamino)-3-(4-aminophenyl) propionic acid Isopropanol (6 mL), tetrahydrofuran (3 mL) and 3% Pt—S/C (20 mg) were added to the compound obtained in Process 1 (98 mg) and stirred under hydrogen atmosphere at room temperature overnight. After filtering the reaction solution, the filtrate was washed with isopropanol and condensed under reduced pressure to obtain the title compound (92 mg).

MS (ESI) m/z 395 (MH+)

Process 3: Synthesis of isopropyl ester of 4-[(2-amino-5-iodobenzoyl) amino]-N-(2,6-dichlorobenzoyl)-L-phenylalanine The compound obtained in Process 2 (26.9 g), 1-hydroxybenzotriazole monohydrate (11.5 g) and 5-iodoanthranilic acid (17.8 g) were dissolved in dimethylformamide (200 mL) and cooled down to 0° C. Then, 1-ethyl-3-(3-dimethylaminopropyl)carbodiimide hydrochloride (13.7 g) was added thereto and stirred at room temperature for 16 hours. The organic layer to which ethyl acetate was added was washed with a 0.1N aqueous solution of sodium hydroxide, water, a 0.1N hydrochloric acid and a saturated saline solution respectively, and dried with anhydrous sodium sulfate. After removing the solvent under reduced pressure, the residue was suspended in methylene chloride and hexane, filtered out and dried to obtain the title compound (37.06 g).

MS (ESI MH+): 640

Process 4: Synthesis of isopropyl ester of N-(2,6-dichlorobenzoyl)-4-(6-iodo-2,4-dioxo-1,2,3,4-tetrahydroquinazoline-3(2H)-yl)-L-phenylalanine N,N-carbonyldiimidazole (28.16 g) was dissolved in 150 mL of dimethylformamide and heated up to 80° C. A dimethylformamide solution (150 mL) of the compound obtained in Process 3 (37.06 g) was added dropwise thereto and stirred overnight. After cooling it down to room temperature, ethyl acetate and water were added thereto and extraction was conducted. Then, the organic layer thereof was washed with water and a saturated saline solution respectively, and dried with anhydrous sodium sulfate. After removing the solvent under reduced pressure, the obtained solid substance was suspended in methylene chloride and hexane, filtered out and dried to obtain the title compound (33.06 g).

MS (ESI MH+): 666

Process 5: Synthesis of isopropyl ester of N-(2,6-dichlorobenzoyl)-4-(6-iodo-1-methyl-2,4-dioxo-1,2,3,4-tetrahydroquinazoline-3(2H)-yl)-L-phenylalanine The compound obtained in Process 4 (33.06 g) and potassium carbonate (14.5 g) were added to dimethylformamide (200 mL), and then iodomethane (10 mL) was further added thereto. After stirring the mixture at room temperature for 4 hours, the insoluble substance was filtered by Celite filtration. Then, ethyl acetate and water were added to the filtrate and extraction was conducted. The obtained organic layer was washed with a 1N hydrochloric acid, a saturated sodium bicarbonate water and a saturated saline solution respectively. After removing the solvent, the obtained solid substance was suspended in methylene chloride and hexane, filtered out and dried to obtain the title compound (31.85 g).

MS (ESI MH+): 680

Process 6: Synthesis of isopropyl ester of N-(2,6-dichlorobenzoyl)-4-(6-carboxy-1-methyl-2,4-dioxo-1,2,3,4-tetrahydroquinazoline-(2H)-yl)-L-phenylalanine The compound obtained in Process 5 (31.85 g) was dissolved in dimethylformamide (140 mL), and triethylamine (13.1 mL) and water (8.5 mL) were added thereto. After bubbling carbon monoxide, palladium acetate (52 mg) was further added thereto and stirred at 70° C. under carbon monoxide atmosphere for 11 hours. After filtering the insoluble substance by Celite filtration, dimethylformamide was removed under reduced pressure. Then, ethyl acetate and a 1N hydrochloric acid were added thereto and extraction was conducted. The obtained organic layer was washed with a 1N hydrochloric acid and a saturated saline solution respectively, and dried with sodium sulfate. After removing the solvent under reduced pressure, the obtained solid substance suspended in methylene chloride and hexane, filtered out and dried to obtain the title compound (27.23 g).

MS (ESI MH+): 598

Process 7: Synthesis of isopropyl ester of N-(2,6-dichlorobenzoyl)-4-[6-(hydroxymethyl)-1-methyl-2,4-dioxo-1,2,3,4-tetrahydroquinazoline-3 (2H)-yl]-L-phenylalanine The compound obtained in Process 6 (27.23 g) was dissolved in tetrahydrofuran (200 mL). Triethylamine (9.51 mL) was added thereto and cooled down to 0° C. Then, ethyl chloroformate (4.56 mL) was added dropwise thereto and stirred for 30 minutes. After filtering out the insoluble substance, the filtrate was cooled down to 0° C. and sodium borohydride (2.58 g) and ice (5 pieces) were added thereto. After stirring it for 1 hour, sodium borohydride (0.25 g) was further added thereto and stirred for 20 minutes. Then, a 1N hydrochloric acid, and then ethyl acetate and water were added thereto and extraction was conducted. The organic layer thereof was washed with a 0.3N hydrochloric acid, water, a saturated sodium bicarbonate water and a saturated saline solution respectively. After removing the solvent, the obtained solid substance was suspended in methylene chloride and hexane, filtered out and dried to obtain the title compound (25.69 g).

MS (ESI MH+): 584

Process 8: Synthesis of isopropyl ester of 4-[6-(chloromethyl)-1-methyl-2,4-dioxo-1,2,3,4-tetrahydroquinazoline-3(2H)-yl]-N-(2,6-dichlorobenzoyl)-L-phenylalanine A mixed solvent of methylene chloride (140 mL) and dimethylformamide (140 mL) was cooled down to 0° C., and then phosphorous oxychloride (40.1 mL) was added thereto and stirred for 30 minutes. Then, the compound obtained in Process 7 (25.69 g) was added thereto at 0° C. and stirred at room temperature for 1 hour. Further, phosphorous oxychloride (0.4 mL) was added thereto and stirred for 1 hour. Then, ethyl acetate (400 mL) and a saturated sodium bicarbonate water (100 mL) were further added thereto and vigorously stirred. After ethyl acetate (500 mL) and water (200 mL) were added thereto to separate layers, the organic layer thereof was washed with a saturated sodium bicarbonate water, an aqueous solution of 1N sodium hydroxide and a saturated saline solution. Then, the layer was dried with anhydrous sodium sulfate. After removing the solvent under reduced pressure, the obtained solid substance was suspended in methylene chloride and hexane, filtered out and dried to obtain the title compound (20.32 g).

MS (ESI MH+): 602

Process 9: Synthesis of isopropyl ester of N-(2,6-dichlorobenzoyl)-4-[6-(methylamino)methyl-1-methyl-2,4-dioxo-1,4-dihydroquinazoline-3(2H)-yl]-L-phenylalanine [the compound (free form) of the formula (I)]

An acetonitrile solution (450 mL) of the compound obtained in Process 8 (20.32 g) was added dropwise to a mixed solution of a 2M methylamine-tetrahydrofuran solution (200 mL) and acetonitrile (100 mL). The mixture was stirred at room temperature for 10 hours, and the solvent was removed under reduced pressure. A part of the obtained crude product was purified with silica gel column chromatography (chloroform-methanol, 5:1), and the residue was dissolved in chloroform and filtered. After condensing it under reduced pressure, water-acetonitrile was added thereto, and acetonitrile was removed under reduced pressure. Then, the residue was freeze-dried to obtain the title compound (2.04 g).

MS (ESI MH+): 597

$^1$H-NMR (DMSO-$d_6$): δ 1.17 (3H, d, J=6.3 Hz), 1.21 (3H, d, J=6.3 Hz), 2.23 (3H, s), 3.00 (1H, dd, J=14.1, 9.9 Hz), 3.17 (1H, dd, J=14.1, 5.4 Hz), 3.51 (3H, s), 3.69 (2H, s), 4.70-4.80 (1H, m), 4.90-4.99 (1H, m), 7.18 (2H, d, J=8.3 Hz), 7.35-7.45 (6H, m), 7.74 (1H, dd, J=8.6, 2.1 Hz), 7.98 (1H, d, J=2.1 Hz), 9.22 (1H, d, J=8.0 Hz).

REFERENTIAL EXAMPLE 2

Synthesis of the Compound of the Formula (II) (TFA Salt)

A 4N hydrogen chloride-dioxane solution (15 mL) and water (3 mL) were added to the compound (I) obtained in the referential example 1 (500 mg, 0.838 mmol), and stirred at 90° C. for 3 hours. After removing the solvent, the reactant was purified with high-speed liquid chromatography (water/acetonitrile, each containing 0.1% TFA) to obtain the intended compound (330 mg).

MS (ESI MH+): 555

$^1$H-NMR (DMSO-$d_6$) δ 2.58 (3H, t, J=5.1 Hz), 2.98 (1H, dd, J=14.1, 10.5 Hz), 3.24 (1H, dd, J=14.1, 4.5 Hz), 3.55 (3H, s), 4.22-4.28 (1H, m), 4.61-4.80 (1H, m), 7.20 (2H, d, J=8.4 Hz), 7.39-7.46 (5H, m), 7.60 (1H, d, J=9.0 Hz), 7.88 (1H, d, J=6.9 Hz), 8.24 (1H, d, J=1.5 Hz), 8.80 (2H, brs), 9.15 (1H, d, J=8.7 Hz), 12.90 (1H, brs)

TEST EXAMPLE 1

Assay of Antagonistic Activity to VCAM-1/α4β1 Integrin Binding Under the Existence of Blood Serum The capacity of a test substance antagonistic to the binding of cell strain of human T cells, Jurkat (ATCC TIB-152), known to express integrin α4β1, to VCAM-1 was determined.

Fifty μL/well of a solution (500 ng/mL) of recombinant human VCAM-1/Fc (R & D systems) diluted with buffer A (0.1 M NaHCO$_3$, pH 9.6) was added to a 96-well microtiter plate (Nunc Maxisorp). After the incubation thereof at 4° C. overnight and washing it once with PBS, a buffer (buffer B) obtained by diluting Block Ace (Snow Brand Milk Products Co., Ltd.) with PBS to ½ concentration was added in the amount of 150 μL/well. After the incubation thereof at room temperature for 2 hours, buffer B was removed and the plate was washed with PBS once.

Jurkat cells were washed with Dulbecco modified Eagle medium (SIGMA, hereinafter referred to as "DMEM") once. Then, the cells were suspended again in a binding buffer (DMEM containing 20 mM HEPES, 0.1% BSA, 2 mM MnCl$_2$ and 50% human blood serum (Sigma)) to become 1×10$^6$ cells/mL.

Sixty μL of a test substance of various concentrations obtained by the dilution with the binding buffer was added to a round-bottom 96-well plates (IWAKI). Immediately thereafter, 60 μL of the Jurkat cells (1×10$^6$ cells/mL) were added thereto and shaken on a plate shaker (IKA-Labortechnik, IKA-SCHUTTLER MTS-4) at 1000 rpm for 10 seconds. In 120 μmL of the cell suspensions to which the test substance was added, each 100 μL thereof was transferred on the VCAM-1/Fc-coated plate and incubated in dark place at room temperature for 60 minutes. After the shaking on the plate shaker at 1000 rpm for 30 seconds, the solution was immediately removed. Then, the unbound cells were removed by washing them with PBS once. Buffer C (PBS containing 0.82% Triton X-100) was added to the plate in the amount of 70 μL/well. After the shaking on the plate shaker at 1000 rpm for 5 minutes, the bound Jurkat cells were lysed. After centrifuging the cells on a plate centrifuge (SIGMA 4-15C) at room temperature at 2500 rpm for 5 minutes, 50 μL of supernatant thereof was transferred to a 96-well microtiter plate (Nunc Maxisorp). Each 50 μL of Substrate Buffer (Promega, CytoTox 96 Non-Radioactive Cytotoxicity Assay) was added thereto, shaken on a plate shaker at 1000 rpm for 10 seconds and reacted in dark place at room temperature for 30 minutes. Then, each 50 μL of Stop Solution (Promega, CytoTox 96 Non-Radioactive Cytotoxicity Assay) was added thereto and shaken on a plate shaker at 1000 rpm for 10 seconds. Then, its absorbance at 490 nm was determined with a plate reader (Molecular Devices, Vmax).

The absorbance thus obtained detects an activity of lactate dehydrogenase (LDH) dissolved in the supernatant of each well. Namely, the absorbance is proportional to the number of remaining Jurkat cells on the plate via the binding to VCAM-1. The test was conducted in duplicate and the binding rate of each test substance in various concentrations was determined while the absorbance of the test substance-free well was determined to be 100% and the absorbance of the Jurkat-cell-free well was determined to be 0%. The concentration for the 50% binding inhibition, IC$_{50}$, was calculated.

As a result, IC$_{50}$ of the compound of the formula (II) was 11.2 nM, which was highly superior to IC$_{50}$ of the compound of Example 1 in WO 02/16329 (Patent Literature 1), 148.8 nM.

TEST EXAMPLE 2

Pharmacokinetic Study by Intravenous Administration to a Rat

After the compound of the formula (II) which is the active form was weighed by a scale, they were adjusted by dimethylsulfoxide to become 10 mg/mL. Polyethylene glycol 400 and distilled water were added thereto to prepare 1 mg/mL of an administration solution. 1 mg/mL of the administration solution was intravenously administered as a single dose to a Wistar rat in an amount of 1 mL/kg. 1, 5, 10, 30, 60 and 180 minutes later, the drug concentration in the blood plasma obtained by blood drawing from its cervical vein over time under anesthesia was determined with LC/MS. From the obtained results, the area under the plasma concentration time curve from zero to time infinity (AUCinf(iv)) was calculated in accordance with the trapezoidal method of pharmacokinetic analysis. The total body clearance (CLtot, [L/hr/kg]) was calculated as an index of drug disappearance in the blood plasma from a dose [mg/kg] and AUC [μg×hr/mL] in accordance with the formula: CLtot=Dose AUCinf(iv).

As a result, CLtot of the compound of the formula (II) was 0.23[L/hr/kg], which was highly superior to CLtot of the compound of Example 1 in WO 02/16329 (Patent Literature 1), 1.89.

TEST EXAMPLE 3

Activity to Elevate the Number of Lymphocytes in the Peripheral Blood in a Rat

After the substance inhibiting the bond between α4 integrin and VCAM-1 is administered in vivo, in case its inhibitory activity works effectively, it is suggested that the number of lymphocytes in the peripheral blood is increasing by inhibiting adhesion of lymphocytes to the blood vessels or organs. Therefore, the activity of the compound of the formula (I) to elevate the number of lymphocytes in the rat was examined.

The dosing solution was prepared by dissolving the compound of the formula (I) in dimethylsulfoxide, adding a mixed solution of polyethylene glycol 400: propylene glycol=1:1 thereto and turning it upside and down repeatedly. The final concentration of DMSO was adjusted to 2.5%.

The dosing solution of a test substance (30 mg/kg) was orally administered to male Wistar rats (6 to 8 weeks age) in the amount of 4 mL/kg. After the settled time points after the administration, the blood was drawn from the abdominal large vein under anesthesia and mixed in an EDTA-2K coated container for blood collection. Then, the number of lymphocytes in the peripheral blood was determined by an automated comprehensive hematology analyzer (SF-3000, Sysmex). The test was conducted in n=5, and the ratio (%) of the number of lymphocytes in the peripheral blood in a test substance-administered group to that in a vehicle-treated group (a control group) was calculated while the average value of the number of lymphocytes in the peripheral blood in a control group was determined to be 100%.

Evaluation of the number of lymphocyte in the peripheral blood after 12 hours after administration results that the compound of Example 190 in WO02/16329 (Patent Literature 1) was failed (120%) and the compound of the formula (I) was passed (150% or higher).

Measurement Method 1 Powder X-Ray Diffraction Pattern

The measurement condition of the powder X-ray diffraction pattern described in Examples 1 to 15 is as follows:

Device: Bruker GADDS diffractometer

Target: CuKα monochromator

Voltage: 40 kV

Current: 40 mV

Total time: 90 seconds or 180 seconds

2 θ range: 1.5 to 41.5°

EXAMPLE 1

Preparation of Crystal Form A

Process 1

The compound (free form) of the formula (I) prepared in the referential example was dissolved in tetrahydrofuran (THF), and the solvent was removed under reduced pressure to obtain amorphia of the compound (I).

Process 2

3 mg of the compound (I) obtained in Process 1 was added to 40 μL of dimethylformamide and heated up to 60° C. Then, the reactant was quickly cooled down to 5° C. (at a cooling rate of 30° C./hour), aged at the same temperature for about 24 hours, and then the precipitated crystal was collected. The obtained crystal was in the form of a hydrate. FIG. 1 shows the powder X-ray diffraction pattern thereof.

EXAMPLE 2

Preparation of Crystal Form B 3 mg of the compound (free form) of the formula (I) prepared in Process 1 of Example 1 was added to 40 μL of t-butanol and heated up to 60° C. Then, the reactant was quickly cooled down to 5° C. (at a cooling rate of 30° C./hour), aged at the same temperature for about 24 hours, and then the precipitated crystal was collected.

In addition to it, the crystal was also collected by the same method as mentioned above provided that the solvent was changed to 1-butanol or ethanol.

Figure 3:
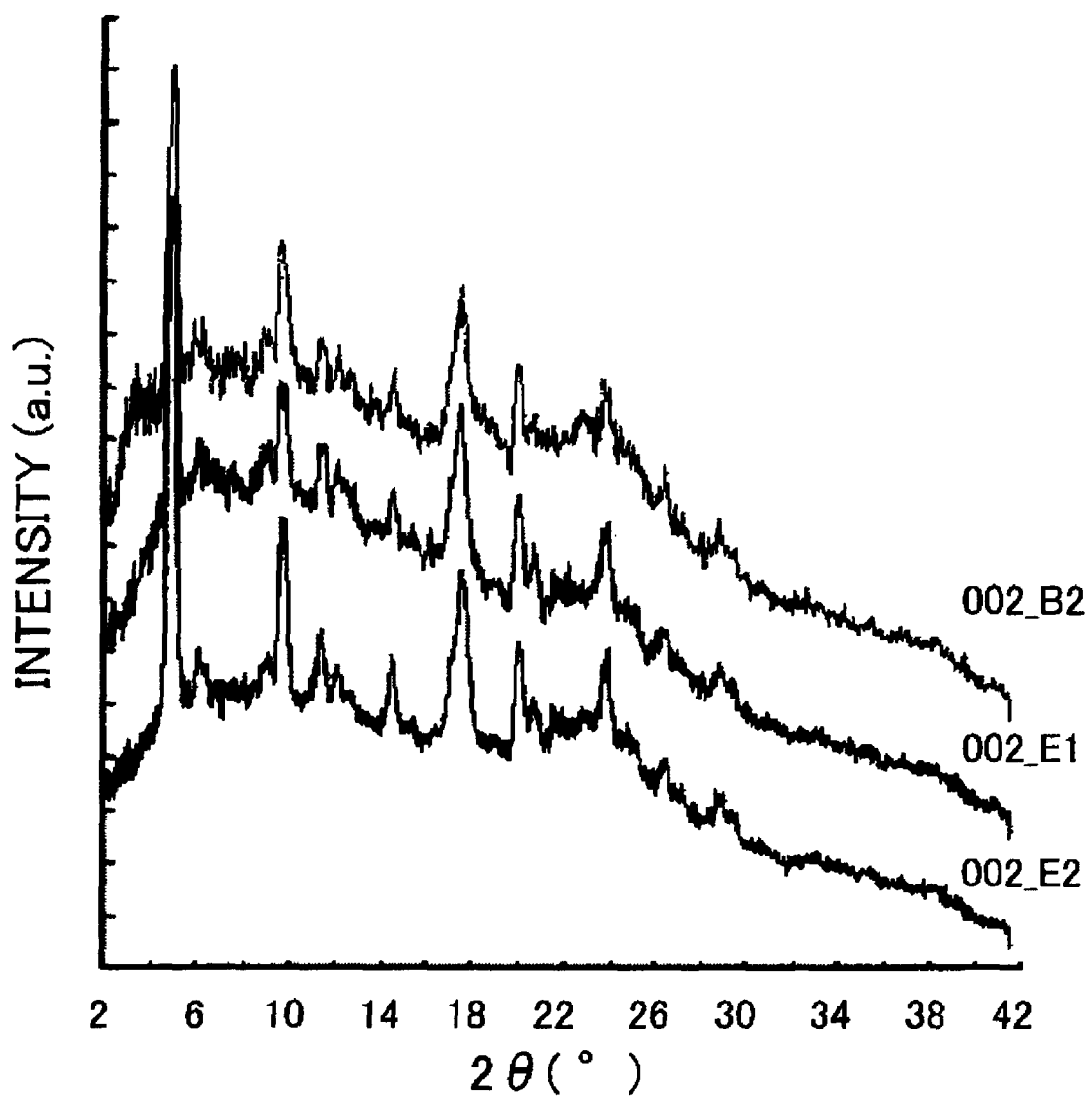
FIG. 3 shows a powder X-ray diffraction pattern of crystal form B of the compound (free form) of the formula (I) of the present invention.

The powder X-ray diffraction pattern of the crystal thus obtained was measured. FIG. 3 shows the result thereof.

In the figure, 002 B2 represents the crystal obtained from t-butanol; 002 E1 represents the crystal obtained from 1-butanol; and 002 E2 represents the crystal obtained from ethanol.

EXAMPLE 3

Preparation of Crystal Form D

Figure 4:
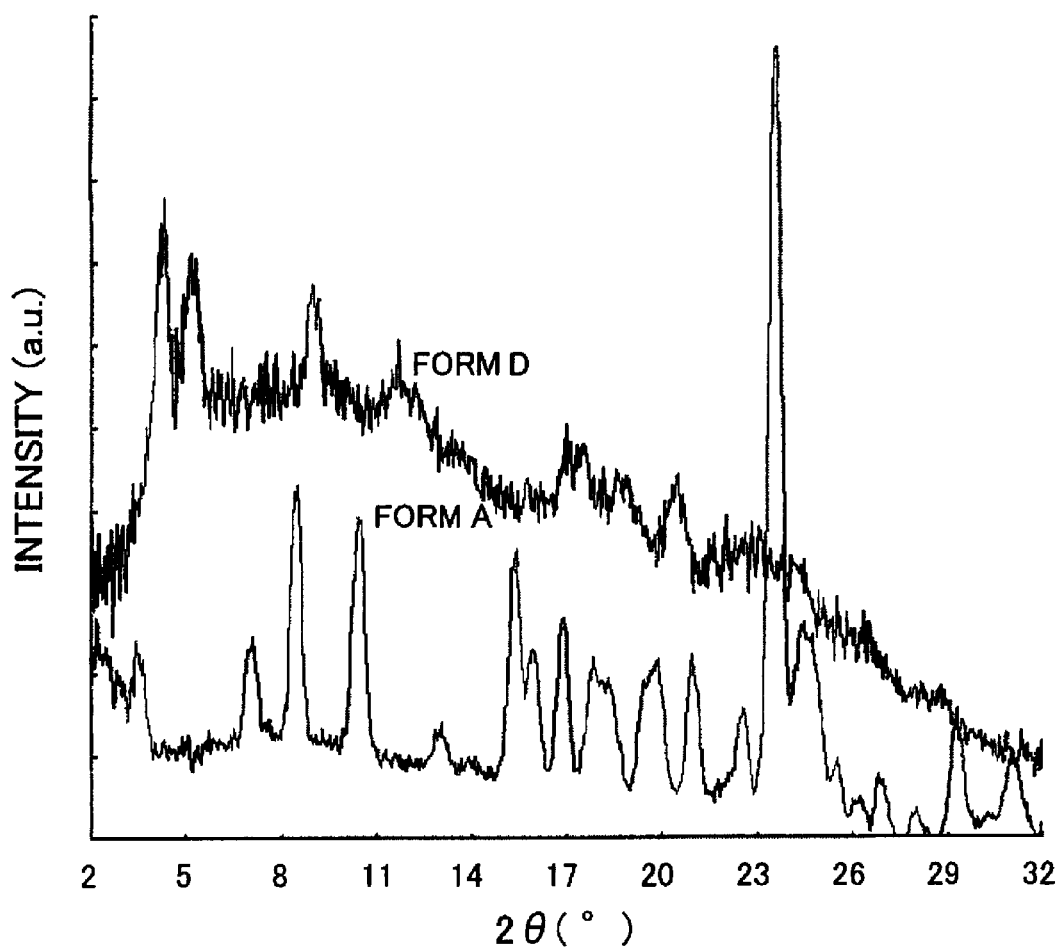
FIG. 4 shows a powder X-ray diffraction pattern of crystal form D of the compound (free form) of the formula (I) of the present invention.

The compound (free form) of the formula (I) prepared in Process 1 of Example 1 was added to methanol to become 75 mg/1 mL in methanol, put in 1 well of a 96-well plate and heated up to 60° C. Then, the reactant was quickly cooled down to 5° C. (at a cooling rate of 30° C./hour), aged at the same temperature for about 24 hours, and then the precipitated crystal was collected. The powder X-ray diffraction pattern of the crystal thus obtained was measured. FIG. 4 shows the result thereof together with the powder X-ray diffraction pattern of crystal form A. In the figure, FORM D represents crystal form D, and FORM A represents crystal form A.

EXAMPLE 4

Preparation of Crystal Form E)

Figure 5:
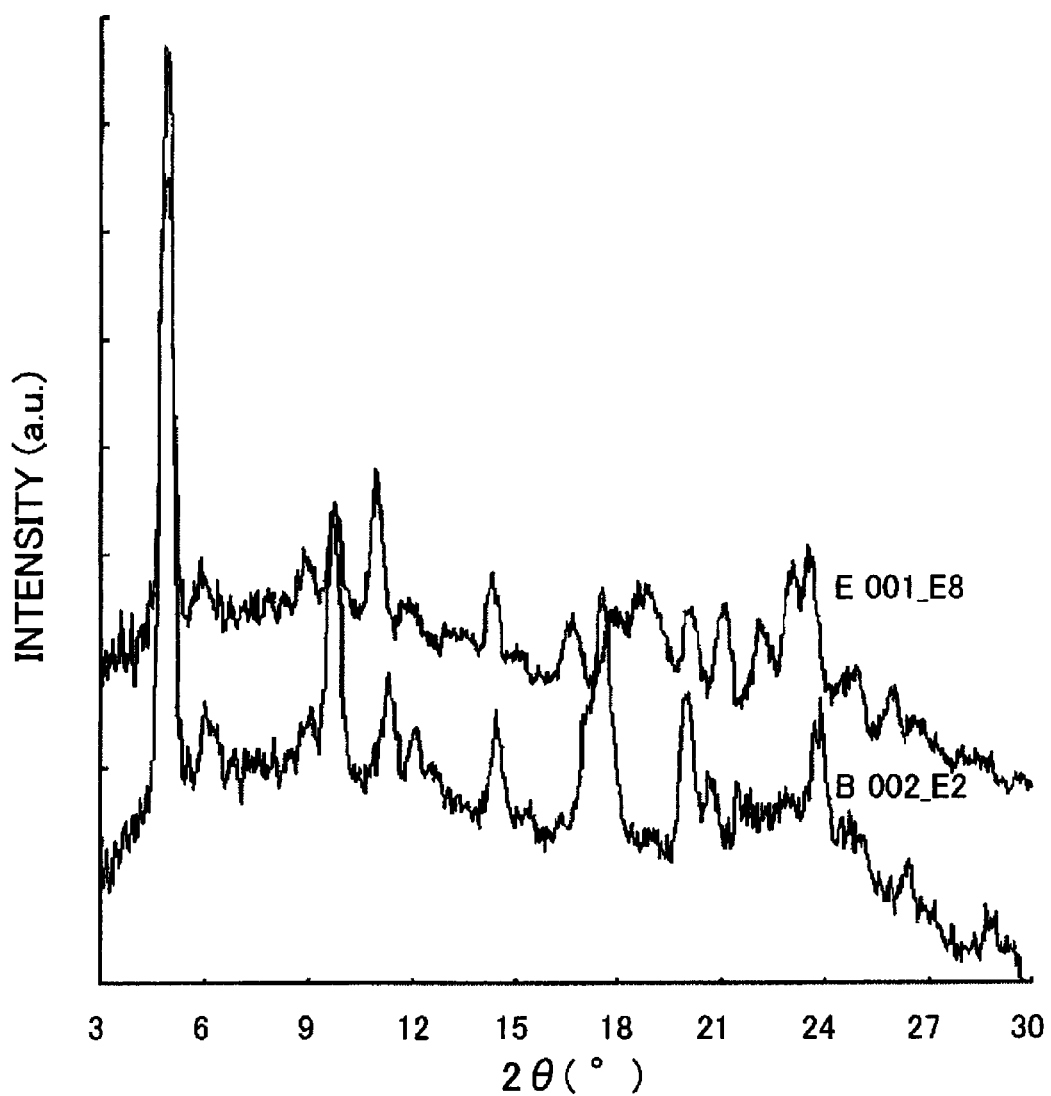
FIG. 5 shows a powder X-ray diffraction pattern of crystal form E of the compound (free form) of the formula (I) of the present invention.

The compound (free form) of the formula (I) prepared in Process 1 of Example 1 was added to ethanol to become 75 mg/1 mL in ethanol, put in 1 well of a 96-well plate and heated up to 60° C. Then, the reactant was slowly cooled down to 5° C. (at a cooling rate of 1° C./hour), aged at the same temperature for about 24 hours, and then the precipitated crystal was collected. The powder X-ray diffraction pattern of the crystal thus obtained was measured. FIG. 5 shows the result thereof together with the powder X-ray diffraction pattern of crystal form B. In the figure, E001_E8 represents crystal form E and B002_E2 represents crystal form B.

EXAMPLE 5

Preparation of Crystal Form F

Figure 6:
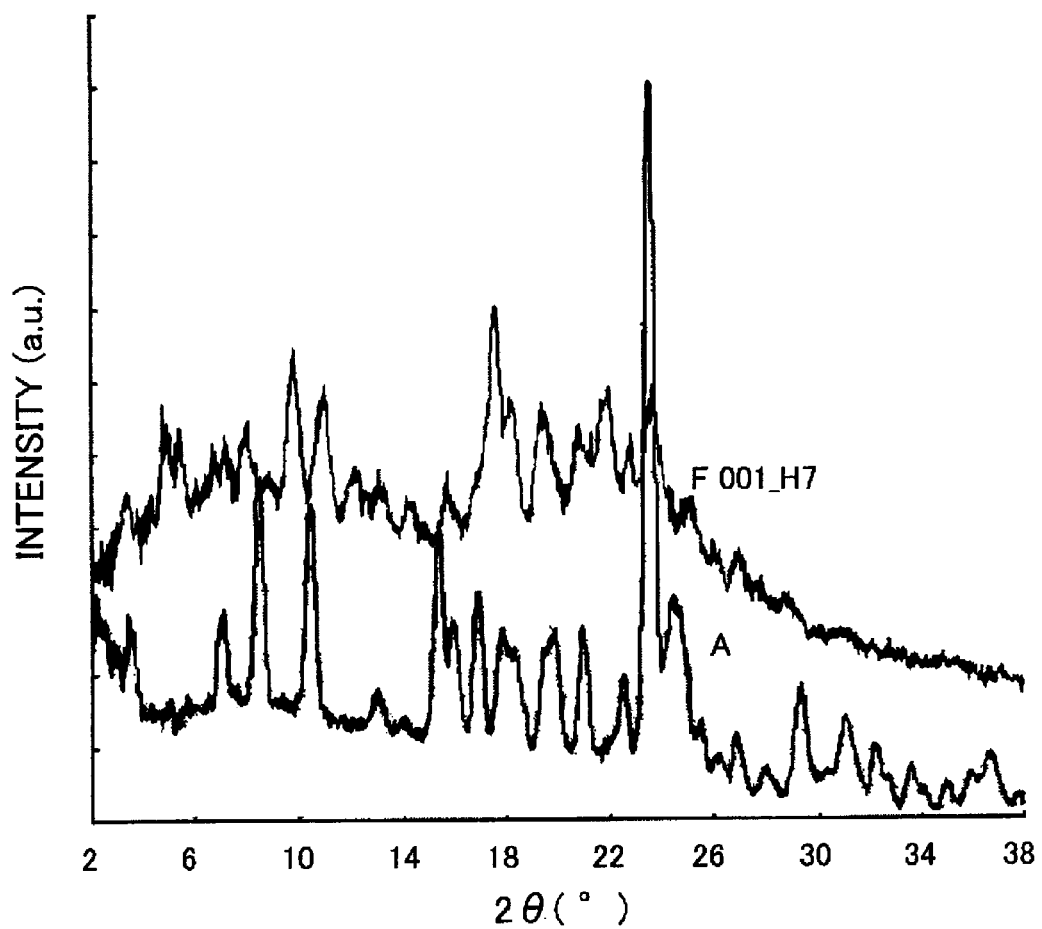
FIG. 6 shows a powder X-ray diffraction pattern of crystal form F of the compound (free form) of the formula (I) of the present invention.

The compound (free form) of the formula (I) prepared in Process 1 of Example 1 was added to t-amyl alcohol to become 75 mg/1 mL in t-amyl alcohol, put in 1 well of a 96-well plate and heated up to 60° C. Then, the reactant was slowly cooled down to 5° C. (at a cooling rate of 1° C./hour), aged at the same temperature for about 24 hours, and then the precipitated crystal was collected. The powder X-ray diffraction pattern of the crystal thus obtained was measured. FIG. 6 shows the result thereof together with the powder X-ray diffraction pattern of crystal form A. In the figure, F001_H7 represents crystal form F and A represents crystal form A.

EXAMPLE 6

Preparation of Crystal Form Cl2 to Crystal Form Cl4)

Nitromethane comprising a hydrogen chloride of which molar ratio to the compound (free form) of the formula (I) prepared in Process 1 of Example 1 becomes 1.1:1 was added to said compound so that the concentration becomes the free form equivalent to 75 mg/1 mL in nitromethane. The mixture was put in 1 well of a 96-well plate and dissolved by being heated up to 60° C. Then, the reactant was slowly cooled down to 5° C. (at a cooling rate of 1° C./hour), aged at the same temperature for about 72 hours, and then the precipitated crystal form Cl2 was collected.

Crystal form Cl3 and crystal form Cl4 were obtained by the same method as mentioned above provided that the following condition was changed:

Crystal form Cl3: use of 2-butanol as the solvent

Crystal form Cl4: use of 2-propanol as the solvent.

Figure 7:
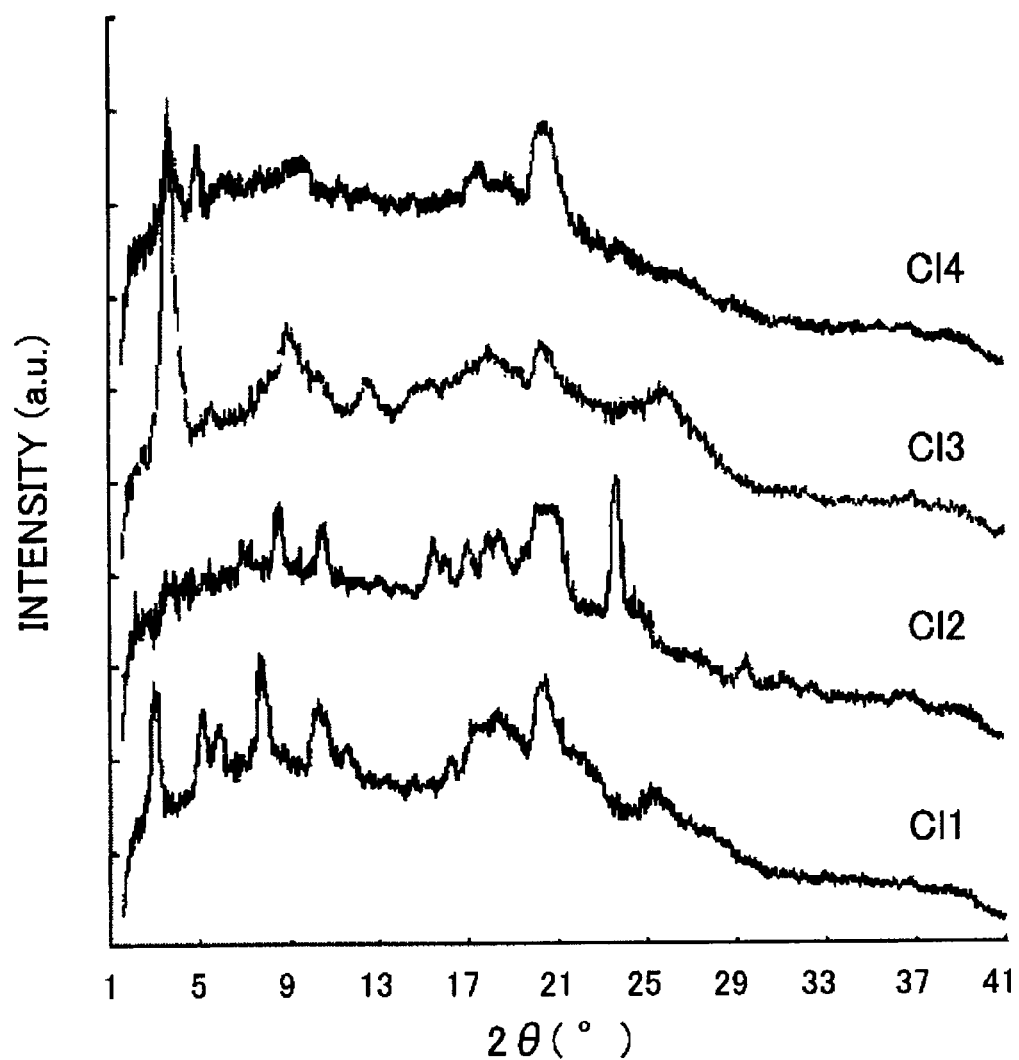
FIG. 7 shows each powder X-ray diffraction pattern of crystal form Cl1 to crystal form Cl4 of a hydrochloride salt of the compound of the formula (I) of the present invention.

The powder X-ray diffraction pattern of each crystal thus obtained was measured. FIG. 7 shows the result thereof.

EXAMPLE 7

Preparation of Crystal Form Su1 to Crystal Form Su3)

A sulfuric acid aqueous solution was added to the compound (free form) of the formula (I) prepared in Process 1 of Example 1 so that the molar ratio of a sulfuric acid to said compound becomes 1.1:1, and then water was evaporated. The sulfate salt thus obtained was added to pyridine to become the free form equivalent to 75 mg/1 mL in pyridine, put in 1 well of a 96-well plate and dissolved by being heated up to 60° C. Then, the reactant was slowly cooled down to 5° C. (at a cooling rate of 1° C./hour), aged at the same temperature for about 72 hours, and then the precipitated crystal form Su1 was collected.

Crystal form Su2 and crystal form Su3 were obtained by the same method as mentioned above provided that the following condition was changed:

Crystal form Su2: use of nitromethane as the solvent, and about 1 hour of aging time Crystal form Su3: use of ethanol as the solvent, and about 1 hour of aging time.

Figure 8:
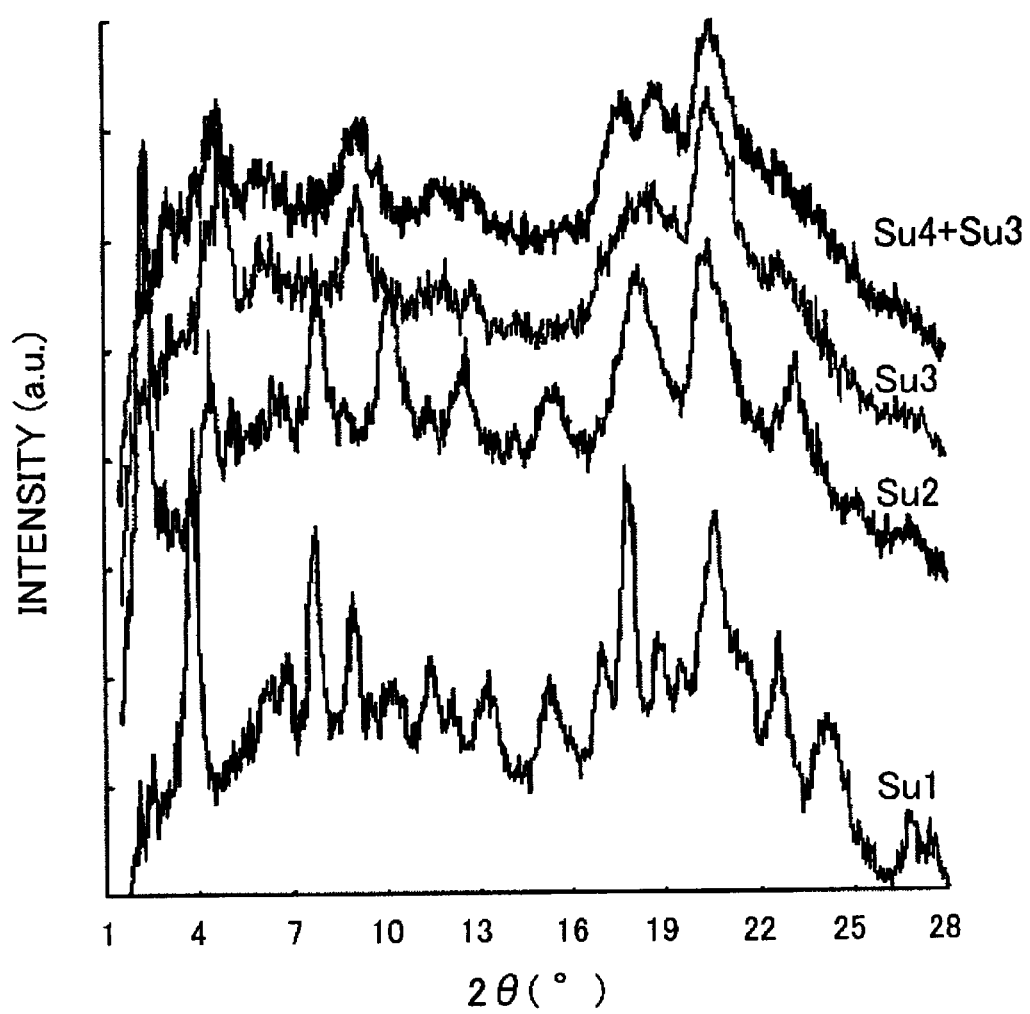
FIG. 8 shows each powder X-ray diffraction pattern of crystal form Su1 to crystal form Su3 of a sulfate salt of the compound of the formula (I) of the present invention.

The powder X-ray diffraction pattern of each crystal thus obtained was measured. FIG. 8 shows the result thereof.

EXAMPLE 8

Preparation of Crystal Form Br1 to Crystal Form Br5)

Cyclohexanone comprising a hydrogen bromide of which molar ratio to the compound of the formula (I) (free form) prepared in Process 1 of Example 1 becomes 1.1:1 was added to said compound so that the concentration becomes the free form equivalent to 75 mg/1 mL in cycloheanone. The mixture was put in 1 well of a 96-well plate and dissolved by being heated up to 60° C. Then, the reactant was slowly cooled down to 5° C. (at a cooling rate of 1° C./hour), aged at the same temperature for about 72 hours, and then the precipitated crystal form Br1 was collected.

Crystal form Br2 to crystal form Br5 were obtained by the same method as mentioned above provided that the following condition was changed:

Crystal form Br2: use of ethanol as the solvent

Crystal form Br3: use of acetonitrile as the solvent, and about 1 hour of aging time Crystal form Br4: use of tetrahydrofuran (THF) as the solvent Crystal form Br5: use of 1,2-dimethoxyethane as the solvent.

Figure 9:
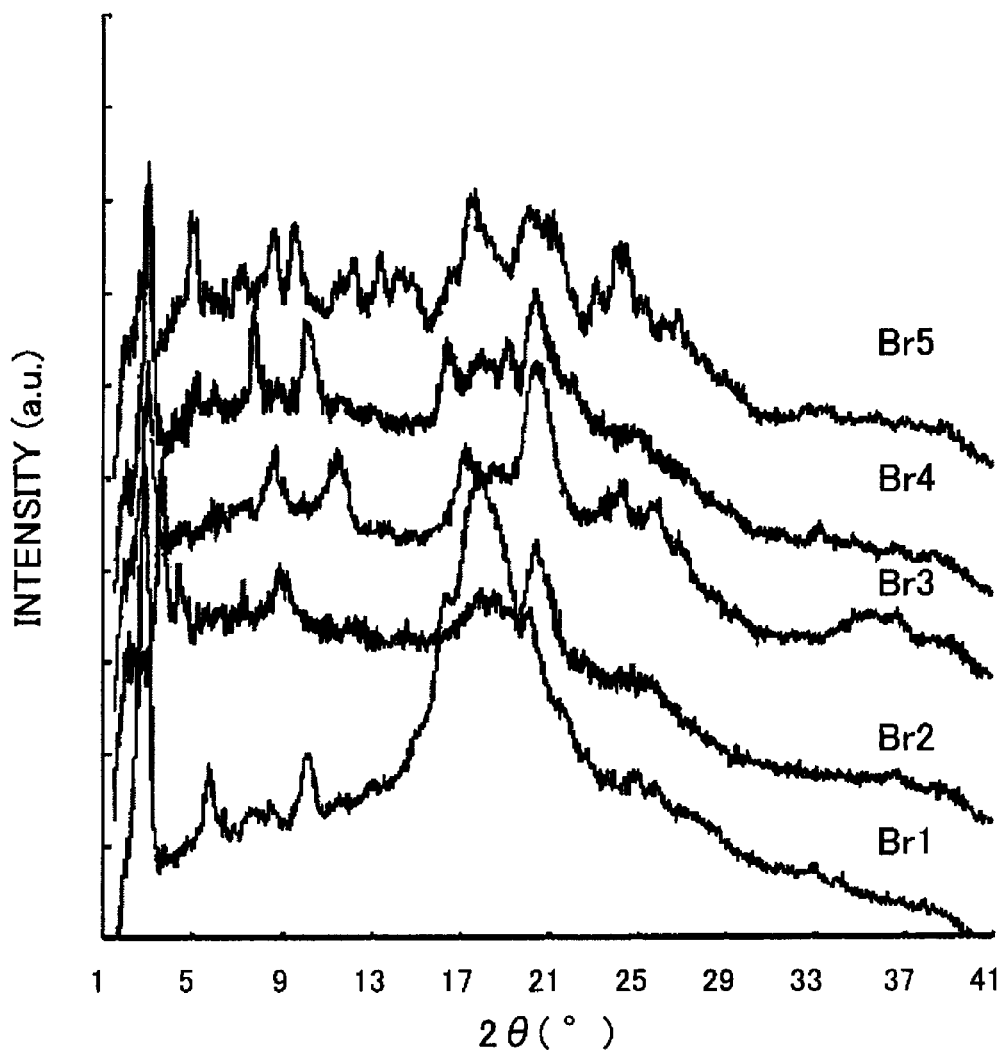
FIG. 9 shows each powder X-ray diffraction pattern of crystal form Br1 to crystal form Br5 of a hydrobromide salt of the compound of the formula (I) of the present invention.

The powder X-ray diffraction pattern of each crystal thus obtained was measured. FIG. 9 shows the result thereof.

EXAMPLE 9

Preparation of Crystal Form Pho1 to Crystal Form Pho4

A phosphoric acid aqueous solution was added to the compound (free form) of the formula (I) prepared in Process 1 of Example 1 so that the molar ratio of a phosphoric acid to said compound becomes 1.1:1, and then water was evaporated. The phosphate salt thus obtained was added to cyclohexanone to become the free form equivalent to 75 mg/1 mL in cyclohexanone, put in 1 well of a 96-well plate and dissolved by being heated up to 60° C. Then, the reactant was slowly cooled down to 5° C. (at a cooling rate of 1° C./hour), aged at the same temperature for about 1 hour, and then the precipitated crystal form Pho1 was collected.

Crystal form Pho2 to crystal form Pho4 were obtained by the same method as mentioned above provided that the following condition was changed:

Crystal form Pho2: use of water as the solvent

Crystal form Pho3: use of methanol as the solvent

Crystal form Pho4: use of 2,2,2-trifluoroethanol as the solvent.

Figure 11:
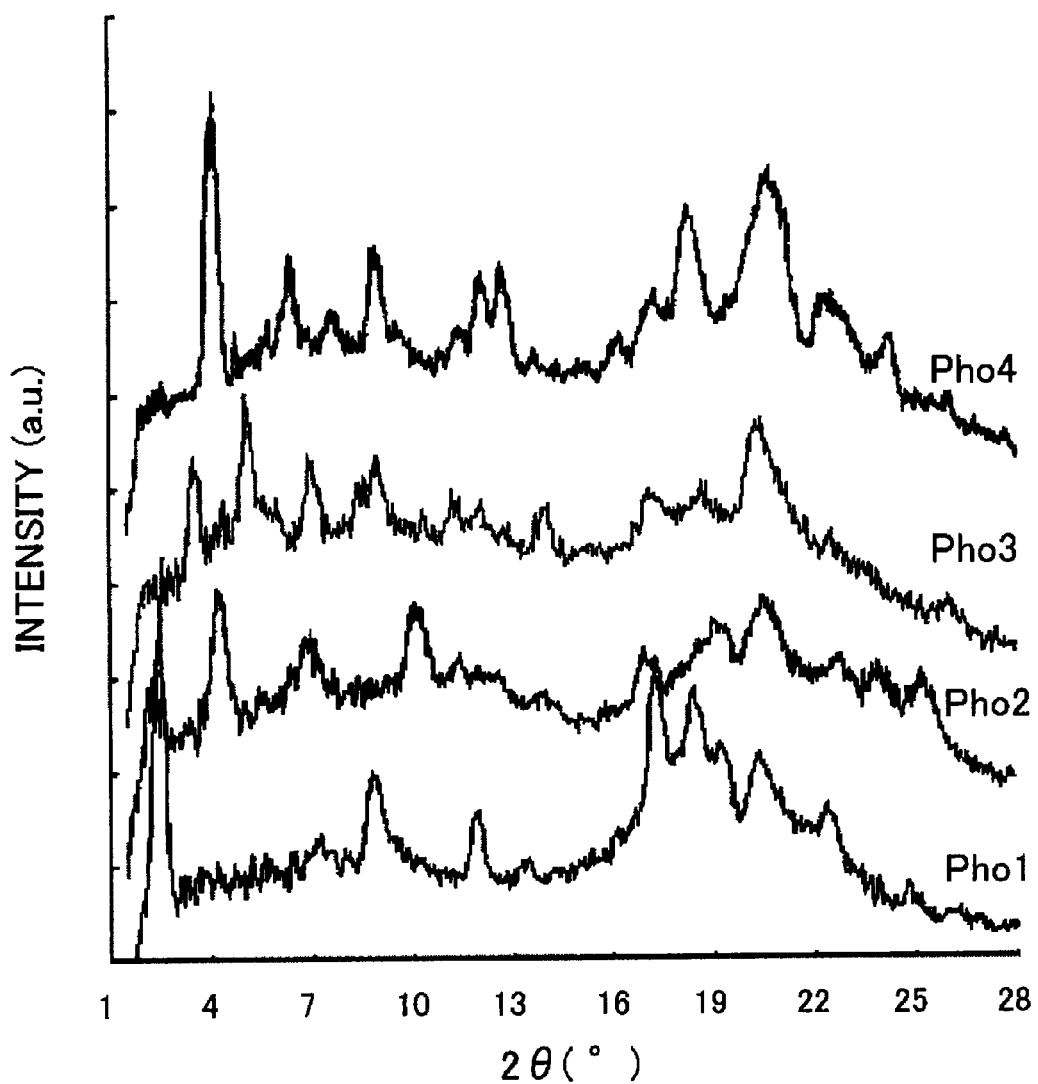
FIG. 11 shows each powder X-ray diffraction pattern of crystal form Pho1 to crystal form Pho4 of a phosphate salt of the compound of the formula (I) of the present invention.

The powder X-ray diffraction pattern of each crystal thus obtained was measured. FIG. 11 shows the result thereof.

EXAMPLE 10

Preparation of Crystal Form Mal1 to Crystal Form Mal3

A maleic acid aqueous solution was added to the compound (free form) of the formula (I) prepared in Process 1 of Example 1 so that the molar ratio of a maleic acid to said compound becomes 1.1:1, and then water was evaporated. The maleate salt thus obtained was added to ethanol to become the free form equivalent to 75 mg/1 mL in ethanol, put in 1 well of a 96-well plate and dissolved by being heated up to 60° C. Then, the reactant was slowly cooled down to 5° C. (at a cooling rate of 1° C./hour), aged at the same temperature for about 1 hour, and then the precipitated crystal form Mal1 was collected.

Crystal form Mal2 and crystal form Mal3 were obtained by the same method as mentioned above provided that the following condition was changed:

Crystal form Mal2: use of ethyl acetate as the solvent

Crystal form Mal3: use of acetone as the solvent.

Figure 12:
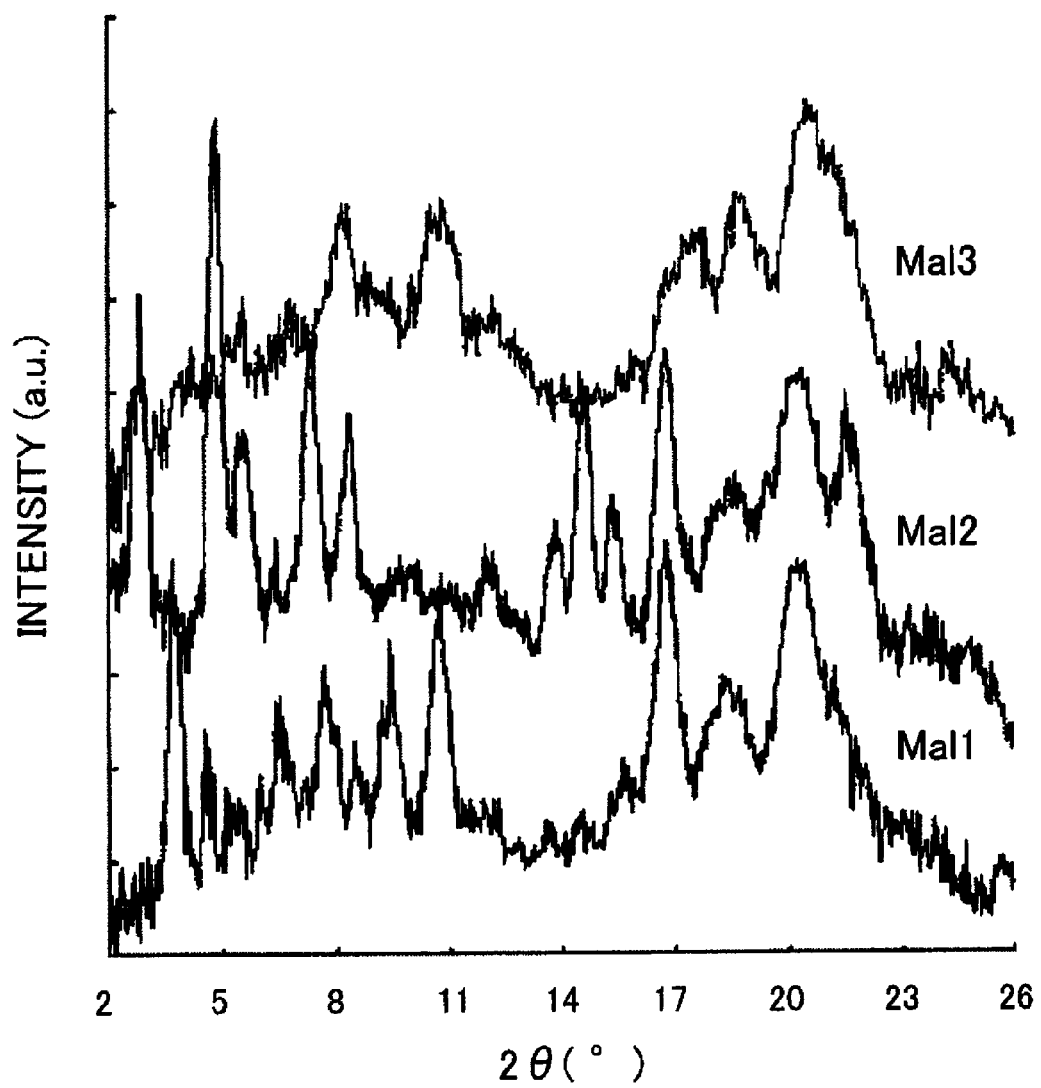
FIG. 12 shows each powder X-ray diffraction pattern of crystal form Mal1 to crystal form Mal3 of a maleate salt of the compound of the formula (I) of the present invention.

The powder X-ray diffraction pattern of each crystal thus obtained was measured. FIG. 12 shows the result thereof.

EXAMPLE 11

Preparation of Crystal Form Aca1 to Crystal Form Aca3

Acetone comprising an acetic acid of which molar ratio to the compound (free form) of the formula (I) prepared in Process 1 of Example 1 becomes 1.1:1 was added to said compound so that the concentration becomes the free form equivalent to 75 mg/1 mL in acetone. The mixture was put in 1 well of a 96-well plate and dissolved by being heated up to 60° C. Then, the reactant was slowly cooled down to 5° C. (at a cooling rate of 1° C./hour), aged at the same temperature for about 1 hour, and then the precipitated crystal form Aca1 was collected.

Crystal form Aca2 and crystal form Aca3 were obtained by the same method as mentioned above provided that the following condition was changed:

Crystal form Aca2: use of 2-butanol as the solvent

Crystal form Aca3: use of ethyl acetate as the solvent.

Figure 13:
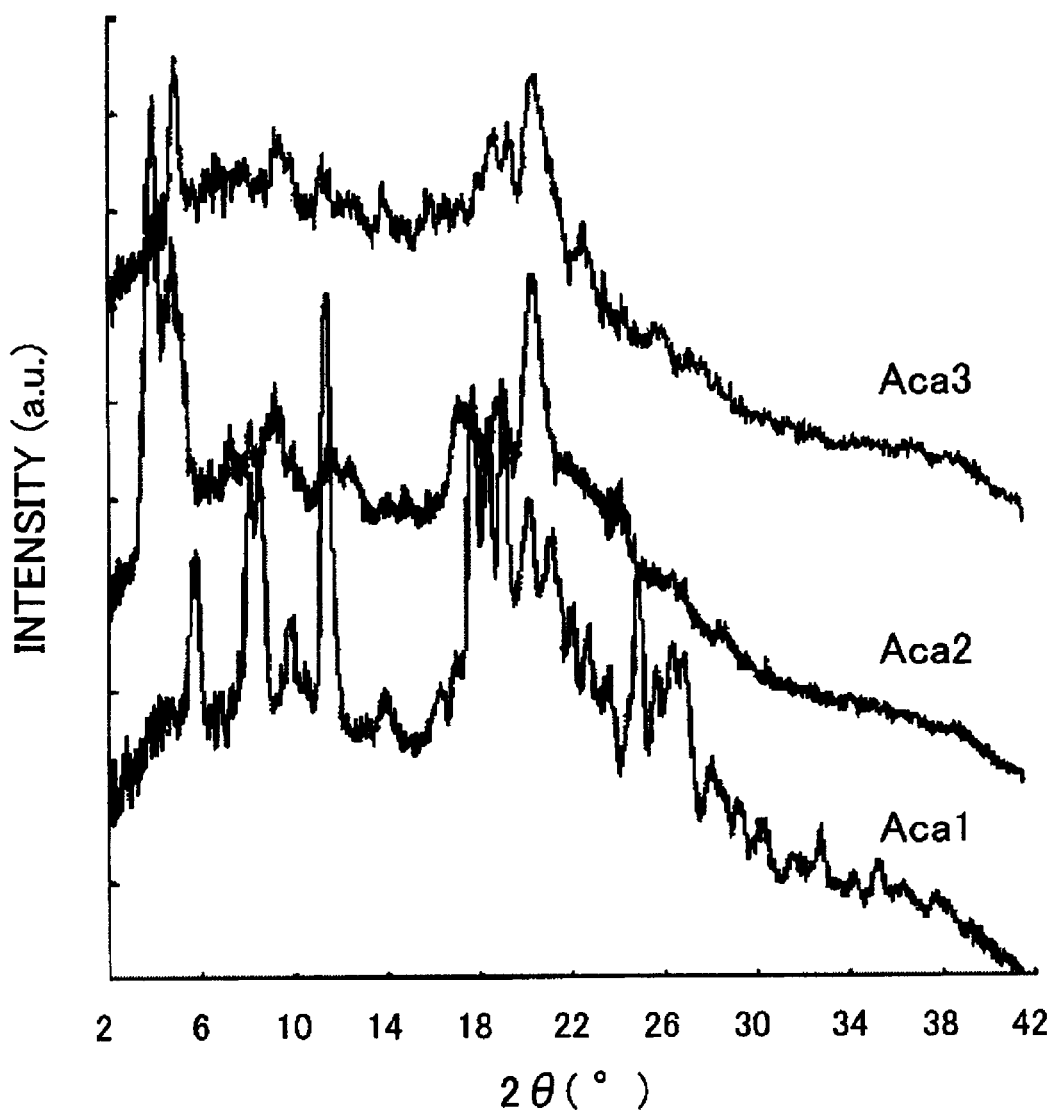
FIG. 13 shows each powder X-ray diffraction pattern of crystal form Aca1 to crystal form Aca3 of an acetate salt of the compound of the formula (I) of the present invention.

The powder X-ray diffraction pattern of each crystal thus obtained was measured. FIG. 13 shows the result thereof.

EXAMPLE 12

Preparation of Crystal Form Tar1 and Crystal Form Tar2

A D-tartaric acid aqueous solution was added to the compound (free form) of the formula (I) prepared in Process 1 of Example 1 so that the molar ratio of a D-tartaric acid to said compound becomes 1.1:1, and then water was evaporated. The D-tartrate salt thus obtained was added to cyclohexanone to become the free form equivalent to 75 mg/1 mL in cyclohexanone, put in 1 well of a 96-well plate and dissolved by being heated up to 60° C. Then, the reactant was slowly cooled down to 5° C. (at a cooling rate of 1° C./hour), aged at the same temperature for about 1 hour, and then the precipitated crystal form Tar1 was collected.

Crystal form Tar2 was obtained by the same method as mentioned above provided that the following condition was changed:

Crystal form Tar2: use of methanol as the solvent.

Figure 14:
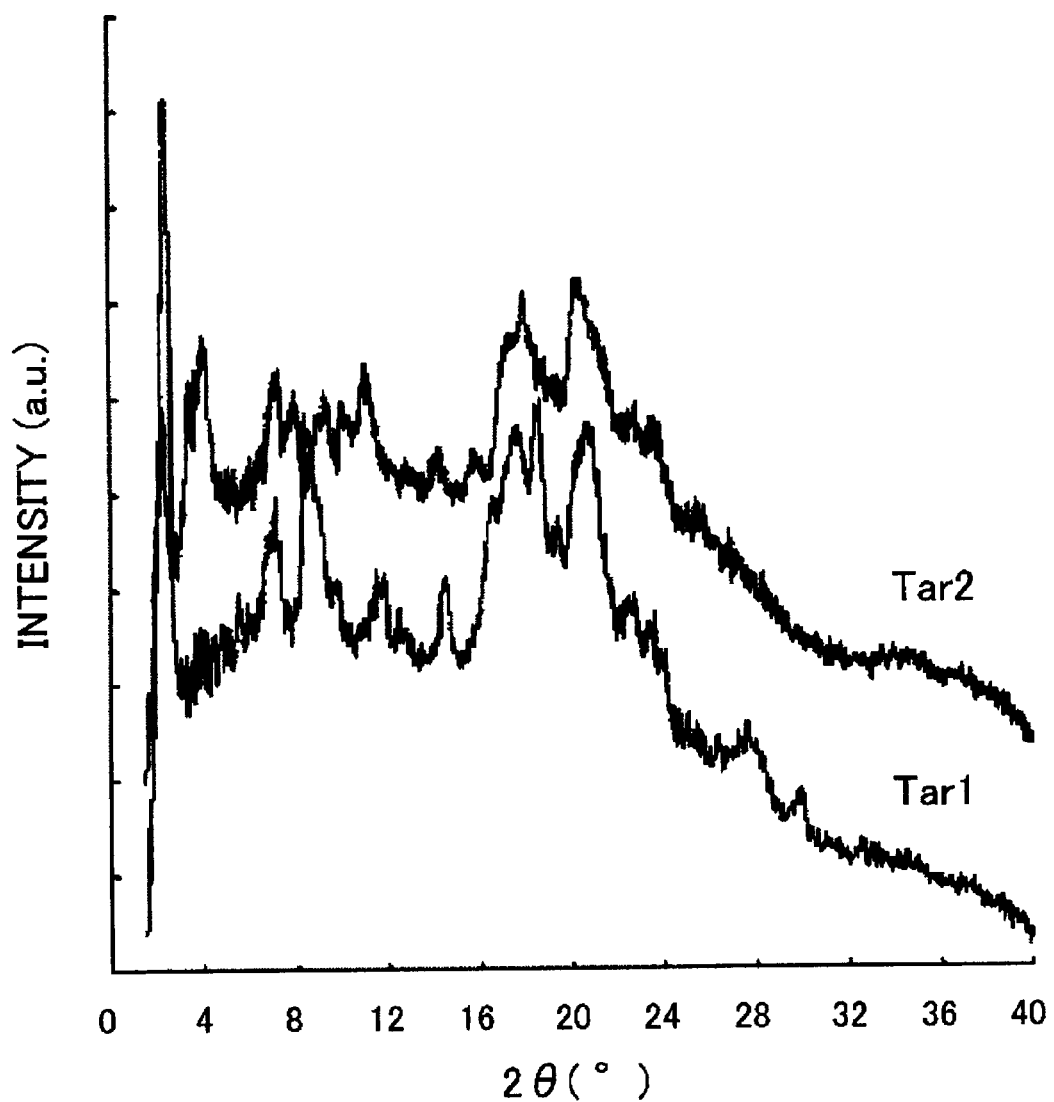
FIG. 14 shows each powder X-ray diffraction pattern of crystal form Tar1 and crystal form Tar2 of a tartrate salt of the compound of the formula (I) of the present invention.

The powder X-ray diffraction pattern of each crystal thus obtained was measured. FIG. 14 shows the result thereof.

EXAMPLE 13

Preparation of Crystal Form Cl1

An acetone solution (11.0 mL, 0.140 mmol) to which a 37% hydrochloric acid was added in order to comprise 0.14 mmol/mL of a hydrogen chloride was added to 76 mg (0.127 mmol) of the compound (free form) of the formula (I) prepared in the referential example (the molar ratio of said compound to a hydrogen chloride=1:1.1). Stirring the mixture by a magnetic stir bar, it was heated at a heating rate of 1° C./minute, and kept at 60° C. for 30 minutes. Then, the reactant was slowly cooled down to 5° C. (at a cooling rate of 1° C./hour), aged at the same temperature for about 72 hours, and then the precipitated crystal form Cl1 was collected.

When measuring the powder X-ray diffraction pattern of the crystal thus obtained, the pattern was the same as that of crystal form Cl1 in FIG. 7.

EXAMPLE 14

Preparation of Crystal Form Br4 [Scale-Up]

A THF solution (1.1 mL, 0.154 mmol) to which a 48% hydrobromic acid was added in order to comprise 0.14 mmol/mL of HBr was added to 82.7 mg (0.139 mmol) of the compound (free form) of the formula (I) prepared in the referential example (the molar ratio of said compound to HBr=1:1.1). Stirring the mixture by a magnetic stir bar, it was heated at a heating rate of 1° C./minute, and kept at 60° C. for 30 minutes to dissolve a hydrobromide salt. Then, the reactant was slowly cooled down to 5° C. (at a cooling rate of 1° C./hour), aged at the same temperature for about 72 hours, and then the precipitated crystal form Br4 was collected.

When measuring the powder X-ray diffraction pattern of the crystal thus obtained, the pattern was the same as that of crystal form Br4 obtained in Example 8.

EXAMPLE 15

Preparation of Crystal Form Mal2 [Scale-Up]

A solution (0.140 mmol) wherein 16.3 mg of a maleic acid (purity: 99%) was dissolved in 1.004 mL of ethyl acetate was added to 75.3 mg (0.126 mmol) of the compound (free form) of the formula (I) prepared in the referential example (the molar ratio of said compound to a maleic acid=1:1.1). Stirring the mixture by a magnetic stir bar, it was heated at a heating rate of 1° C./minute, and kept at 60° C. for 30 minutes to dissolve a maleate salt. Then, the reactant was slowly cooled down to 5° C. (at a cooling rate of 1° C./hour), aged at the same temperature for about 72 hours, and then the precipitated crystal form Mal2 was collected.

When measuring the powder X-ray diffraction pattern of the crystal thus obtained, the pattern was the same as that of crystal form Mal2 obtained in Example 10.

Measurement Method 2 Powder X-Ray Diffraction Measurement

The Measurement Condition of the Powder X-Ray Diffraction Pattern described in Examples 16 to 18 and 24 is as follows:

| Device: | Powder X-ray diffractometer, X'Pert-Pro-MPD (PANalytical) |
|---|---|
| Detector: | Semiconductor array detector, X'Celerator |
| Target: | Cu fully automatic monochromator |
| Voltage: | 40 kV |
| Current: | 40 mV |
| Slit: | divergence 1/2° |
| | scattering 1/2° |
| | light-receiving 0.15 mm |
| Scan Speed: | 2°/min. |
| 2θ range: | 3 to 30° |

EXAMPLE 16

Synthesis of Crystal Form Mal2, Scale-Up

A maleic acid was dissolved in ethyl acetate to become 0.14 mmol/mL. 10 mL thereof was added to the compound (I) (750 mg, 1.25 mmol) prepared in the referential example, and the mixture was heated up from 20° C. to 60° C. with stirring it (at a heating rate of 1° C./min.) The reactant was kept at 60° C. for 30 minutes and cooled down from 60° C. to 5° C. for 55 hours (at a cooling rate of 1° C./hour). Then, it was aged at 5° C. for about 14 hours, filtered and dried under reduced pressure (at room temperature for 24 hours) to obtain a white crystal.

Figure 15:
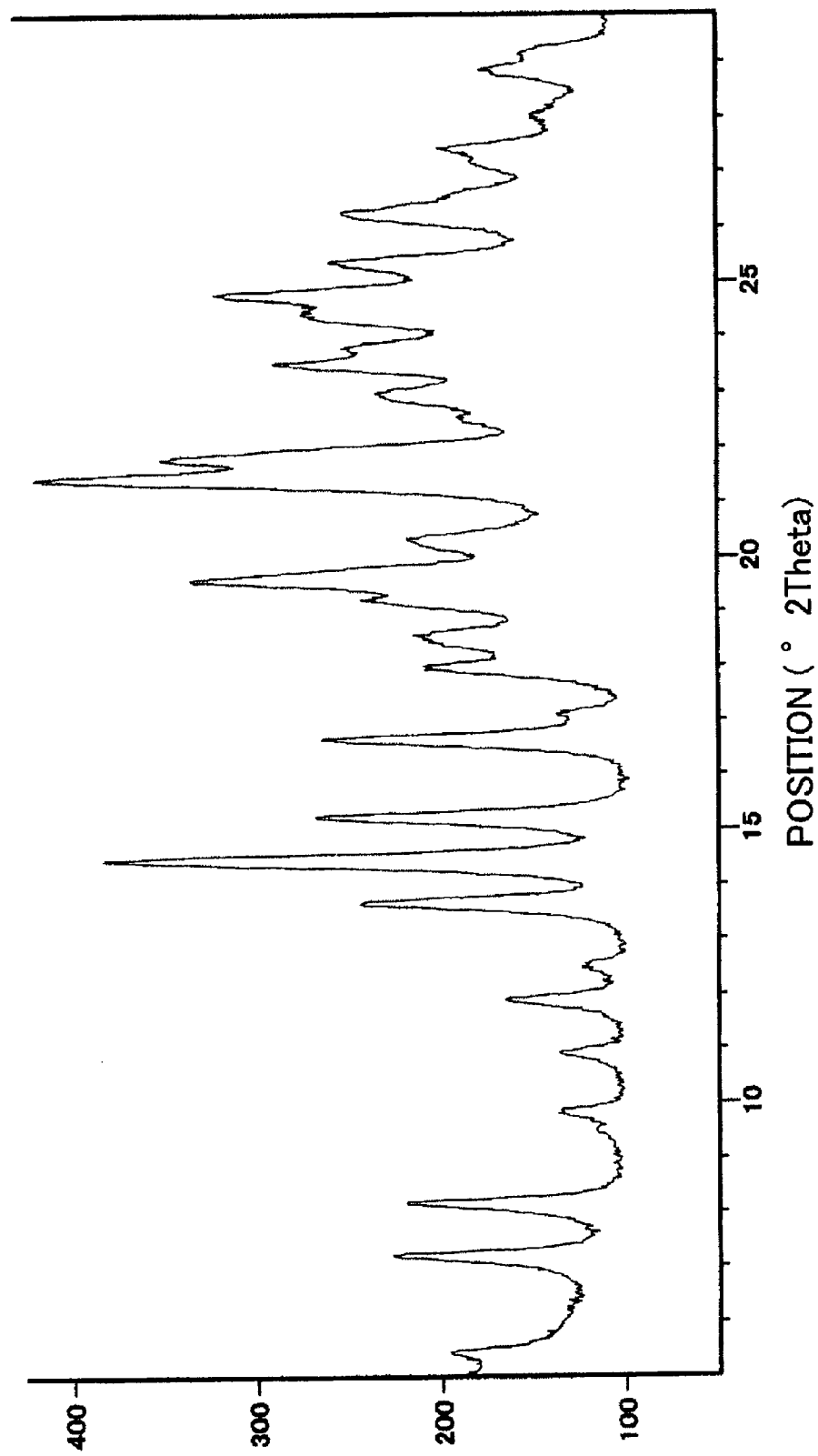
FIG. 15 shows a powder X-ray diffraction pattern diagram on crystal form Mal2 of a maleate salt of the compound of the formula (I) of the present invention (horizontal axis: diffraction angle 2θ [°]; vertical axis: intensity [CPS]).

Powder X-Ray Diffraction Pattern: FIG. 15

$^1$H-NMR (DMSO-d$_6$): δ 1.18 (3H, d, J=6.3 Hz), 1.23 (3H, d, J=6.3 Hz), 2.58 (3H, s), 3.02 (1H, dd, J=14.1, 9.9 Hz), 3.19 (1H, dd, J=14.1, 5.4 Hz), 3.55 (3H, s), 4.24 (2H, s), 4.72-4.82 (1H, m), 4.90-5.00 (1H, m), 6.02 (2H, s), 7.21 (2H, d, J=8.4 Hz), 7.39-7.48 (5H, m), 7.59 (1H, d, J=8.7 Hz), 7.87 (1H, dd, J=9.0, 2.4 Hz), 8.24 (1H, d, J=2.4 Hz), 8.68-8.80 (brs, 1H), 9.24 (1H, d, J=8.1 Hz).

EXAMPLE 17

Preparation of Crystal Form Cl5

(Method Wherein a Tetrahydrofuran Solvent is Used: Production Method 1)

A hydrochloric acid was diluted with tetrahydrofuran to become 0.14 mmol/mL. 10 mL thereof was added to the compound (I) (free form, 750 mg, 1.25 mmol) prepared in the referential example, and the mixture was heated up from 20° C. to 60° C. with stirring it (at a heating rate of 1° C./min.) The reactant was kept at 60° C. for 30 minutes and cooled down from 60° C. to 5° C. for 55 hours (at a cooling rate of 1° C./hour). Then, it was aged at 5° C. for about 14 hours, filtered and dried under reduced pressure (at room temperature for 90 hours) to obtain a white crystal (715 mg).

Figure 16:
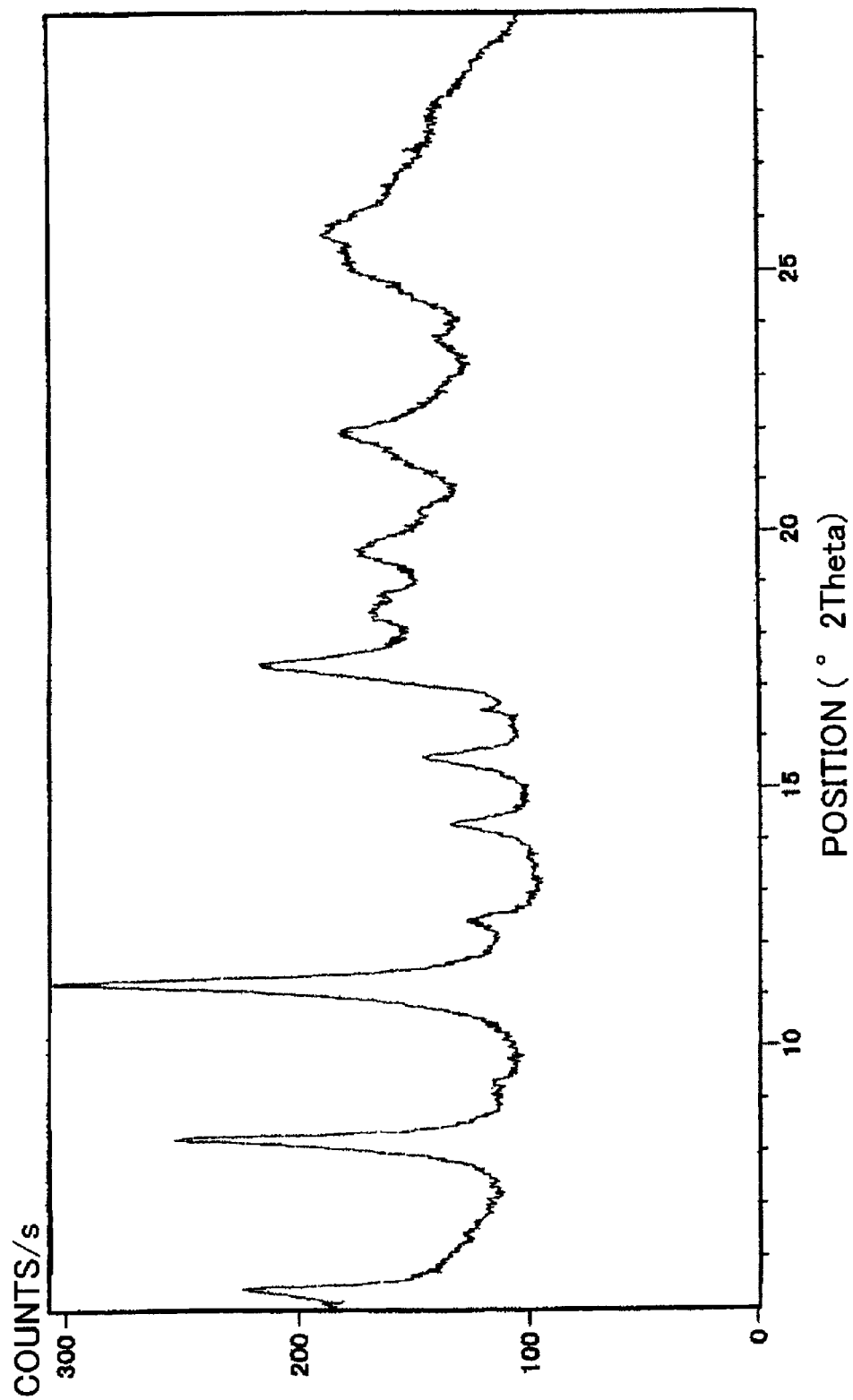
FIG. 16 shows a powder X-ray diffraction pattern diagram on crystal form Cl5 of a hydrochloride salt of the compound of the formula (I) of the present invention (horizontal axis: diffraction angle 2θ [°]; vertical axis: intensity [CPS]).

FIG. 16 shows the result of the powder X-ray diffraction pattern.

Further, the diffraction angles and intensities of main peaks are shown below:

| C15-type | |
|---|---|
| 2θ | Intensity |
| 5.4 | strong |
| 8.2 | strong |
| 11.2 | strong |
| 12.4 | weak |
| 14.3 | medium |
| 15.6 | medium |
| 17.4 | strong |
| 18.4 | weak |
| 18.8 | weak |

Among the above, particularly characteristic peaks are 8.2, 11.2, 12.4, 14.3 and 15.6, and further 8.2, 11.2, 14.3 and 15.6.

$^1$H-NMR (DMSO-$d_6$): δ 1.18 (3H, d, J=6.3 Hz), 1.23 (3H, d, J=6.3 Hz), 2.54 (3H, s), 3.02 (1H, dd, J=14.1, 9.9 Hz), 3.19 (1H, dd, J=14.1, 5.4 Hz), 3.55 (3H, s), 4.22 (2H, s), 4.70-4.82 (1H, m), 4.90-5.00 (1H, m), 7.21 (2H, d, J=8.4 Hz), 7.35-7.48 (5H, m), 7.59 (1H, d, J=8.7 Hz), 7.95 (1H, dd, J=9.0, 2.4 Hz), 8.23 (1H, d, J=2.4 Hz), 9.05-9.18 (brs, 2H), 9.24 (1H, d, J=8.1 Hz).

Method Wherein an Acetone Solvent is Used: Production Method 2)

A hydrochloric acid (5.92 mL, 71.0 mmol) was diluted with acetone (76.6 mL) to become 0.86 mmol/mL. The dilution was added to an acetone solution (433 mL) of the compound (I) (free form, 38.3 g, 64.1 mmol) prepared in the referential example, and the mixture was heated up from 20° C. to 60° C. with stirring it (at a heating rate of 1° C./min.) The reactant was kept at 60° C. for 30 minutes and cooled down from 60° C. to 5° C. for 5.5 hours (at a cooling rate of 10° C./hour). Then, it was aged at 5° C. for about 6 hours, filtered and dried under reduced pressure (at 60° C. for a few days) to obtain a white crystal (36.23 g). The powder X-ray diffraction pattern thereof represented C15-type.

(Method of Aqueous Acetone Crystallization+Poor Solvent Addition: Production Method 3)

23 mL of acetone and 15 mL of water were mixed. 5.04 g of a hydrochloride salt of the compound (I) (which is obtained, for example, by mixing the compound (I) (free form) and a dioxane solution comprising a hydrogen chloride; and then removing the solvent) was added thereto and dissolved by heating at 65° C. The dissolved solution was filtered under heating, and 220 mL of acetone was added dropwise to a filtrate for 40 minutes. 30 mg of a seed crystal was also added in said treatment. The obtained slurry was cooled down to 10° C. and stirred overnight. Then, the precipitated crystal was filtered out and washed with 30 mL of cold acetone. The obtained wet crystal was dried at 70° C. under reduced pressure to obtain 4.47 g of a white crystal (yield 88.7%). The powder X-ray diffraction pattern thereof represented C15-type.

(Method of Acetone Slurry Suspension: Production Method 4)

30.47 g of a hydrochloride salt of the compound (I) was added to 112.5 mL of acetonitrile and 37.5 mL of water and dissolved by heating at 80° C. Then, the mixture was cooled down to 30° C. and 600 mL of acetone was added dropwise. The precipitated crystal slurry was stirred at 10° C. overnight. Then, the crystal was separated by a centrifuge to obtain 61.11 g of a wet crystal. The powder X-ray diffraction pattern of this wet crystal represented NW2-type. 10.75 g of the wet crystal (dry weight 5.0 g) was suspended in 100 mL of acetone and stirred at 25° C. overnight. The crystal was filtered out and dried at 80° C. for 18 hours under reduced pressure to obtain 4.63 g of a white crystalline solid substance. The powder X-ray diffraction pattern thereof represented C15-type.

Figure 20:
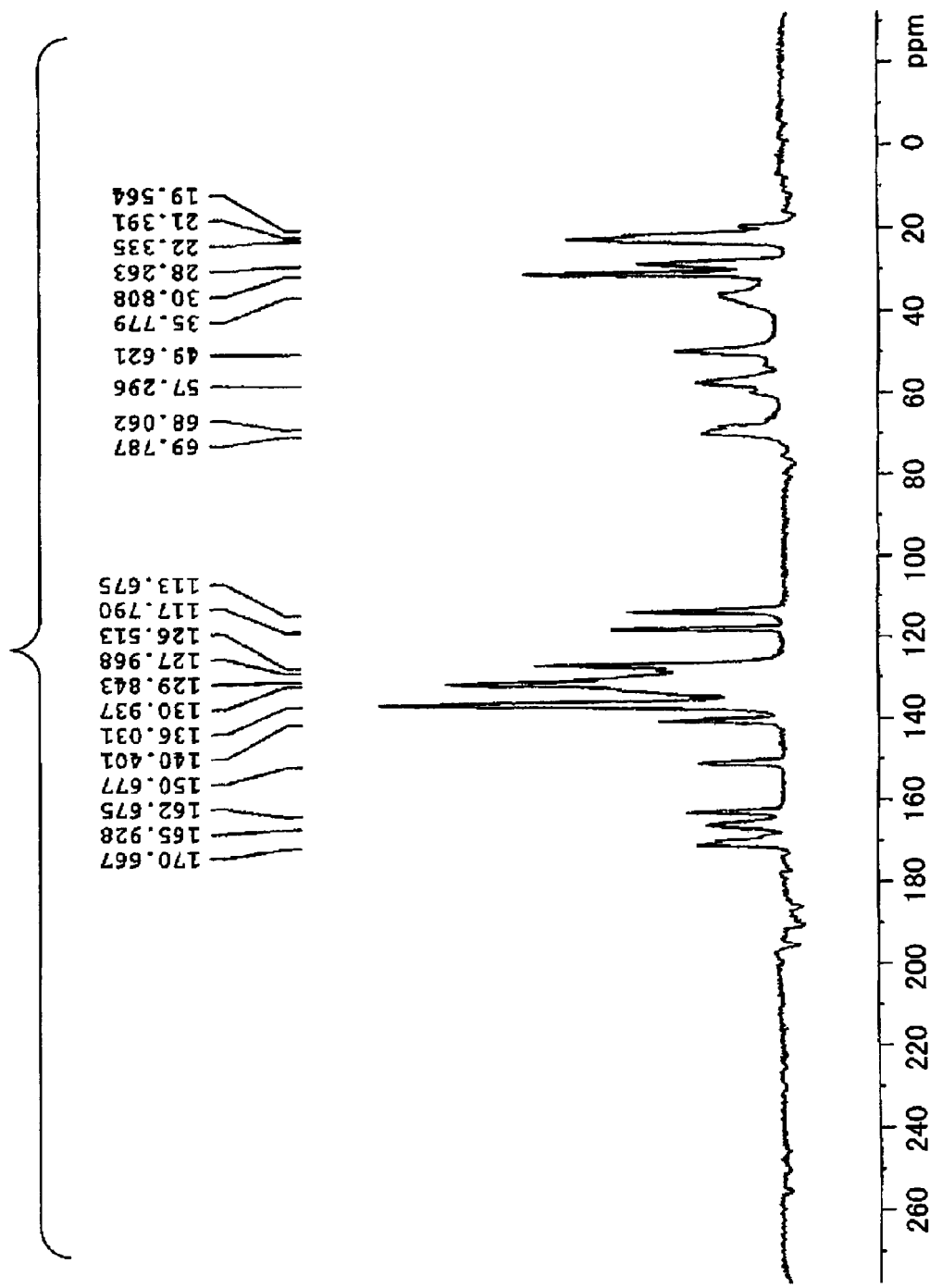
FIG. 20 shows the solid-state NMR spectrum data of crystal form Cl5 of a hydrochloride salt of the compound of the formula (I) of the present invention.
Figure 21:
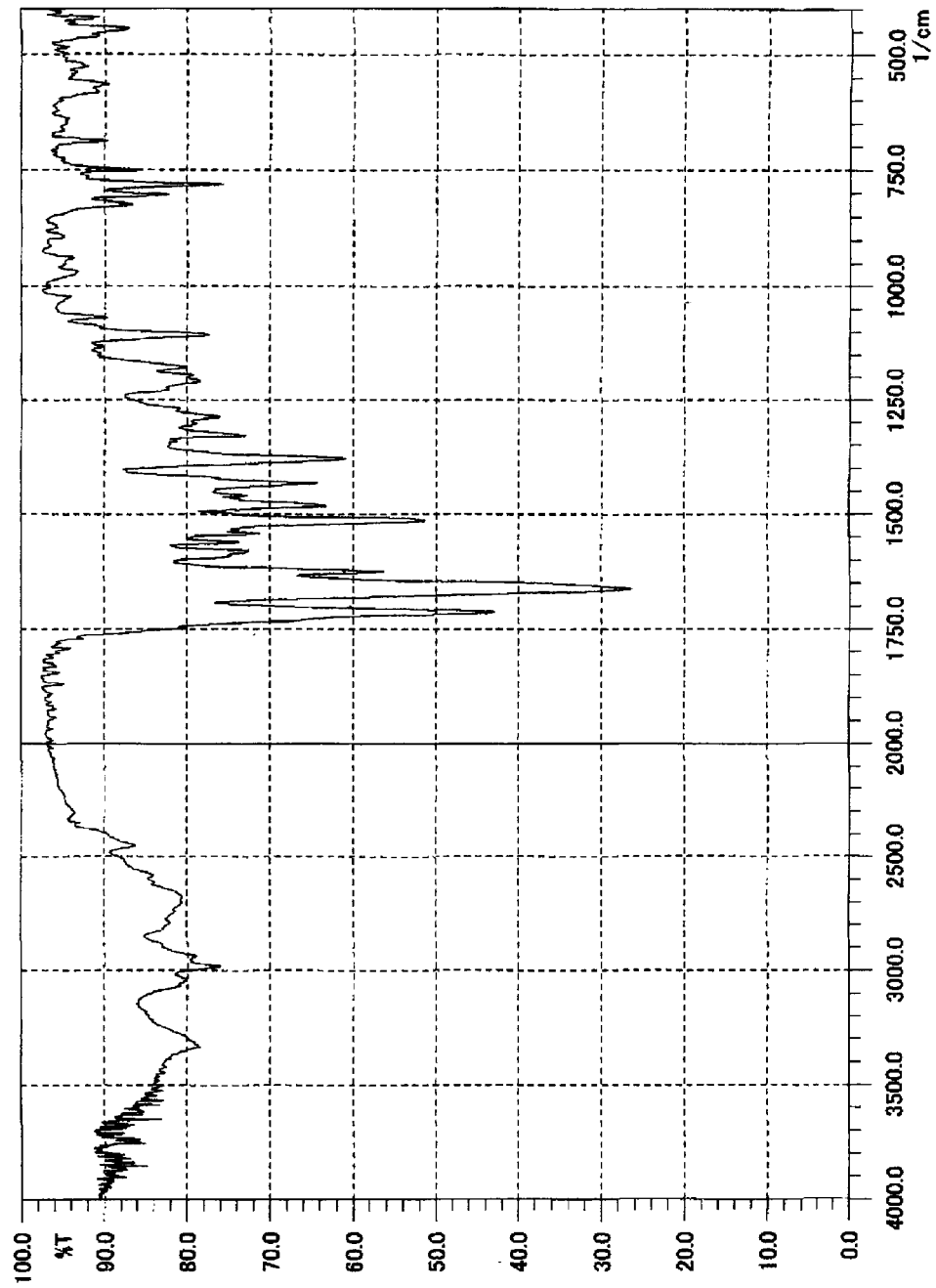
FIG. 21 shows the infrared spectrum data of crystal form Cl5 of a hydrochloride salt of the compound of the formula (I) of the present invention.

FIG. 20 shows the solid-state NMR spectrum data of crystal form C15 produced by the above method (device=AVANCE 400WB by BRUKER; measurement method=13C-CPTOSS method; MAS=6 KHz). FIG. 21 shows the infrared spectrum data of said crystal (device=FTIR-8300 by Shimadzu Corporation; measurement method=potassium chloride method).

EXAMPLE 18

Synthesis of Crystal Form Br5, Scale-Up

A hydrobromic acid was diluted with 1,2-dimethoxyethane to become 0.14 mmol/mL. 10 mL thereof was added to the compound (I) (750 mg, 1.25 mmol) prepared in the referential example, and the mixture was heated up from 20° C. to 60° C. with stirring it (at a heating rate of 1° C./min.) The reactant was kept at 60° C. for 30 minutes and cooled down from 60° C. to 5° C. for 55 hours (at a cooling rate of 1° C./hour). Then, it was aged at 5° C. for about 14 hours, filtered and dried under reduced pressure (at room temperature for 114 hours) to obtain a white crystal (803 mg).

Figure 17:
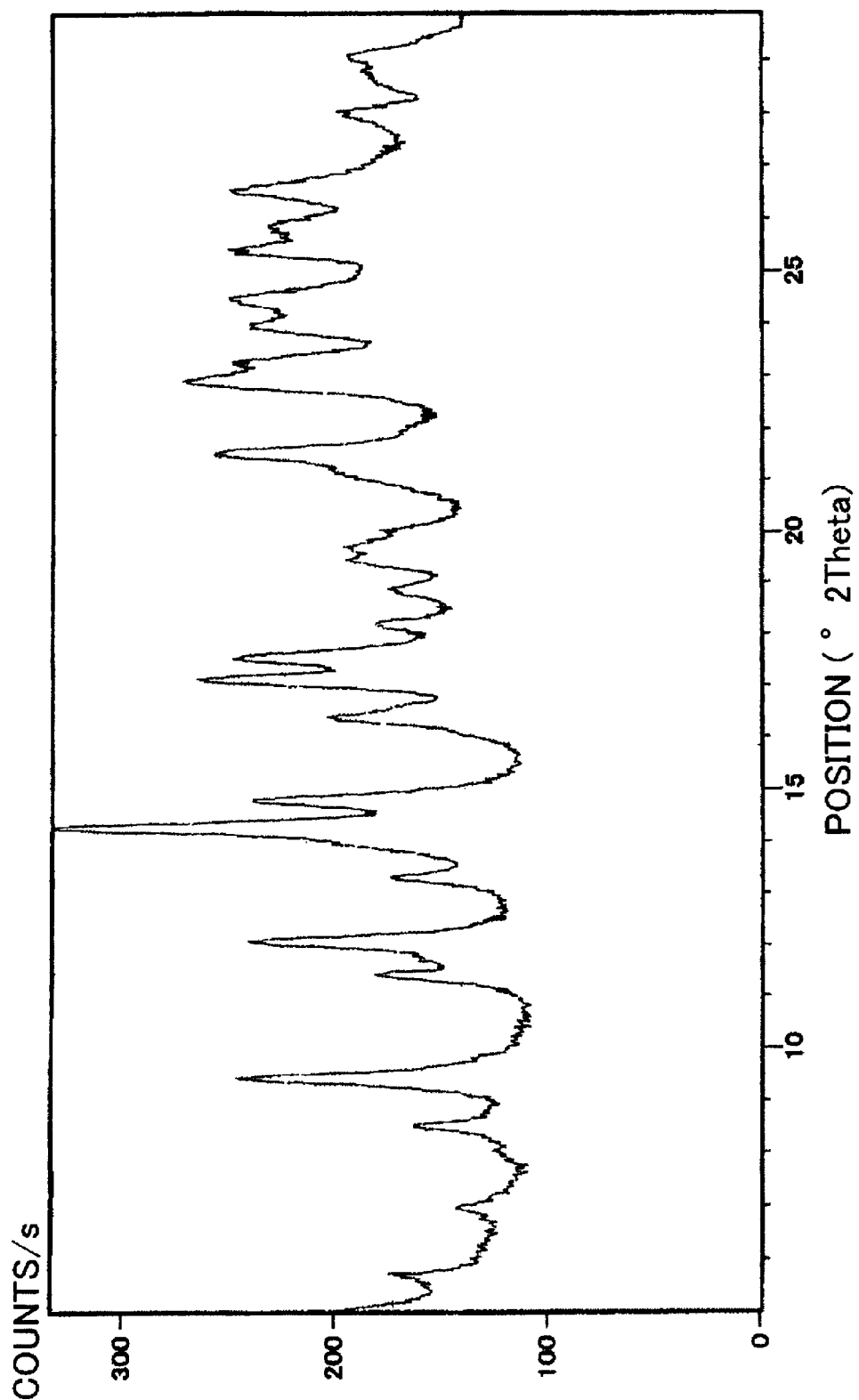
FIG. 17 shows a powder X-ray diffraction pattern diagram on crystal form Br5 of a hydrobromide salt of the compound of the formula (I) of the present invention (horizontal axis: diffraction angle 2θ [°]; vertical axis: intensity [CPS]).

Powder X-Ray Diffraction Pattern: FIG. 17

$^1$H-NMR (DMSO-$d_6$): δ 1.18 (3H, d, J=6.3 Hz), 1.23 (3H, d, J=6.3 Hz), 2.57 (3H, s), 3.02 (1H, dd, J=14.1, 9.9 Hz), 3.20 (1H, dd, J=14.1, 5.4 Hz), 3.55 (3H, s), 4.24 (2H, s), 4.70-4.82 (1H, m), 4.92-5.00 (1H, m), 7.21 (2H, d, J=8.4 Hz), 7.38-7.48 (5H, m), 7.59 (1H, d, J=8.7 Hz), 7.89 (1H, dd, J=9.0, 2.4 Hz), 8.23 (1H, d, J=2.4 Hz), 8.70-8.80 (brs, 2H), 9.24 (1H, d, J=8.1 Hz).

Measurement Method 3 Powder X-Ray Diffraction Measurement

The measurement condition of the powder X-ray diffraction pattern described in Examples 19 to 23 is as follows:

| | |
|---|---|
| Device: | Powder X-ray diffractometer, X'Pert-Pro-MPD (PANalytical) |
| Detector: | Semiconductor array detector, X'Celerator |
| Target: | Cu fully automatic monochromator |
| Voltage: | 40 kV |
| Current: | 55 mV |
| Slit: | divergence 1/2° |
| | scattering 1/2° |
| | light-receiving 0.15 mm |
| 2θ range: | 5 to 40° |

EXAMPLE 19

Preparation of Crystal Form NW1 and Crystal Form N1

20 g of a hydrochloride salt of the compound (I) was suspended in 100 mL of a mixed solution of 75 vol. % acetonitrile/water (before mixing, acetonitrile (vol): water (vol)=75:25) and heated up to 70° C. to dissolve it. This solution was cooled down to 30° C., 500 mL of acetonitrile was added dropwise and stirred at 10° C. overnight. The precipitated crystal was separated from the slurry to obtain 32.79 g of a wet crystal, which is NW1-type. This crystal was dried at 80° C. for 18 hours under reduced pressure to obtain 16.93 g of a hydrochloride salt of the compound (I) (N1-type) as a white crystalline solid substance.

Figure 22:
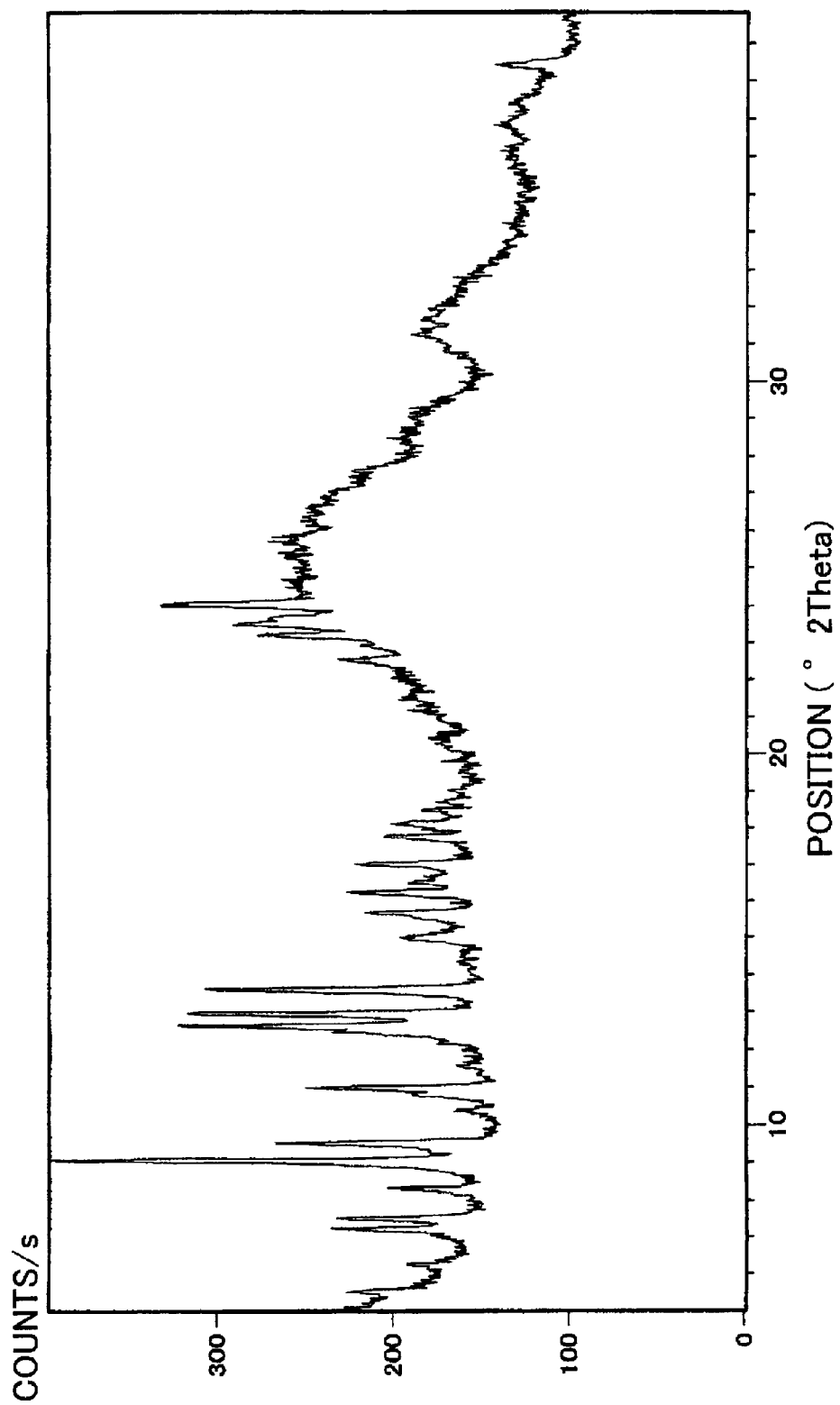
FIG. 22 shows a powder X-ray diffraction pattern of crystal form NW1 of a hydrochloride salt of the compound of the formula (I) of the present invention.
Figure 23:
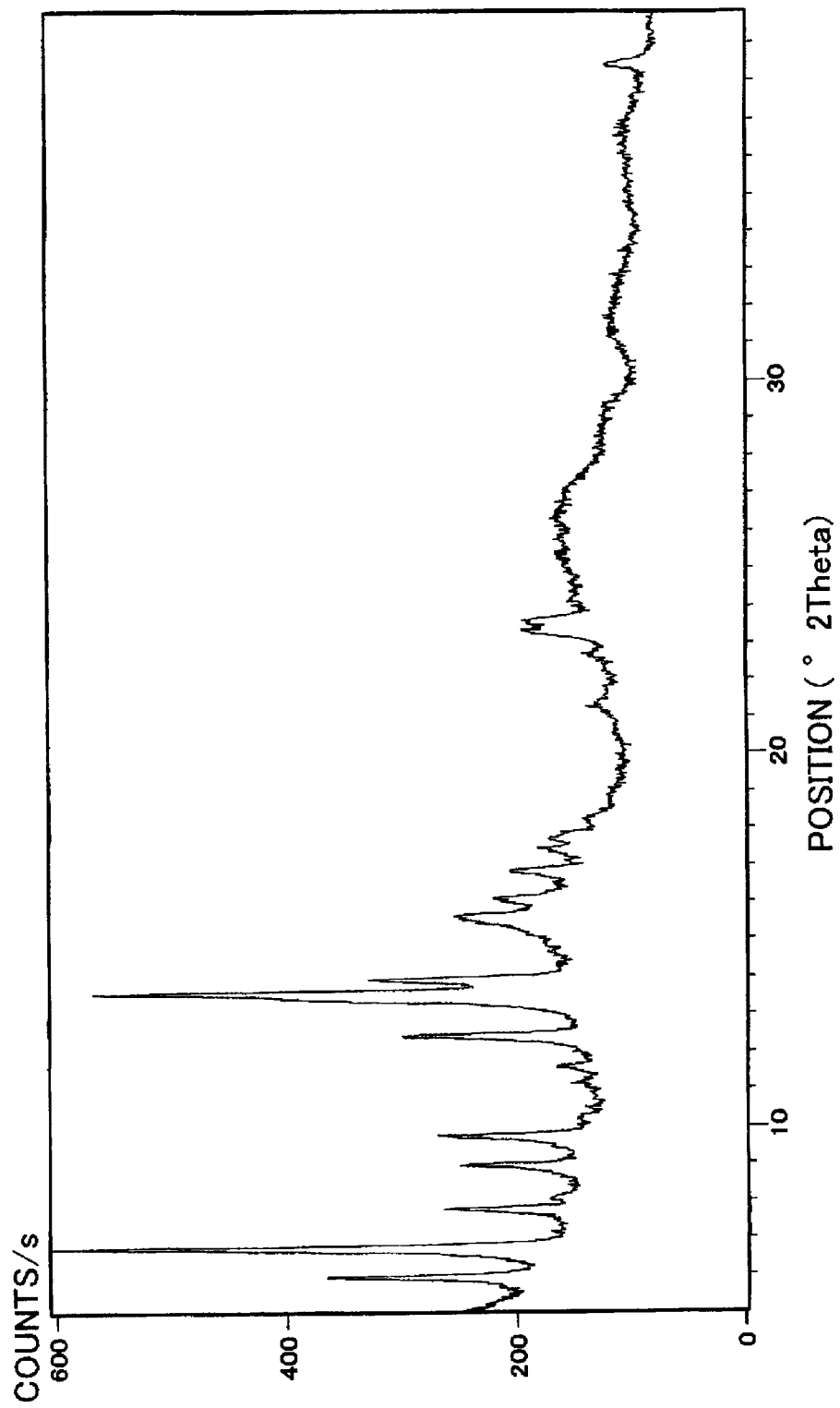
FIG. 23 shows a powder X-ray diffraction pattern of crystal form N1 of a hydrochloride salt of the compound of the formula (I) of the present invention.

Powder X-Ray Diffraction Pattern: FIGS. 22 and 23

EXAMPLE 20

Preparation of Crystal Form NW2 and Crystal Form N2

10 g of a hydrochloride salt of the compound (I) was suspended in 50 mL of a mixed solution of 75 vol. % acetonitrile/water and heated up to 70° C. to dissolve it. This solution was cooled down to 30° C., 200 mL of acetonitrile was added dropwise and stirred at 10° C. overnight. The precipitated crystal was separated from the slurry to obtain 19.20 g of a wet crystal, which is NW2-type. This crystal was dried at 80° C. for 18 hours under reduced pressure to obtain 8.77 g of a hydrochloride salt of the compound (I) (N2-type) as a white crystalline solid substance.

Figure 25:
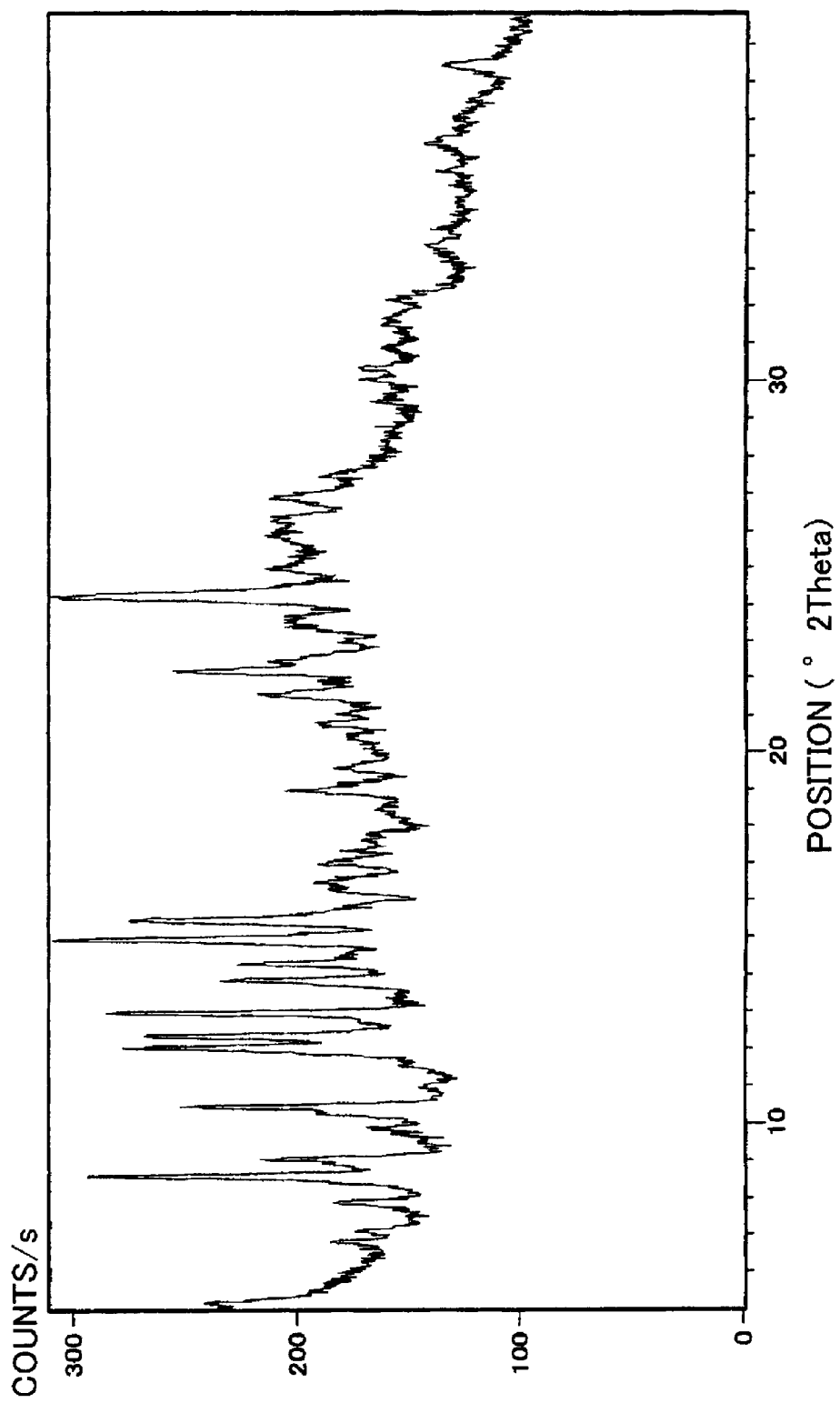
FIG. 25 shows a powder X-ray diffraction pattern of crystal form NW2 of a hydrochloride salt of the compound of the formula (I) of the present invention.
Figure 26:
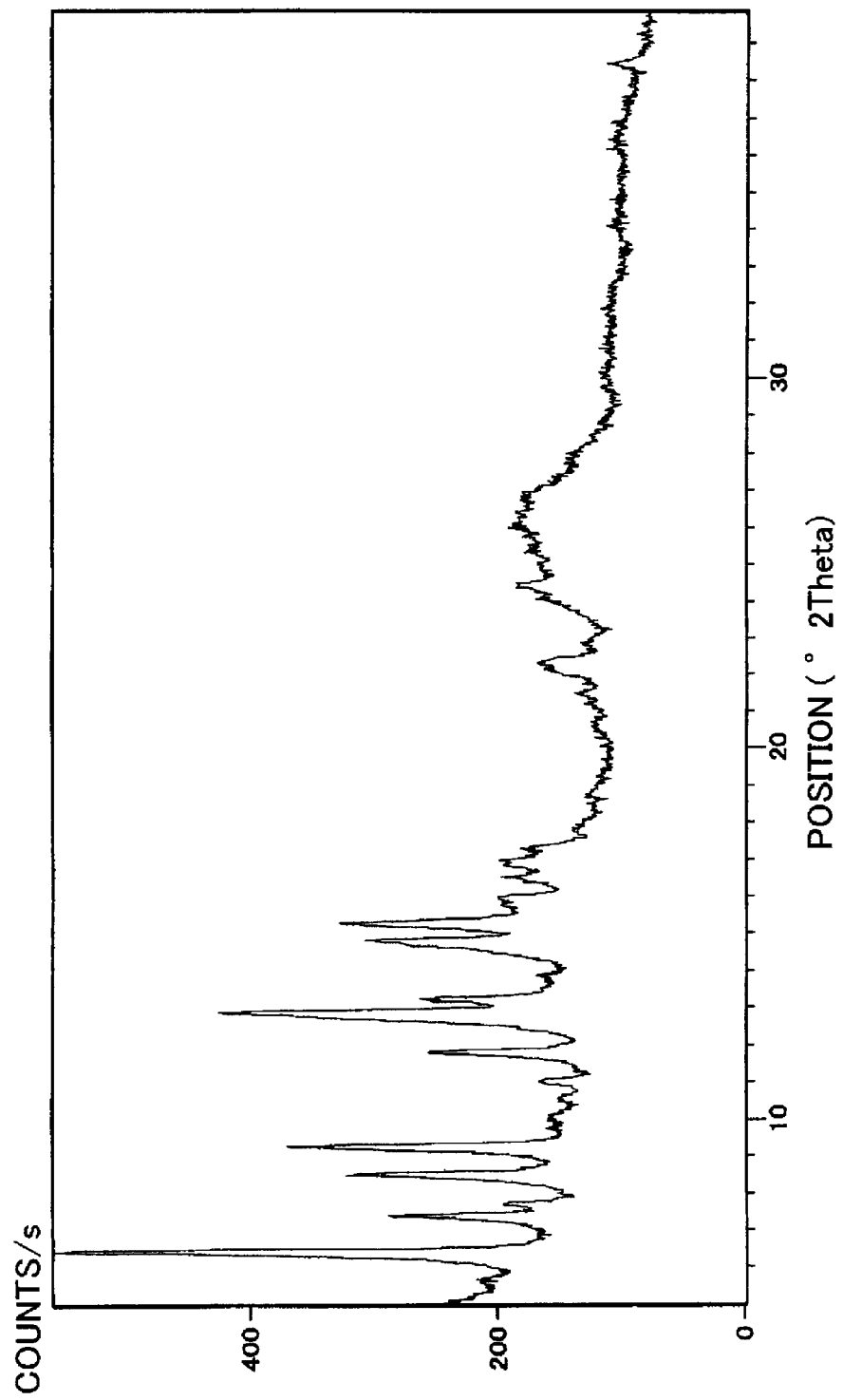
FIG. 26 shows a powder X-ray diffraction pattern of crystal form N2 of a hydrochloride salt of the compound of the formula (I) of the present invention.

Powder X-Ray Diffraction Pattern: FIGS. 25 and 26

Figure 28:
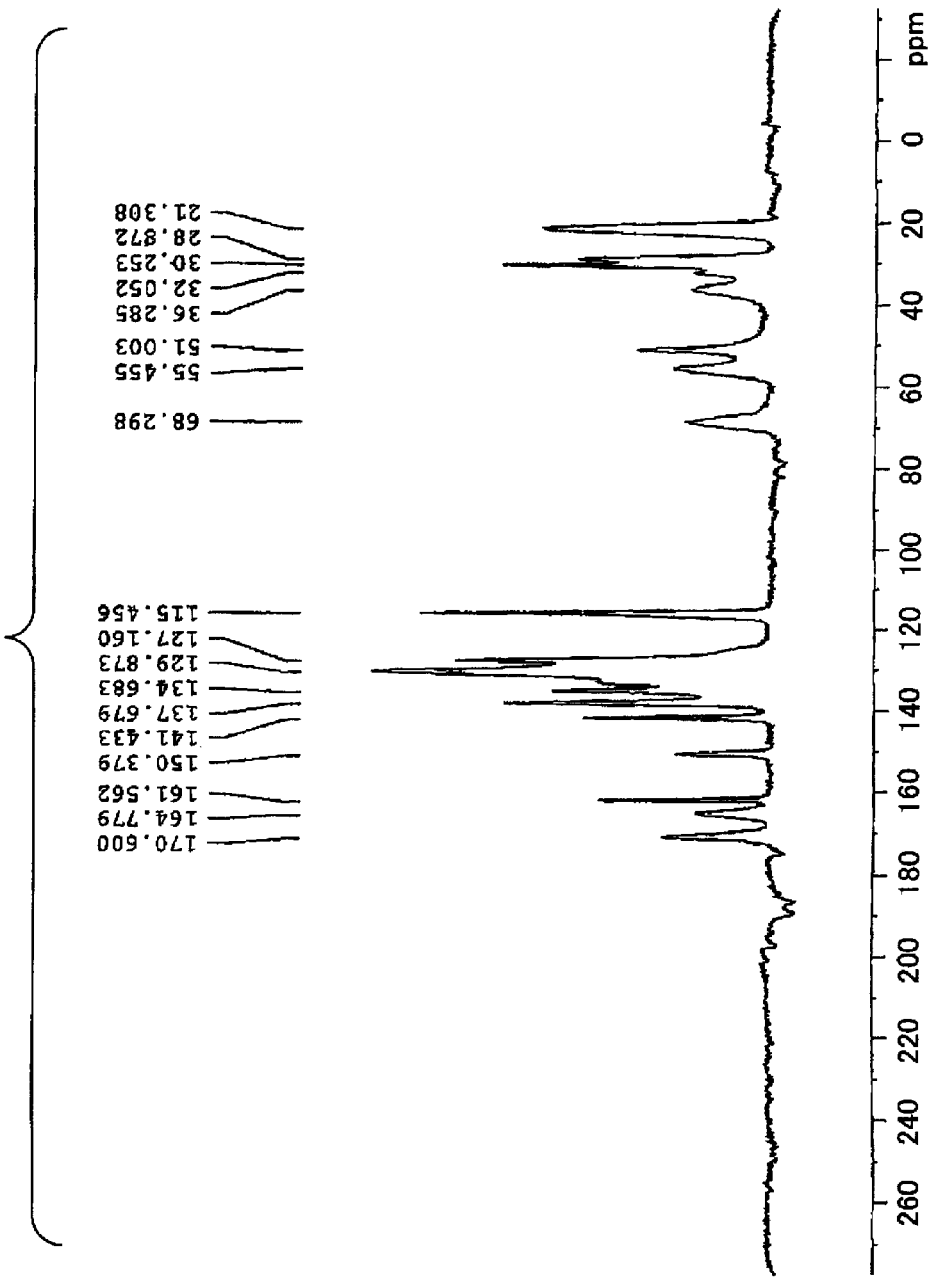
FIG. 28 shows the solid-state NMR spectrum data of crystal form N2 of a hydrochloride salt of the compound of the formula (I) of the present invention.
Figure 29:
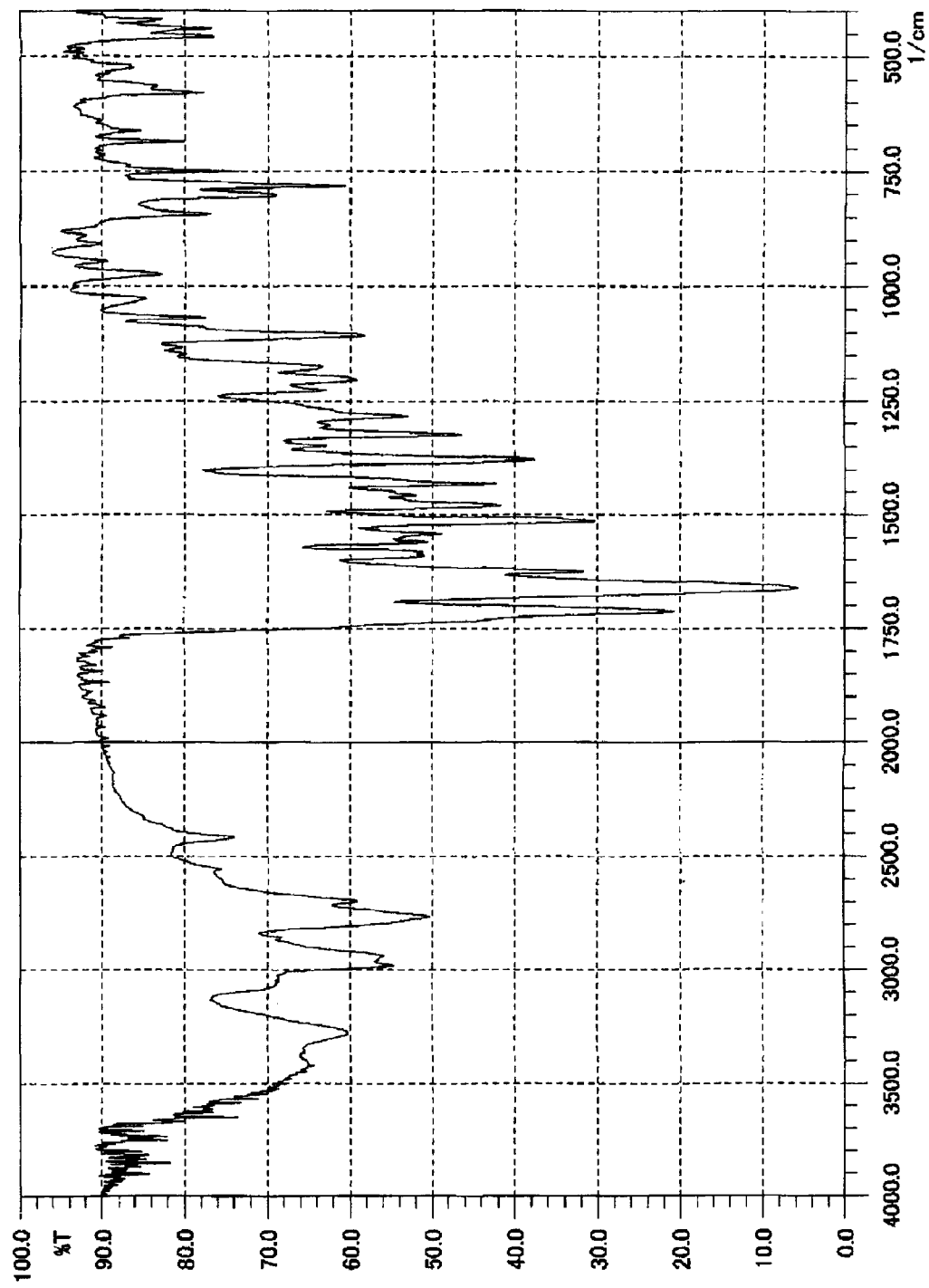
FIG. 29 shows the infrared spectrum data of crystal form N2 of a hydrochloride salt of the compound of the formula (I) of the present invention.

FIG. 28 shows the solid-state NMR spectrum data thereof (device=AVANCE 400WB by BRUKER; measurement method=13C-CPTOSS method; MAS=6 KHz). FIG. 29 shows the infrared spectrum data thereof (device=FTIR-8300 by Shimadzu Corporation; measurement method=potassium chloride method).

EXAMPLE 21

Preparation of Crystal Form N3

Method 1 Preparation from a Hydrochloride Salt 2 g of a hydrochloride salt of the compound (I) was suspended in 50 mL of a mixed solution of 92.5 vol. % acetonitrile/water and stirred at 10° C. for 24 hours. The precipitated crystal was separated from the slurry to obtain a wet crystal of NW2-type. This crystal was dried at 80° C. for 18 hours under reduced pressure to obtain 0.52 g of a hydrochloride salt of the compound (I) (N-3-type) as a white crystalline solid substance.

Method 2 Preparation from a Free Form 429 mg of the compound (I) was added to 8 mL of acetonitrile, stirred and dissolved by heating at 60° C. 0.8 mL of water was added thereto, and then 0.12 mL of a 6N hydrochloric acid aqueous solution wad added thereto. The mixture was cooled down to room temperature, and the precipitated solid substance was separated and washed with 2 mL of acetonitrile. This crystal was dried at 60° C. under reduced pressure to obtain 212 mg of a hydrochloride salt of the compound (I) (N-3-type) as a white crystalline solid substance.

Figure 30:
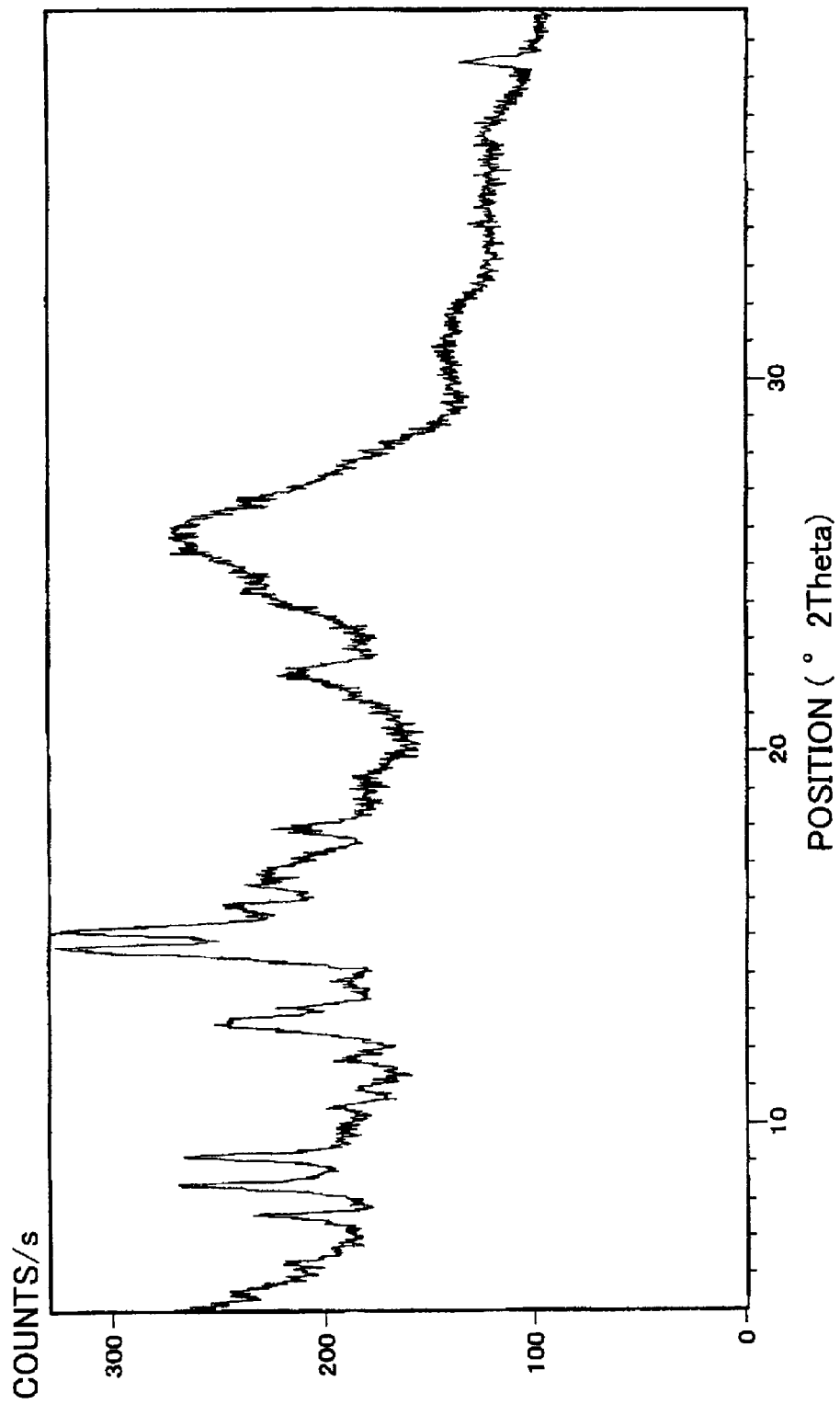
FIG. 30 shows a powder X-ray diffraction pattern of crystal form N3 of a hydrochloride salt of the compound of the formula (I) of the present invention.

Powder X-Ray Diffraction Pattern: FIG. 30

EXAMPLE 22

Preparation of Crystal Form NW4 and Crystal Form N4

2 g of a hydrochloride salt of the compound (I) was suspended in 60 mL of acetonitrile and stirred at 10° C. for 24 hours. The precipitated crystal was separated from the slurry to obtain a wet crystal of NW4-type. This crystal was dried at 80° C. for 18 hours under reduced pressure to obtain 0.73 g of a hydrochloride salt of the compound (I) (N-4-type) as a white crystalline solid substance.

Figure 32:
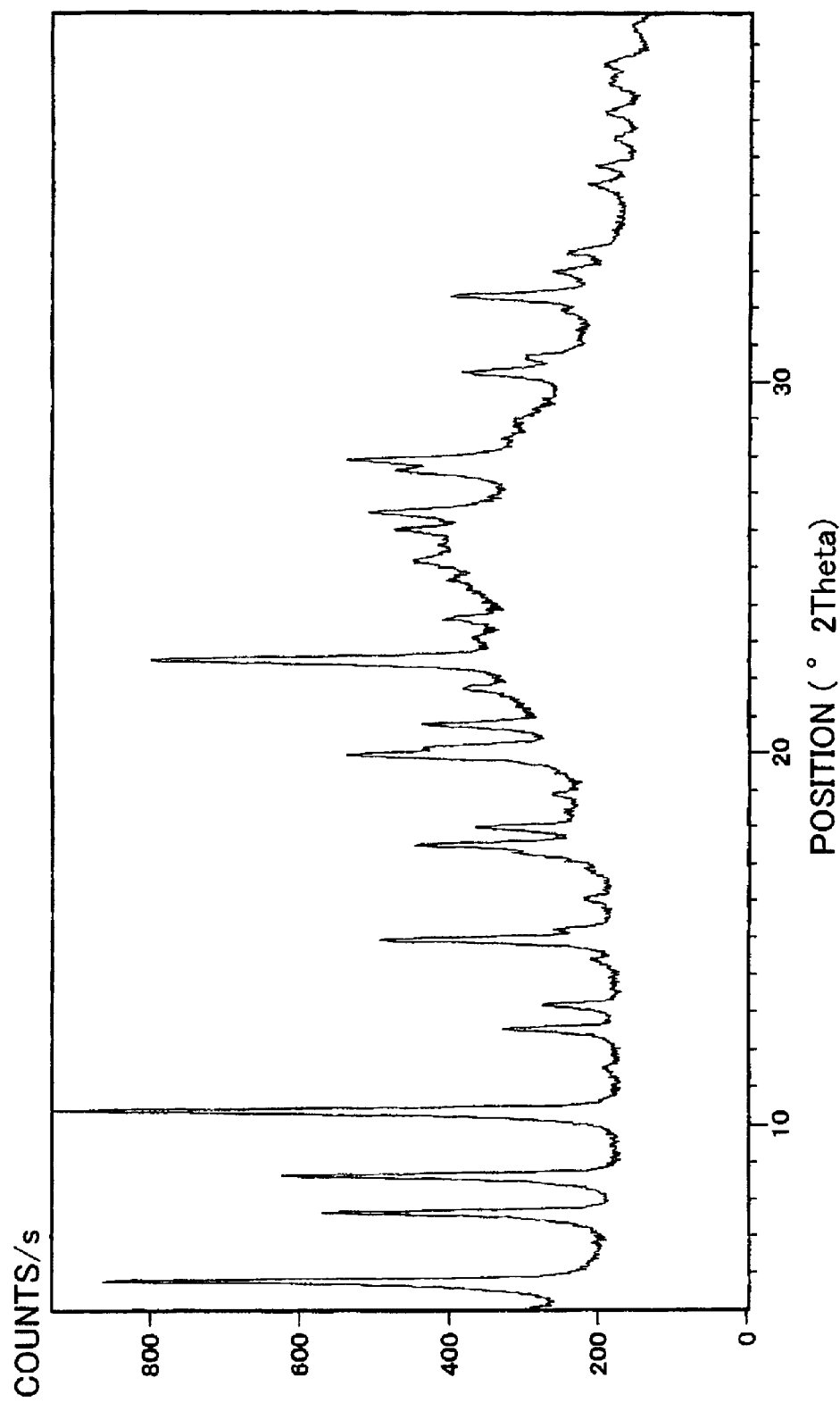
FIG. 32 shows a powder X-ray diffraction pattern of crystal form NW4 of a hydrochloride salt of the compound of the formula (I) of the present invention.
Figure 33:
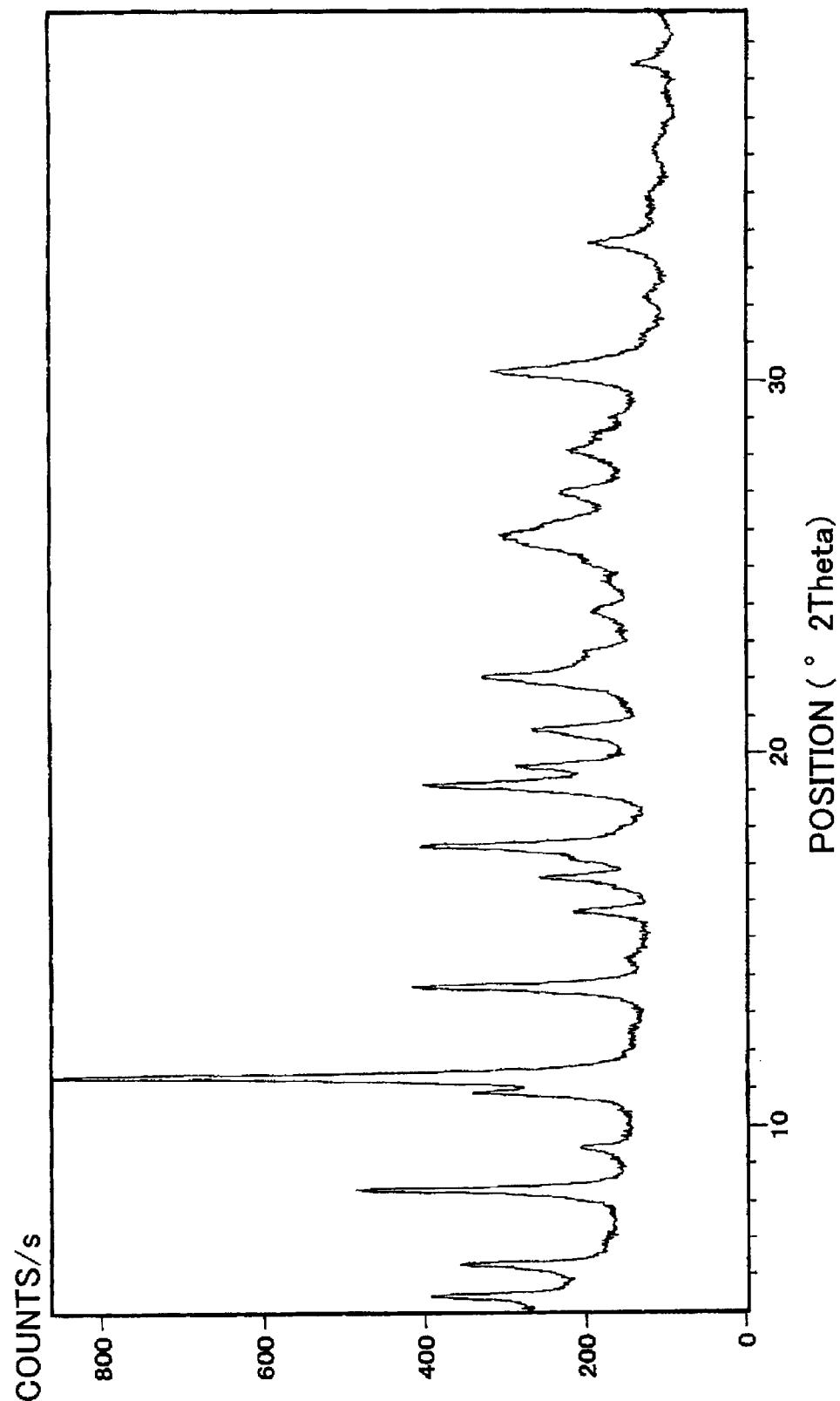
FIG. 33 shows a powder X-ray diffraction pattern of crystal form N4 of a hydrochloride salt of the compound of the formula (I) of the present invention.

Powder X-Ray Diffraction Pattern: FIGS. 32 and 33

EXAMPLE 23

Preparation of Crystal Form NW5 and Crystal Form N5

7 g of a hydrochloride salt of the compound (I) was suspended in 50 mL of a mixed solution of 60 vol. % acetonitrile/water and stirred at 50° C. for 24 hours. The precipitated crystal was separated from the slurry to obtain a wet crystal of NW5-type. This crystal was dried at 80° C. for 18 hours under reduced pressure to obtain 2.11 g of a hydrochloride salt of the compound (I) (N-5-type) as a white crystalline solid substance.

Figure 35:
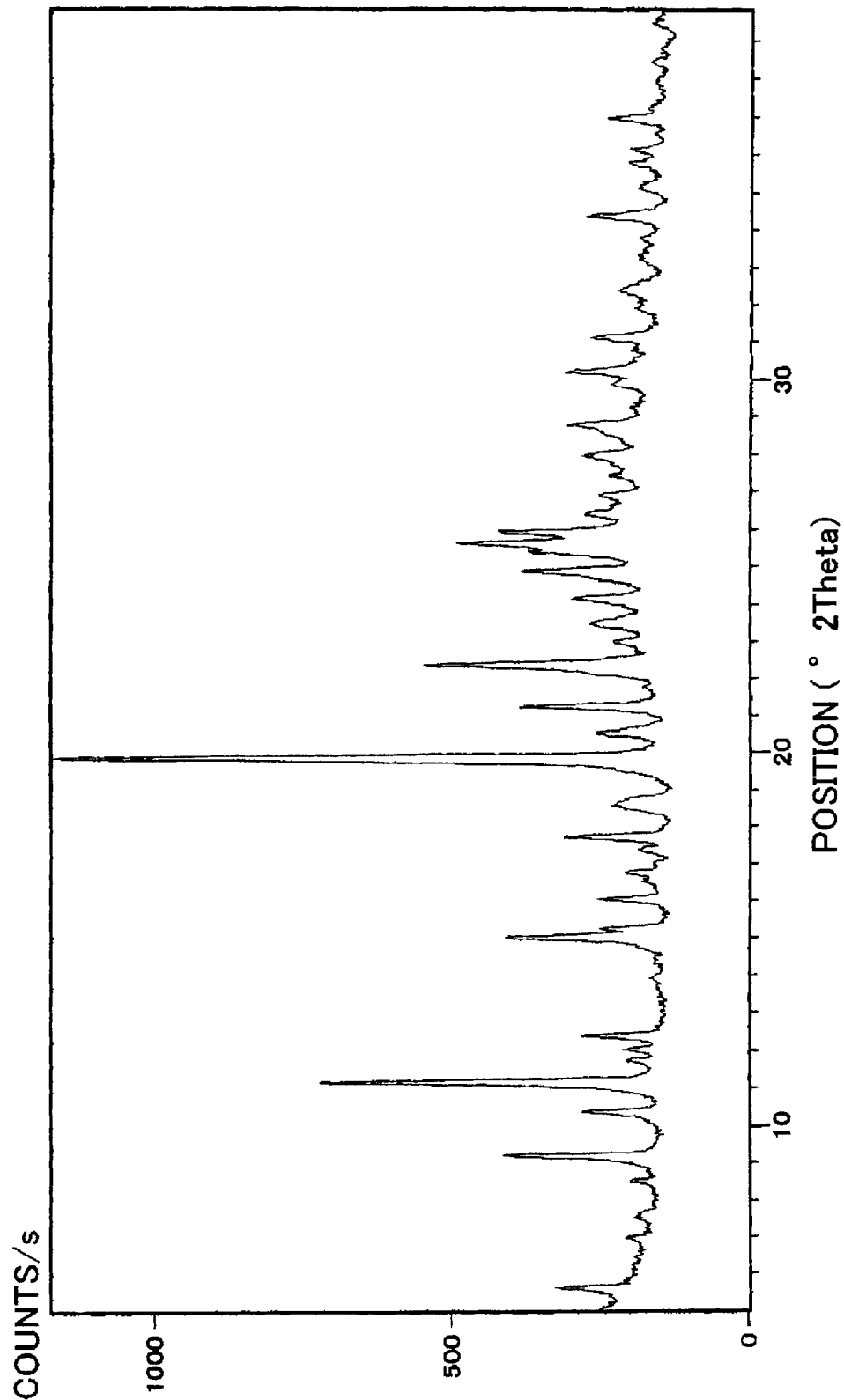
FIG. 35 shows a powder X-ray diffraction pattern of crystal form NW5 of a hydrochloride salt of the compound of the formula (I) of the present invention.
Figure 36:
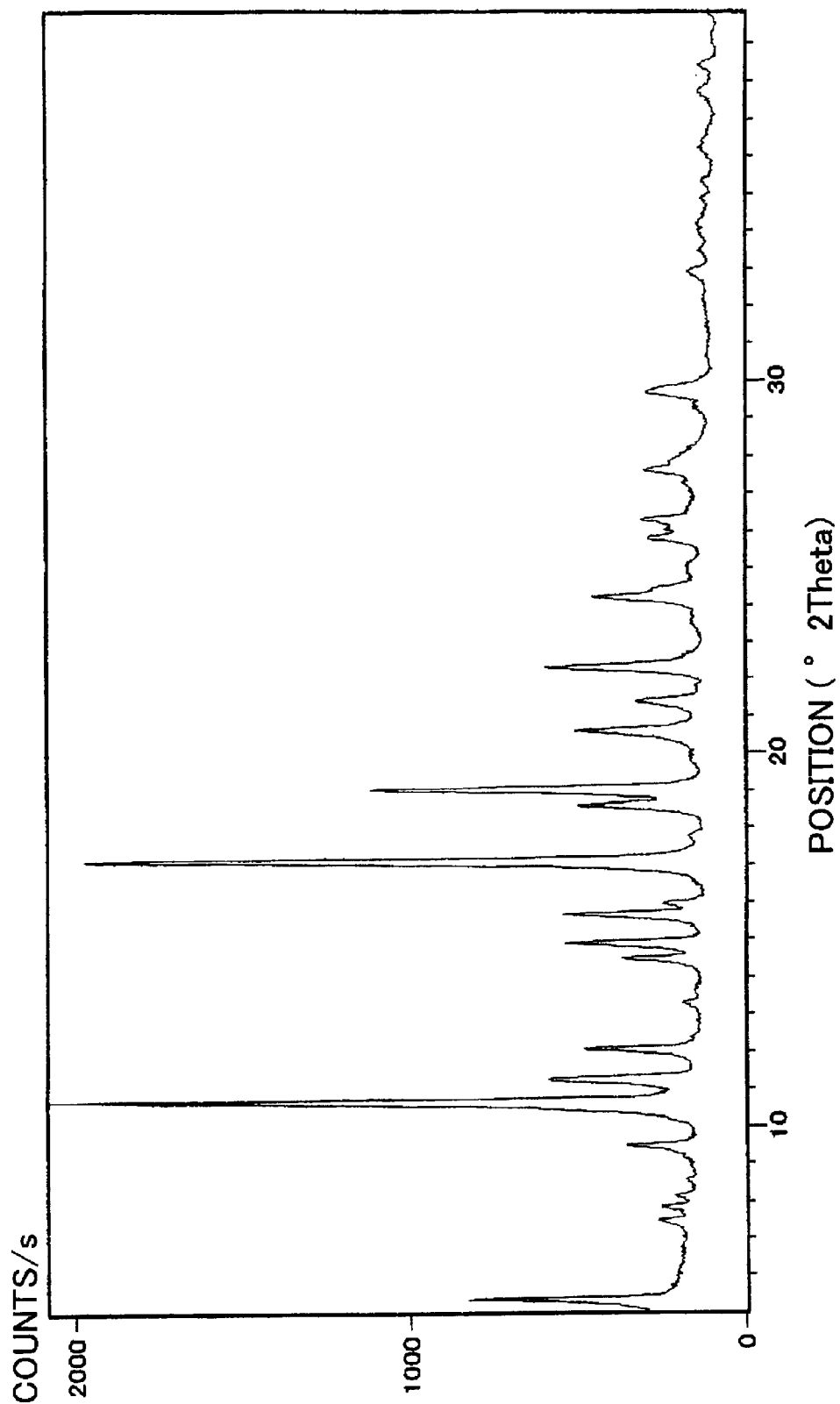
FIG. 36 shows a powder X-ray diffraction pattern of crystal form N5 of a hydrochloride salt of the compound of the formula (I) of the present invention.

Powder X-Ray Diffraction Pattern: FIGS. 35 and 36

EXAMPLE 24

Preparation of Crystal Forms Cl6, Cl7, Cl8, Ca1, Ca2, Ca3, Ca4, Ms1, Ms2, Ms3, Ms4, Ms5, L-Tar1 and L-Tar2

0.14 mmol/mL of an acid solution was prepared by using acids and solvents described in Table 1. 6.7 mL of the solution was added to the compound (I) (500 mg, 0.837 mmol) prepared in the referential example and heated up from 20° C. to 60° C. (at a heating rate of 1° C./minute) with stirring. The reactant was kept at 60° C. for 30 minutes and cooled down from 60° C. to 5° C. for 11 hours (at a cooling rate of 5° C./hour). Then, it was aged at 5° C. for about 11 hours, filtered and dried under reduced pressure (at room temperature for 48 hours or more) to obtain a crystal.

TABLE 1

| Example | Form | Acid | Solvent |
|---|---|---|---|
| | Cl6 | conc. HCl | Ether |
| | Cl7 | conc. HCl | DME |
| | Cl8 | conc. HCl | IPA |
| | Ca1 | Citric acid | IPA |
| | Ca2 | Citric acid | 1-BuOH |
| | Ca3 | Citric acid | DME |
| | Ca4 | Citric acid | Acetone |
| | Ms1 | MsOH | MeOH |
| | Ms2 | MsOH | THF |
| | Ms3 | MsOH | $^t$BuOMe |
| | Ms4 | MsOH | DME |
| | Ms5 | MsOH | Acetone |
| | L-Tar1 | L-Tartaric acid | DME |
| | L-Tar2 | L-Tartaric acid | Acetone |

Ether: diethyl ether

Powder X-Ray Diffraction Pattern: FIGS. 38 to 51
The measurement results of $^1$H-NMR are shown below:

(Crystal form Ca4)
$^1$H-NMR (DMSO-$d_6$): δ 1.19 (3H, d, J=6.0 Hz), 1.23 (3H, d, J=6.0 Hz), 2.45-2.58 (m), 3.01 (1H, dd, J=14.1, 9.9 Hz), 3.19 (1H, dd, J=14.4, 5.7 Hz), 3.55 (3H, s), 4.20 (2H, s), 4.73-4.80 (1H, m), 4.91-4.99 (1H, m), 7.21 (2H, d, J=9.0 Hz), 7.37-7.47 (5H, m), 7.58 (1H, d, J=8.7 Hz), 7.87 (1H, d, J=8.4 Hz), 8.22 (1H, s), 9.24 (1H, d, J=8.4 Hz).

(Crystal Form Ms1)
$^1$H-NMR (DMSO-$d_6$): δ 1.19 (3H, d, J=6.3 Hz), 1.23 (3H, d, J=6.3 Hz), 2.31 (3H, s), 2.58 (3H, s), 3.01 (1H, dd, J=14.1, 9.9 Hz), 3.19 (1H, dd, J=14.1, 5.4 Hz), 3.55 (3H, s), 4.24 (2H, brs), 4.77 (1H, m), 4.95 (1H, m), 7.21 (2H, m), 7.38-7.47 (5H, m), 7.59 (1H, d, J=8.7 Hz), 7.88 (1H, dd, J=8.7, 2.1 Hz), 8.24 (1H, d, J=2.1 Hz), 8.75 (brs, 2H), 9.24 (1H, d, J=7.8 Hz).

(Crystal Form L-Tar1)

$^1$H-NMR (DMSO-$d_6$): δ 1.19 (3H, d, J=6.0 Hz), 1.23 (3H, d, J=6.0 Hz), 3.01 (1H, dd, J=13.8, 9.6 Hz), 3.19 (1H, dd, J=13.8, 5.4 Hz), 3.54 (3H, s), 3.91 (2H, s), 4.13 (2H, s), 4.73-4.80 (1H, m), 4.91-4.99 (1H, m), 7.20 (2H, d, J=8.4 Hz), 7.37-7.47 (5H, m), 7.56 (1H, d, J=8.7 Hz), 7.87 (1H, d, J=8.4 Hz), 8.19 (1H, s), 9.24 (1H, d, J=8.1 Hz).

TEST EXAMPLES

The following Test Examples will illustrate the effect of the present invention. Test Example 4 confirmed thermodynamically stable crystal types, and Test Example 5 confirmed chemically stable crystal types. Besides, Test Example 6 confirmed stable crystal types which do not depend on relative humidity, and Test Example 7 confirmed poorly hygroscopic crystal types.

TEST EXAMPLE 4

Differential Scanning Calorimetry (DSC)

(1) Measurement Method and the Condition 1 to 5 mg of a sample of each crystal obtained above (crystal forms A, Br4, Cl5 or Br5) was weighed by scales and sealed in an aluminum pan. Then, DSC was conducted in accordance with the following condition.

Reference: An empty aluminum pan
Sampling time: 0.2 sec.
Range: 25 to 350° C.
Heating time: 10 or 20° C./min.

Figure 2:
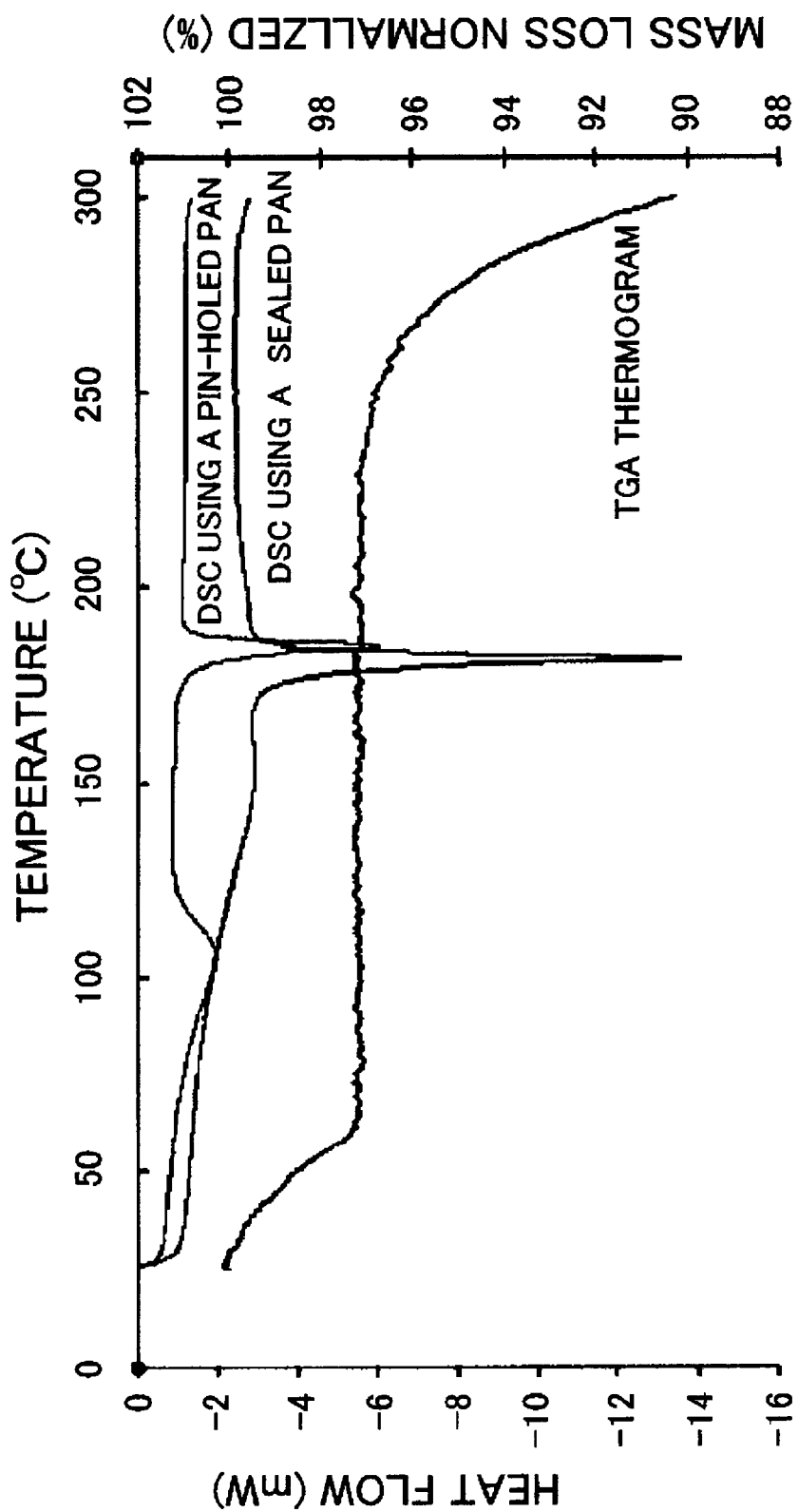
FIG. 2 shows a DSC curve of crystal form A of the compound (free form) of the formula (I) of the present invention. (Preparation of crystal form A)
Figure 10:
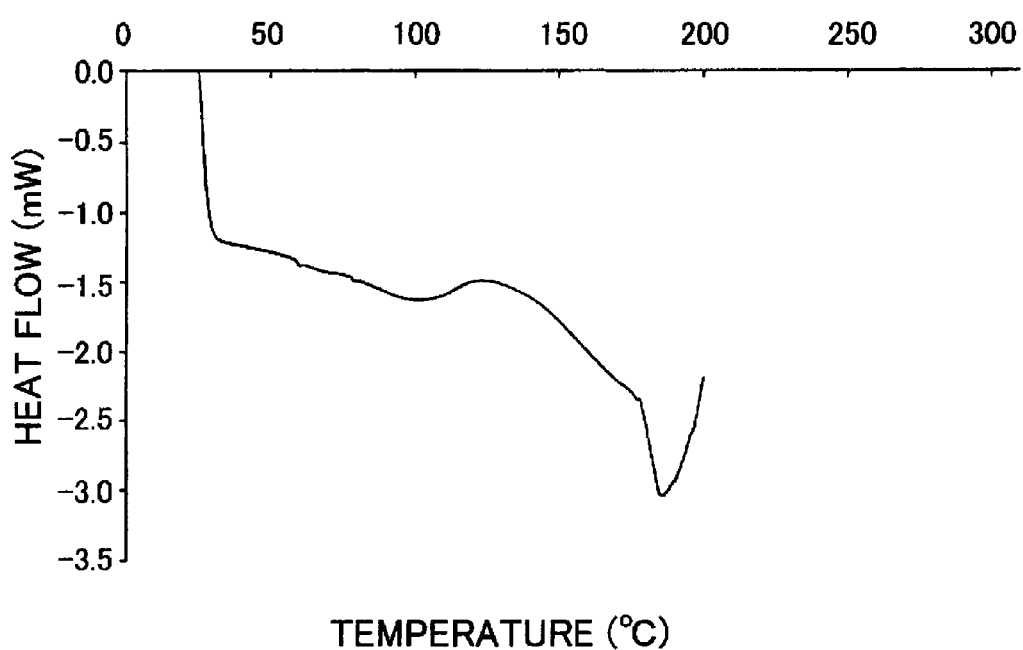
FIG. 10 shows a DSC curve of Crystal form Br4 of a hydrobromide salt of the compound of the formula (I) of the present invention.
Figure 18:
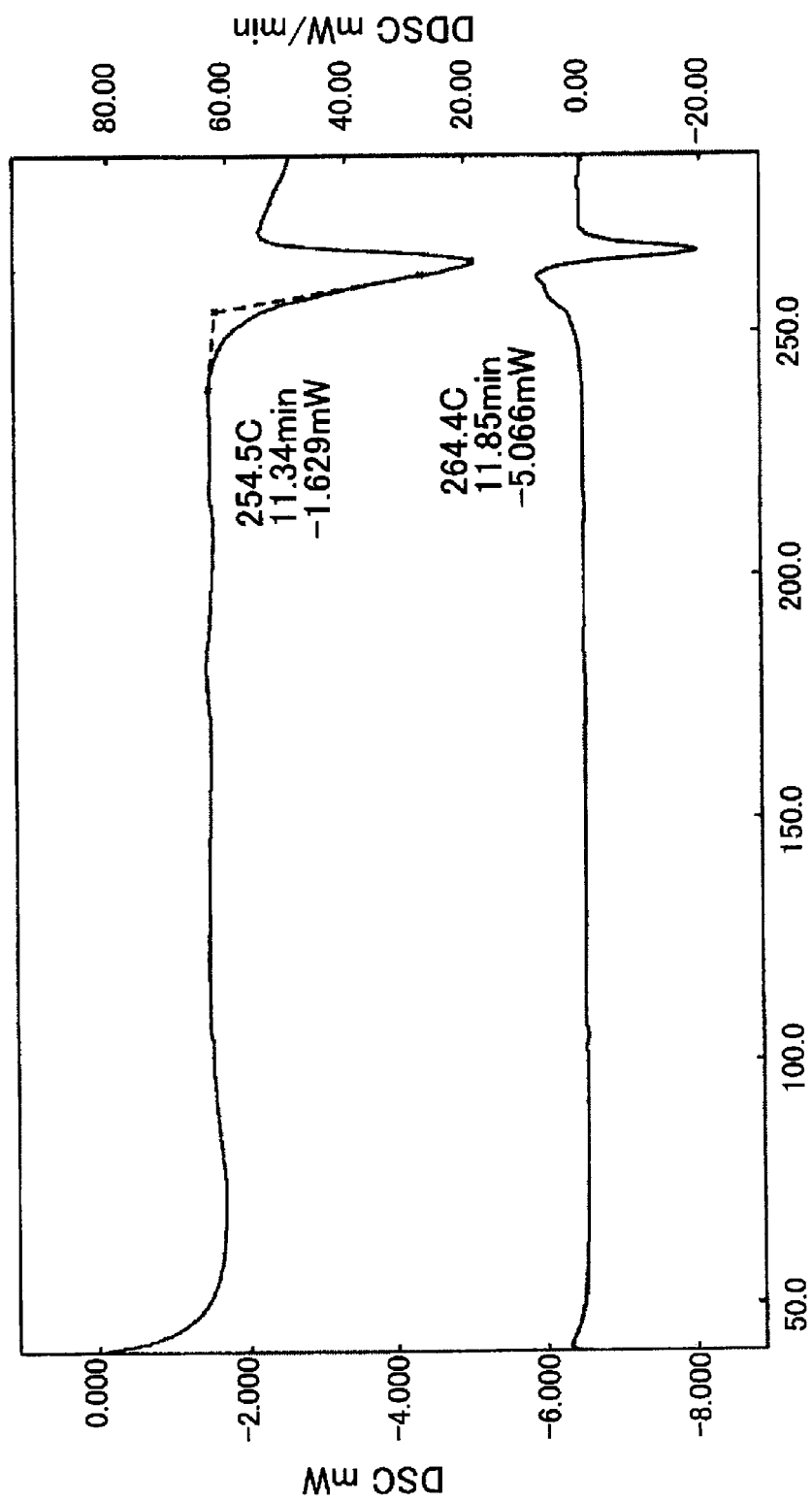
FIG. 18 shows a DSC curve of crystal form Cl5 of a hydrochloride salt of the compound of the formula (I) of the present invention. The horizontal axis is Temp (° C.).
Figure 19:
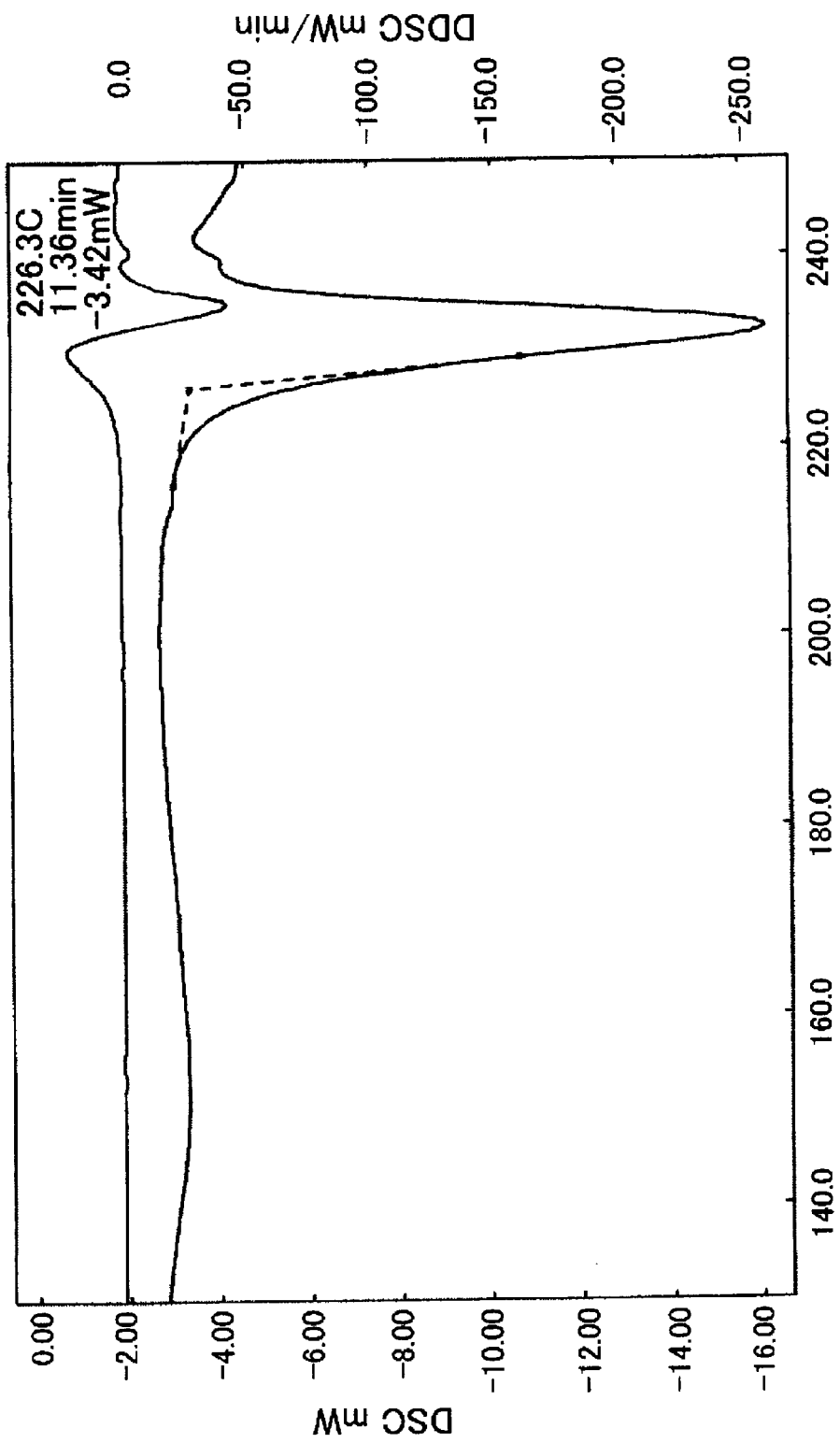
FIG. 19 shows a DSC curve of crystal form Br5 of a hydrobromide salt of the compound of the formula (I) of the present invention.

The results are shown in FIG. 2 (crystal form A), FIG. 10 (crystal form Br4), FIG. 18 (crystal form Cl5) and FIG. 19 (crystal form Br5).

The melting point of crystal from Cl5 by DSC is high temperature around 255° C. (250 to 260° C.), and that of crystal form Br5 by DSC is also high temperature around 226° C. (221 to 231° C.).

TEST EXAMPLE 5

Preservation Stability Test

Crystal form Cl5, crystal form Br5 and crystal form A were preserved in the following condition, and then the amount of impurities in each sample was compared. However, the increase in the impurities by heating was not observed.

Duration: 4 weeks

Temperature/humidity:
40° C./75% relative humidity—opened
60° C./opened
Room temperature/closed (control)

TEST EXAMPLE 6

Powder X-Ray Diffraction Measurement Under the Control of Relative Humidity

The powder X-ray diffraction of each of crystal form Cl5 and crystal form Mal2 was measured in the following condi-tion, and the diffraction patterns between dry one and wet one were compared. However, there was no difference thereof in each crystal.

Drying condition (dry): measurement of a sample with drying it at 50° C. under reduced pressure Humid condition (wet): measurement of a sample under 85% relative humidity Powder diffractometer: RINT2100S by RIGAKU (and a temperature and humidity attachment for said diffractometer)
Humidity generator: SRH-1R Shinei Co., Inc.

TEST EXAMPLE 7

Preparation of Vapor Adsorption Isotherms 50 mg of each of crystal form Cl5 and Ml2-crystal was weighed by scales and vacuum dried at 50° C. overnight. Then, at constant temperature, the water adsorption amount of each crystal was measured with an automatic vapor adsorption measurement apparatus (BELSORP-18, by BEL Japan, Inc.). (Mitsuiki et al., J. Agric. Food Chem., Vol. 46, No. 9, Page 3528-34, 1998)

The water adsorption amount of each of crystal form Cl5 and Ml2-crystal was low even in 100% relative humidity, that is, 4% or lower.

TEST EXAMPLE 8

Differential Scanning Calorimetry (DSC)

(1) Measurement Method and the Condition 1 to 5 mg of a sample of each crystal obtained above (crystal forms N1 to N5, Cl6 to Cl8 and Ms1) was weighed by scales and sealed in an aluminum pan. Then, DSC was conducted in accordance with the following condition.

Figure 24:
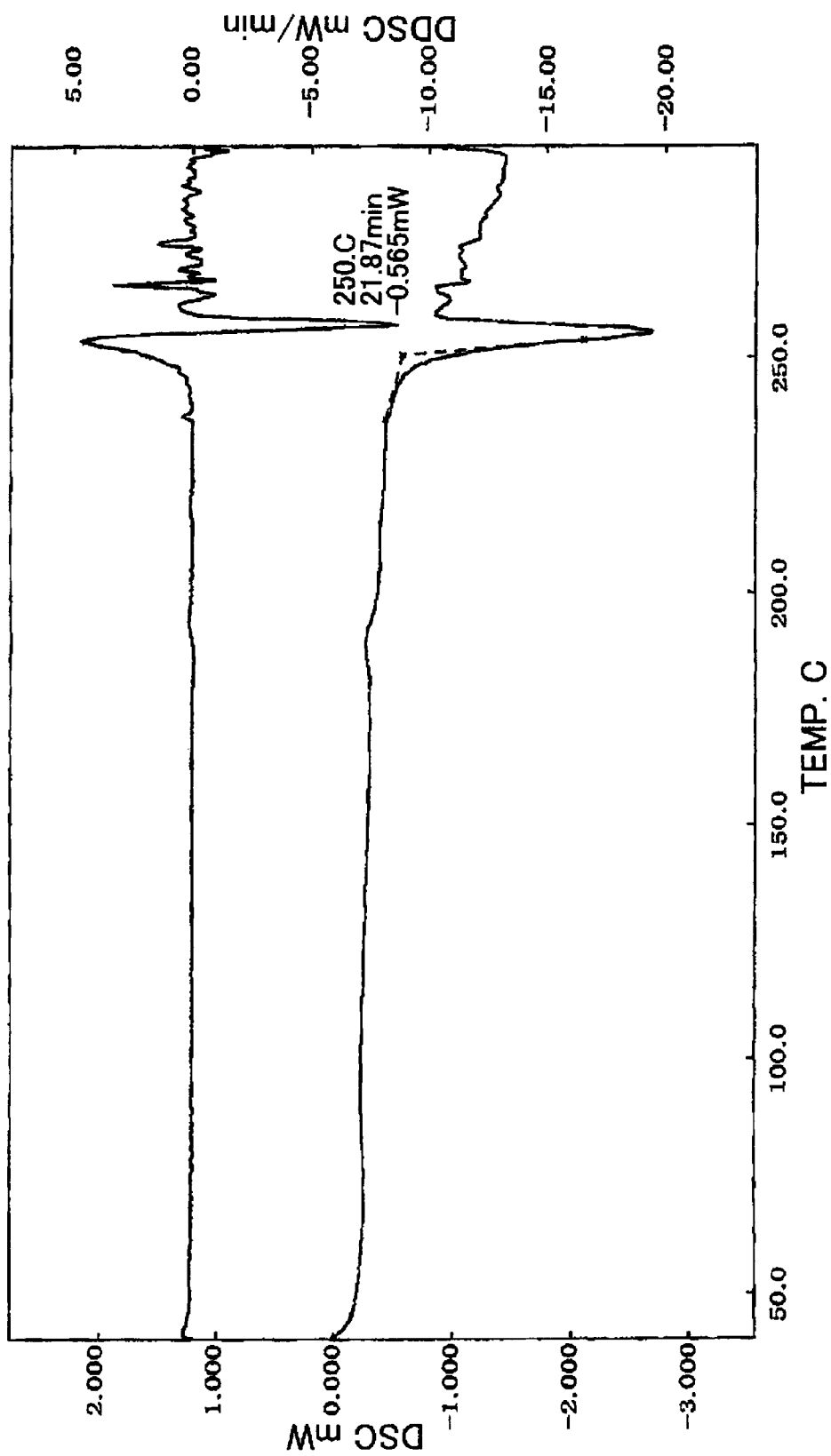
FIG. 24 shows a DSC curve of crystal form N1 of a hydrochloride salt of the compound of the formula (I) of the present invention.
Figure 27:
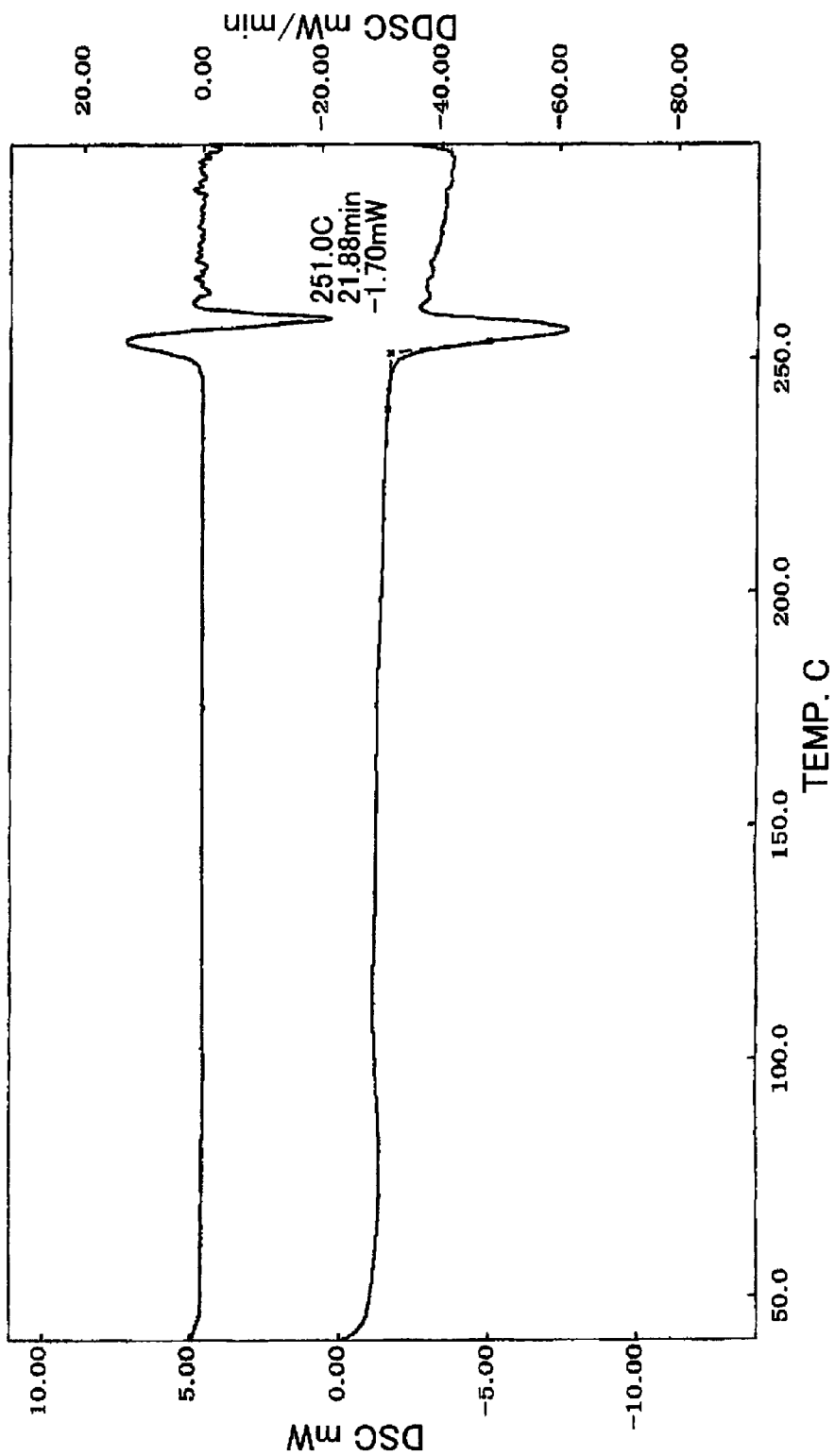
FIG. 27 shows a DSC curve of crystal form N2 of a hydrochloride salt of the compound of the formula (I) of the present invention.
Figure 31:
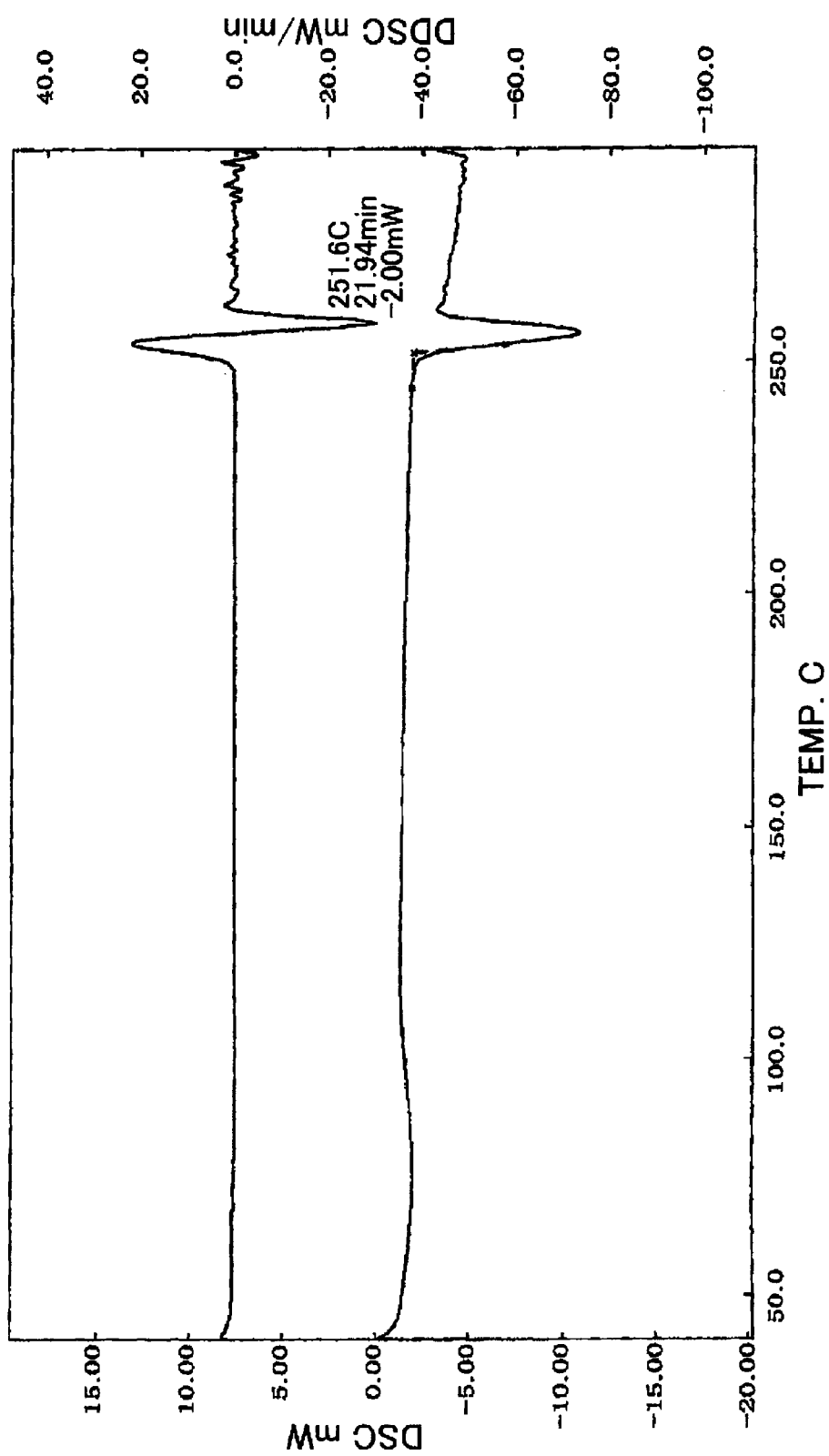
FIG. 31 shows a DSC curve of crystal form N3 of a hydrochloride salt of the compound of the formula (I) of the present invention.
Figure 34:
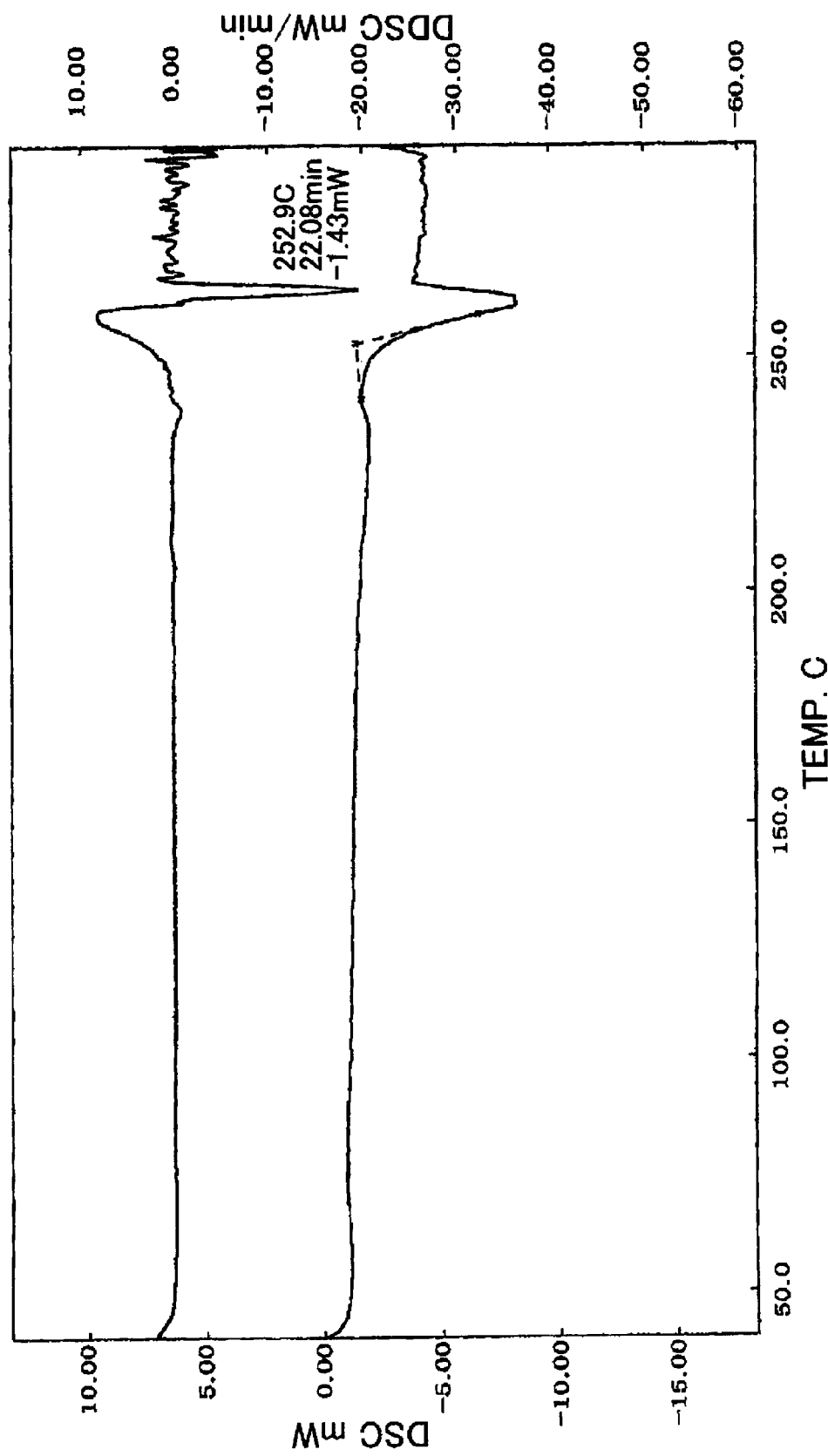
FIG. 34 shows a DSC curve of crystal form N4 of a hydrochloride salt of the compound of the formula (I) of the present invention.
Figure 37:
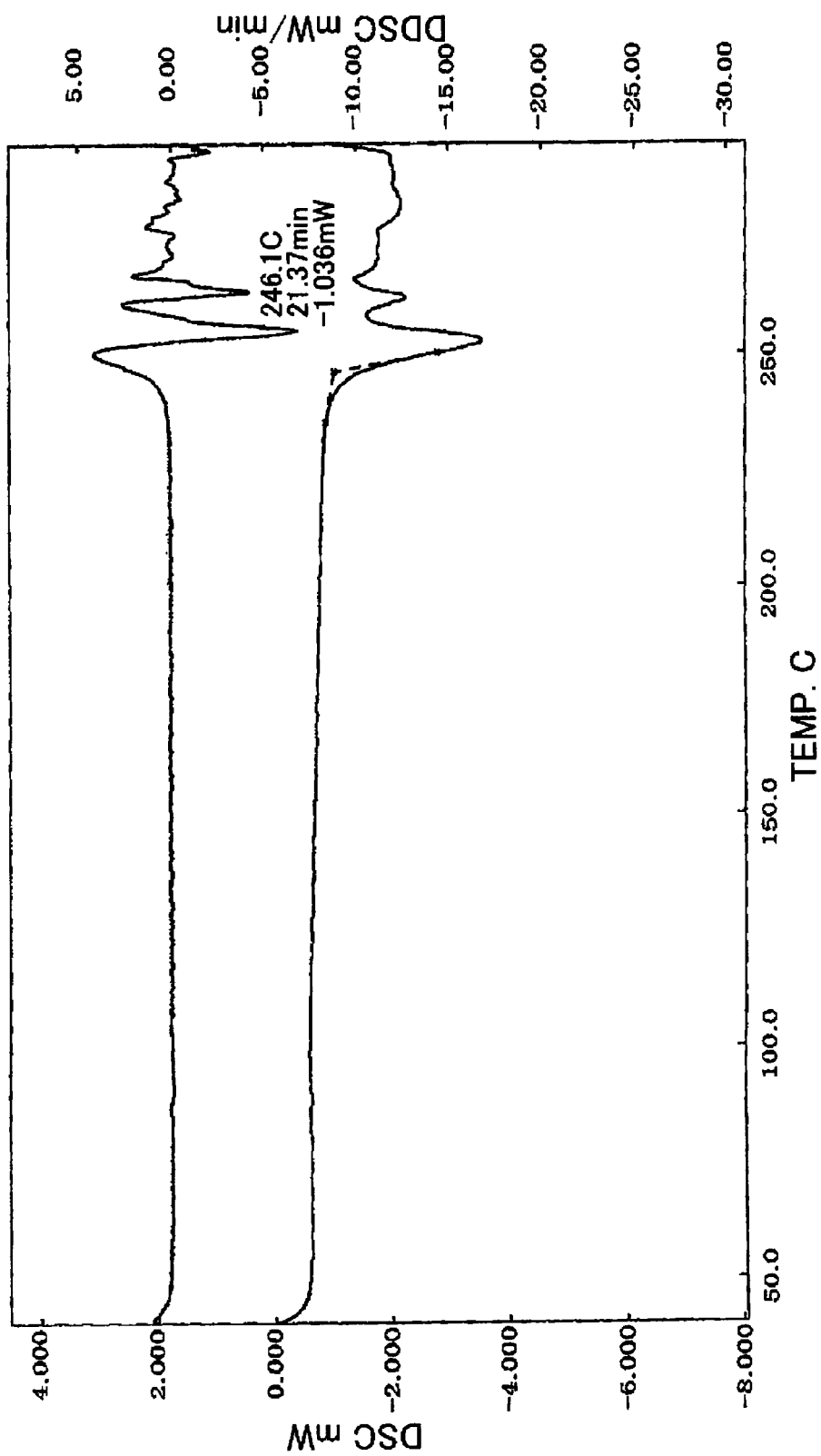
FIG. 37 shows a DSC curve of crystal form N5 of a hydrochloride salt of the compound of the formula (I) of the present invention.
Figure 38:
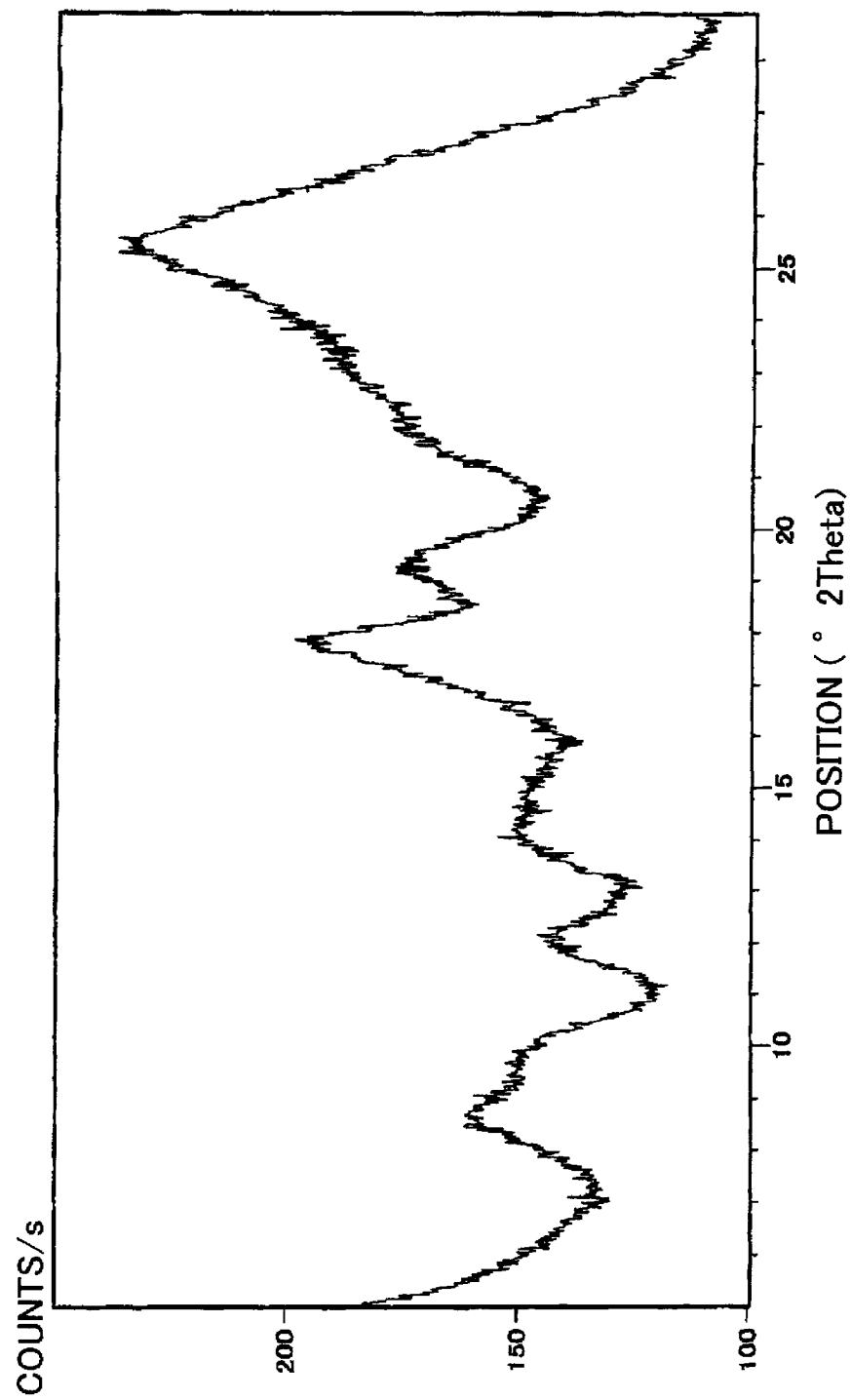
FIG. 38 shows a powder X-ray diffraction pattern of crystal form Cl6 of a hydrochloride salt of the compound of the formula (I) of the present invention.
Figure 39:
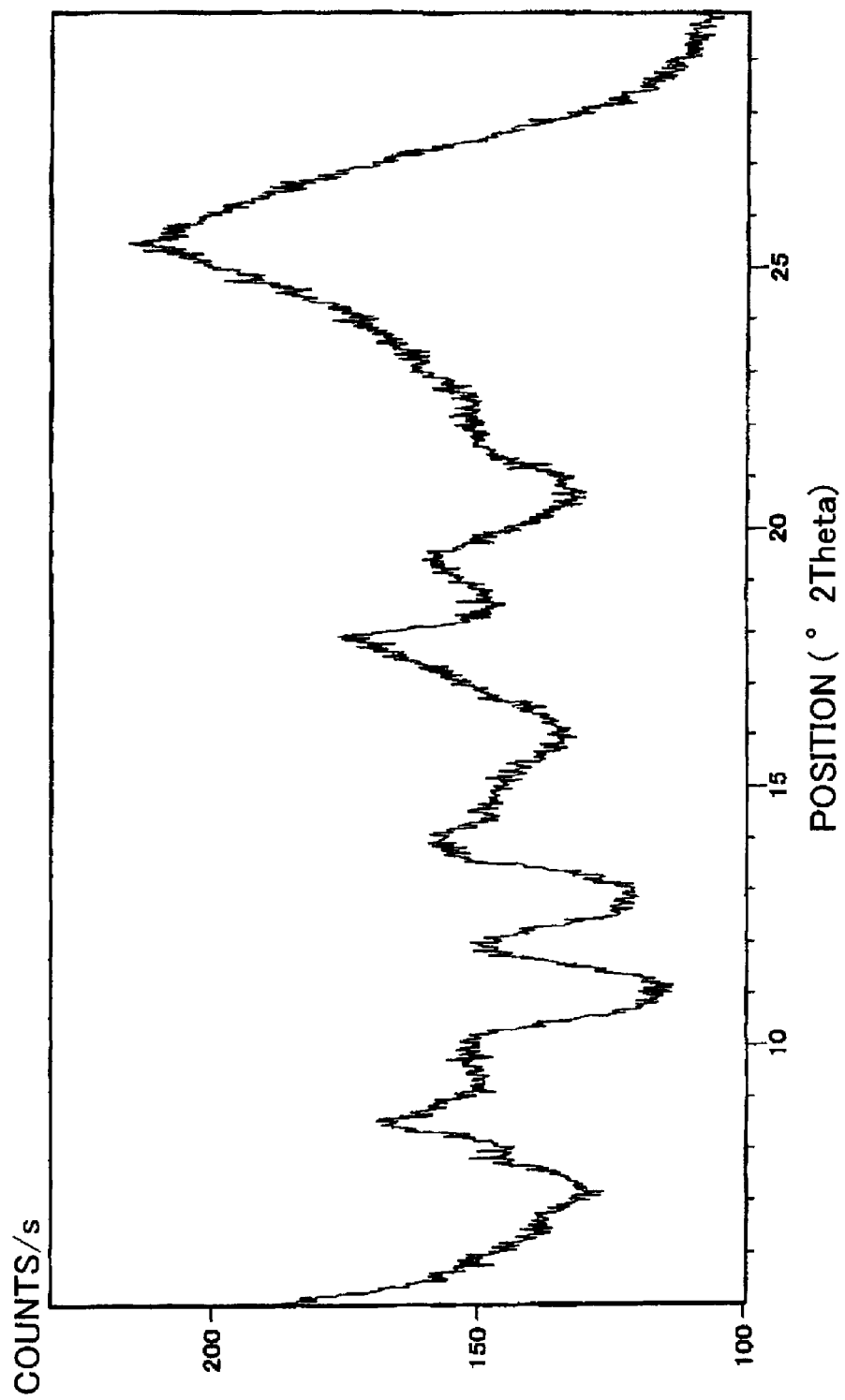
FIG. 39 shows a powder X-ray diffraction pattern of crystal form Cl7 of a hydrochloride salt of the compound of the formula (I) of the present invention.
Figure 40:
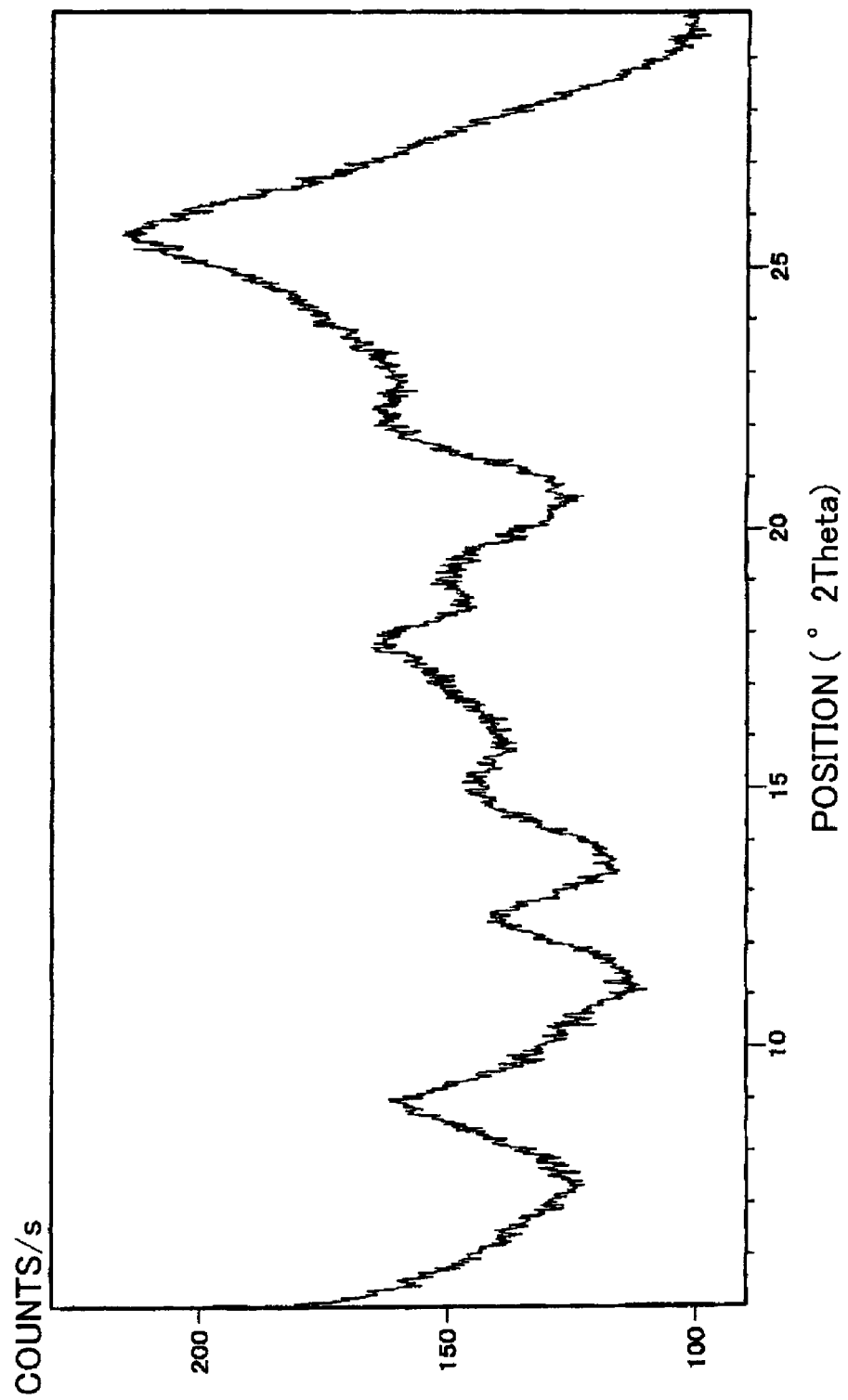
FIG. 40 shows a powder X-ray diffraction pattern of crystal form Cl8 of a hydrochloride salt of the compound of the formula (I) of the present invention.
Figure 41:
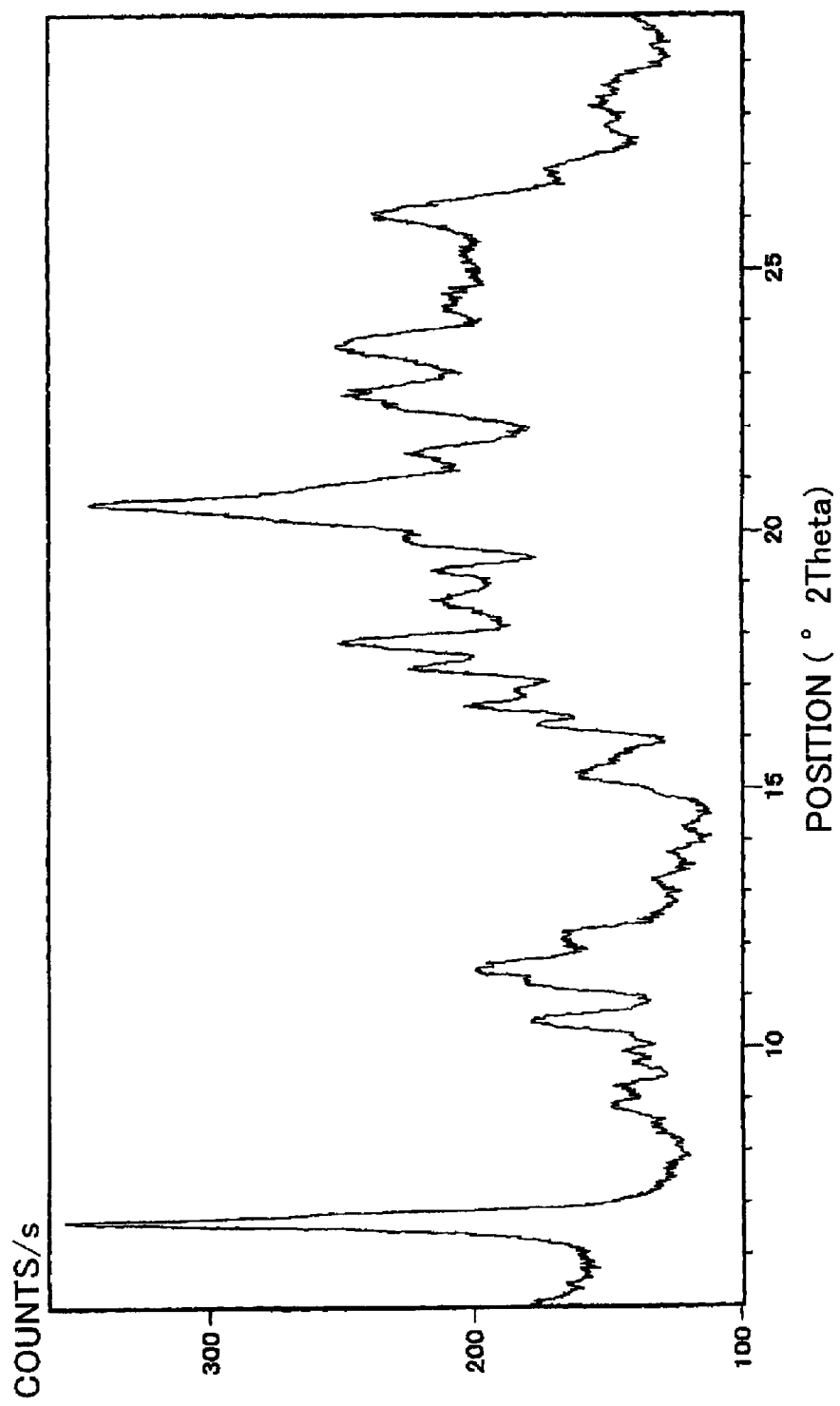
FIG. 41 shows a powder X-ray diffraction pattern of crystal form Ca1 of a citrate salt of the compound of the formula (I) of the present invention.
Figure 42:
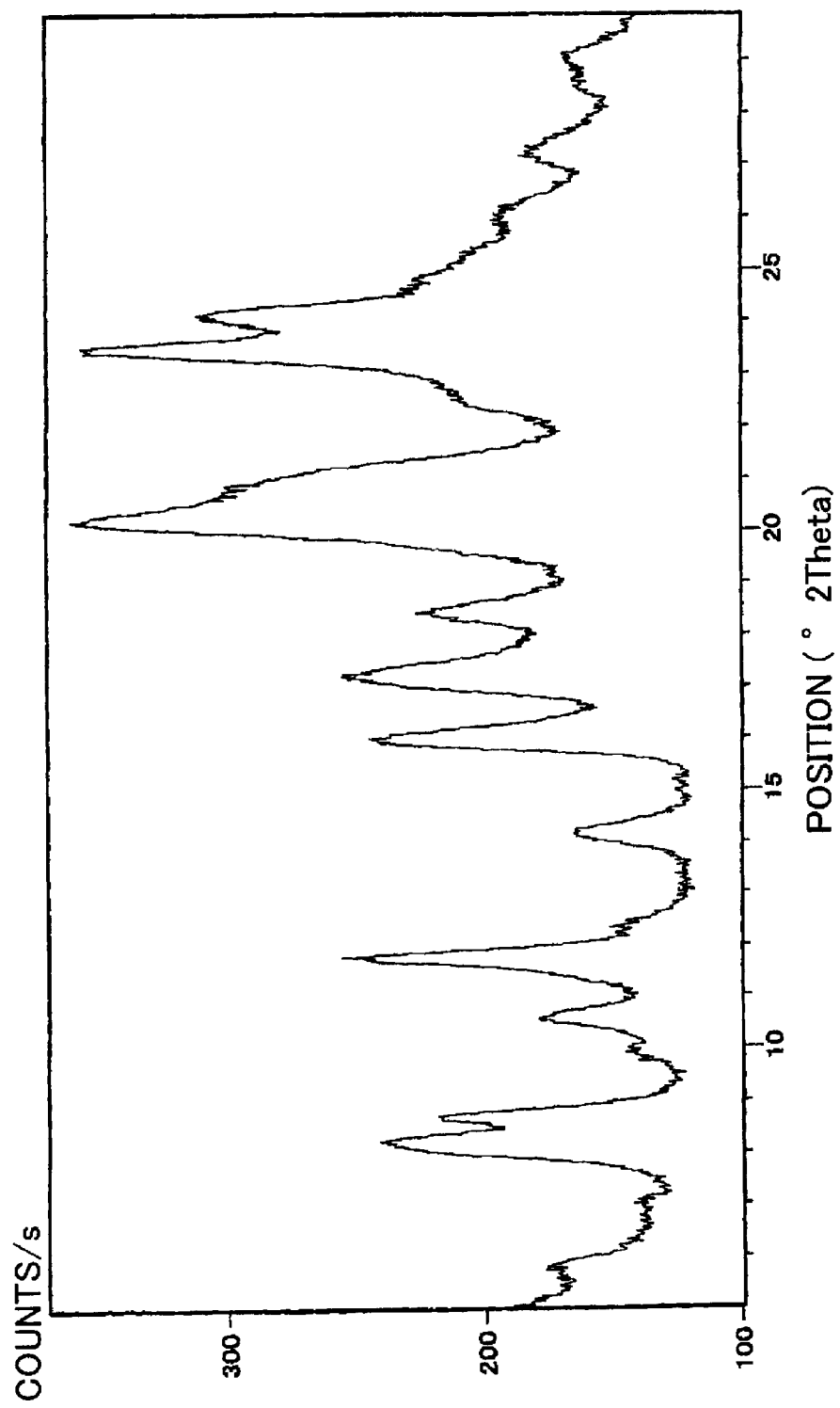
FIG. 42 shows a powder X-ray diffraction pattern of crystal form Ca2 of a citrate salt of the compound of the formula (I) of the present invention.
Figure 43:
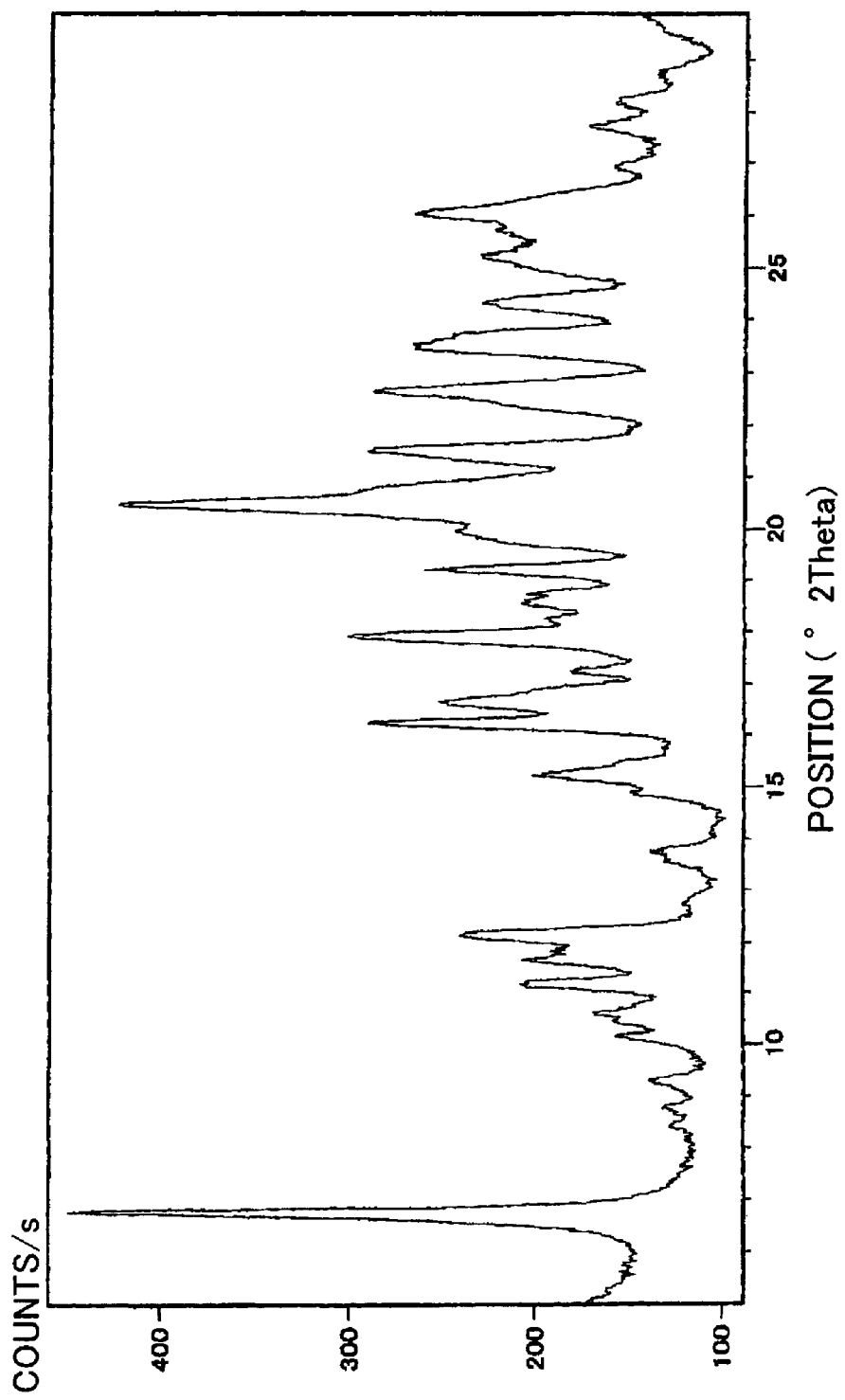
FIG. 43 shows a powder X-ray diffraction pattern of crystal form Ca3 of a citrate salt of the compound of the formula (I) of the present invention.
Figure 44:
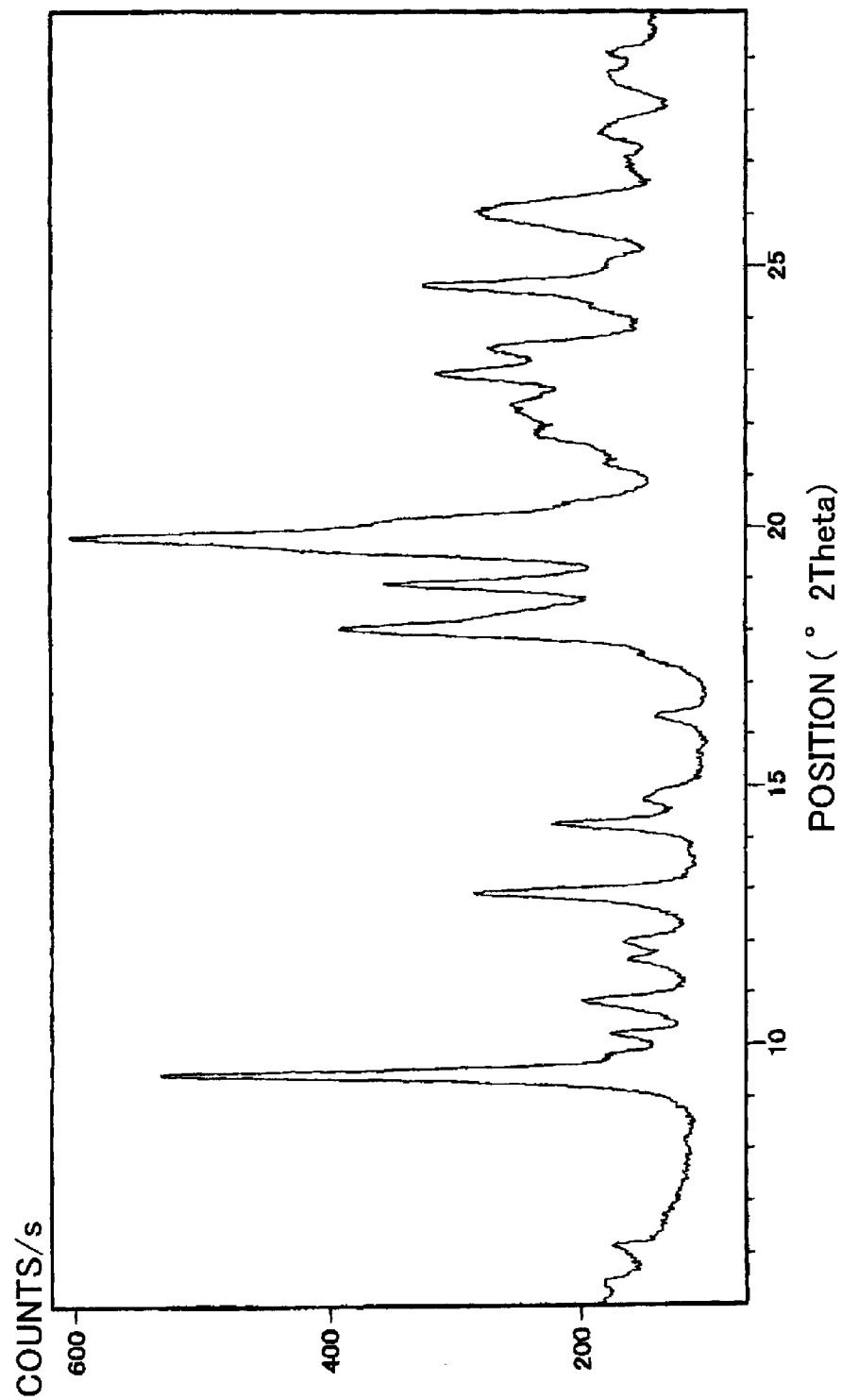
FIG. 44 shows a powder X-ray diffraction pattern of crystal form Ca4 of a citrate salt of the compound of the formula (I) of the present invention.
Figure 45:
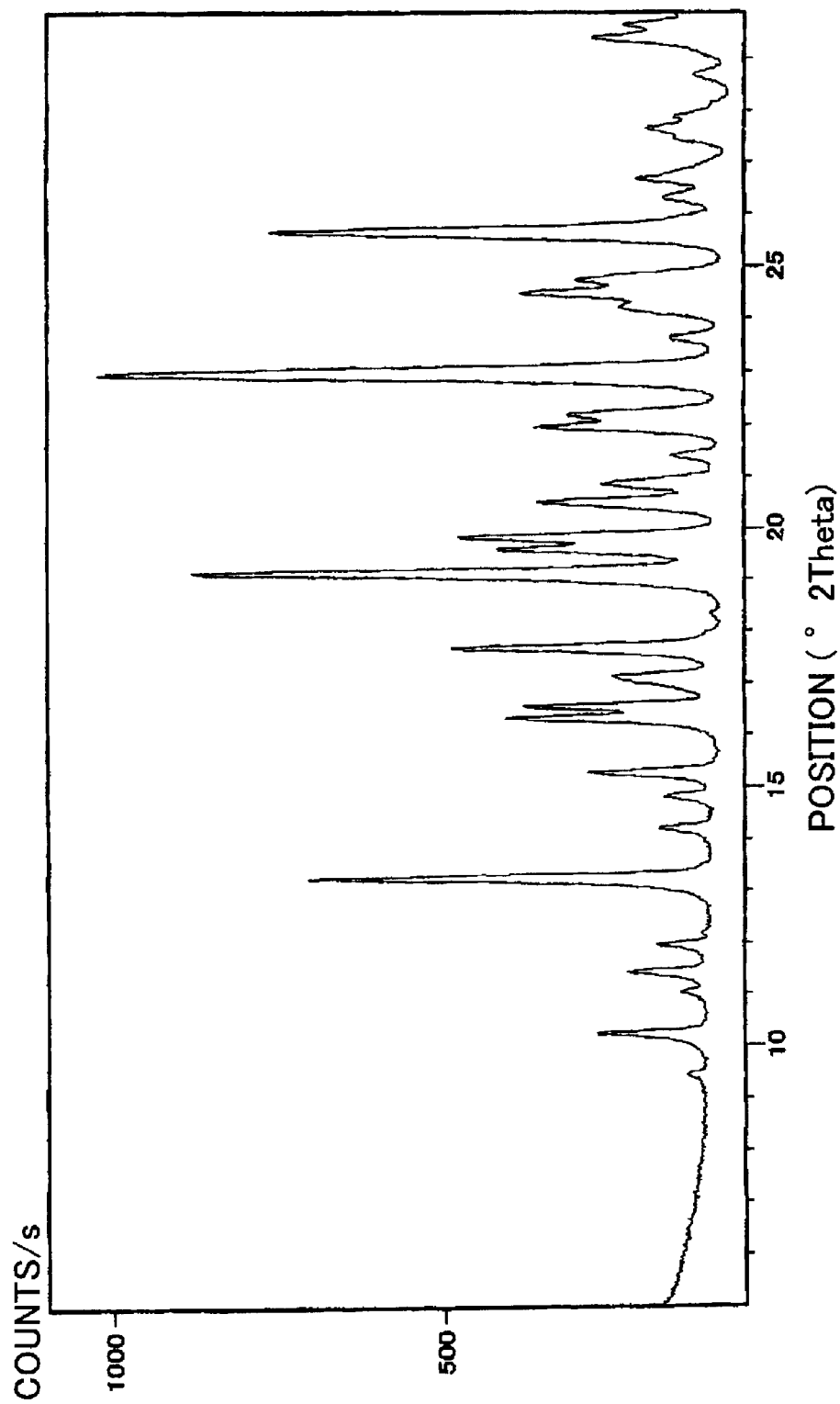
FIG. 45 shows a powder X-ray diffraction pattern of crystal form Ms1 of a methanesulfonate salt of the compound of the formula (I) of the present invention.
Figure 46:
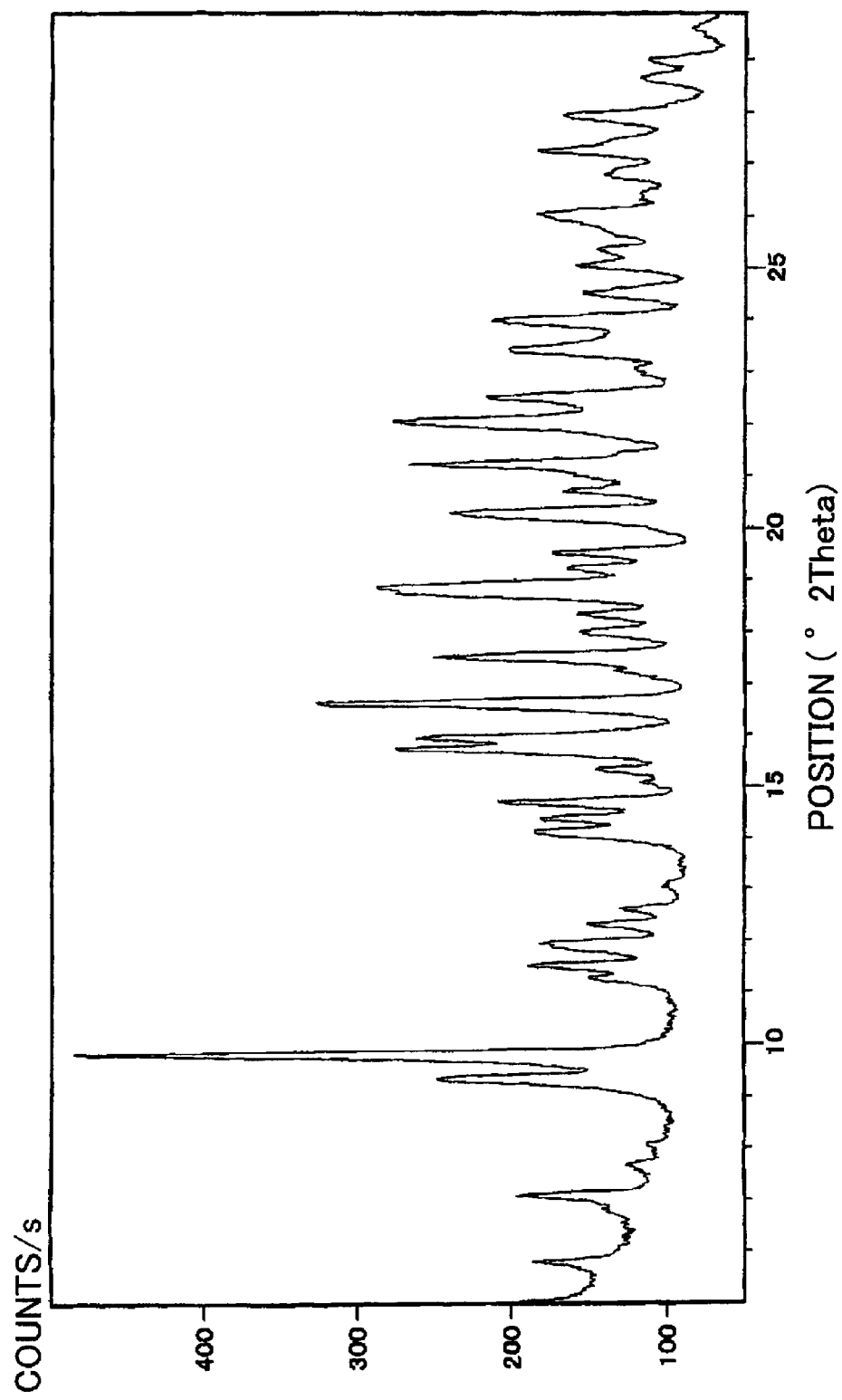
FIG. 46 shows a powder X-ray diffraction pattern of crystal form Ms2 of a methanesulfonate salt of the compound of the formula (I) of the present invention.
Figure 47:
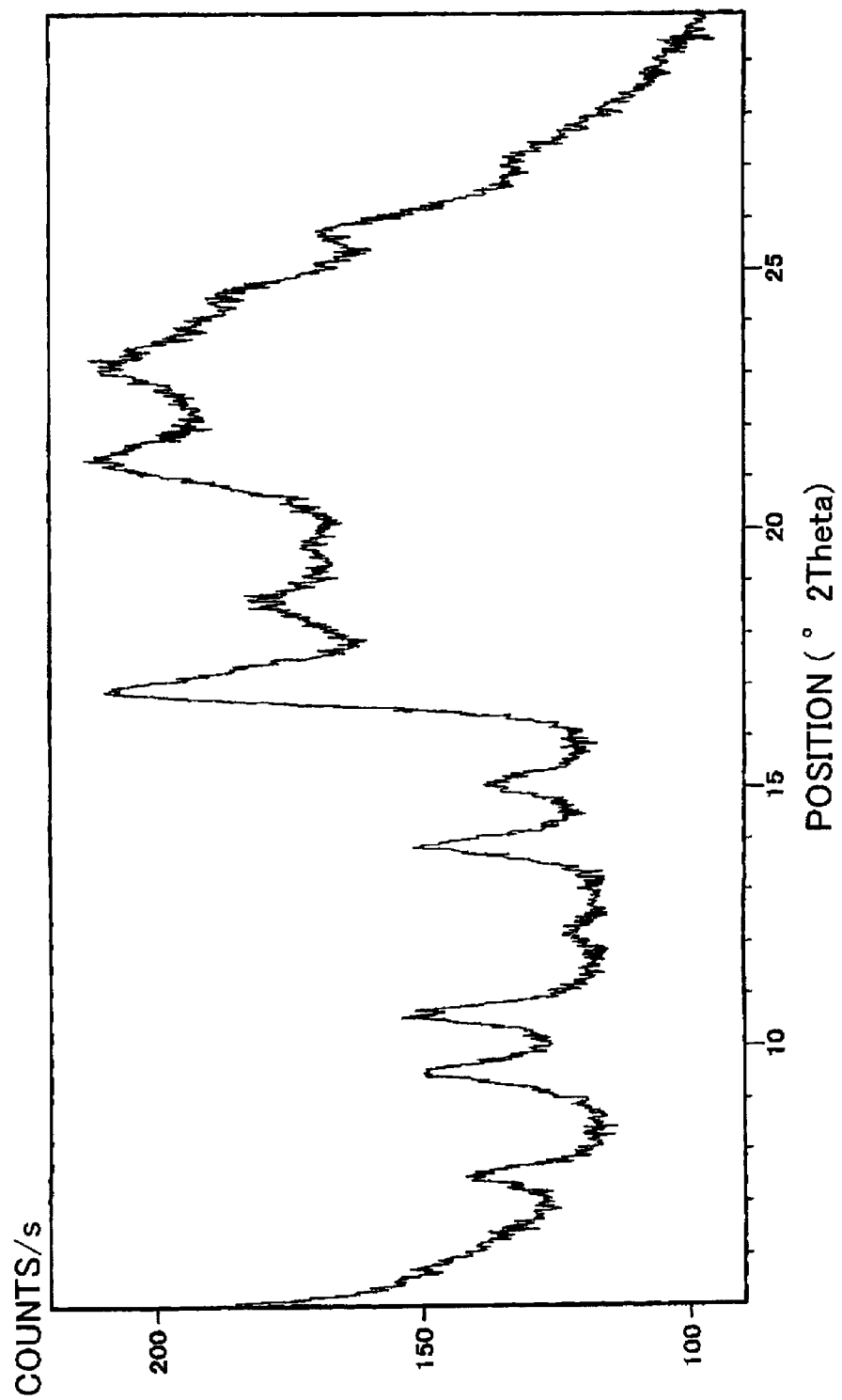
FIG. 47 shows a powder X-ray diffraction pattern of crystal form Ms3 of a methanesulfonate salt of the compound of the formula (I) of the present invention.
Figure 48:
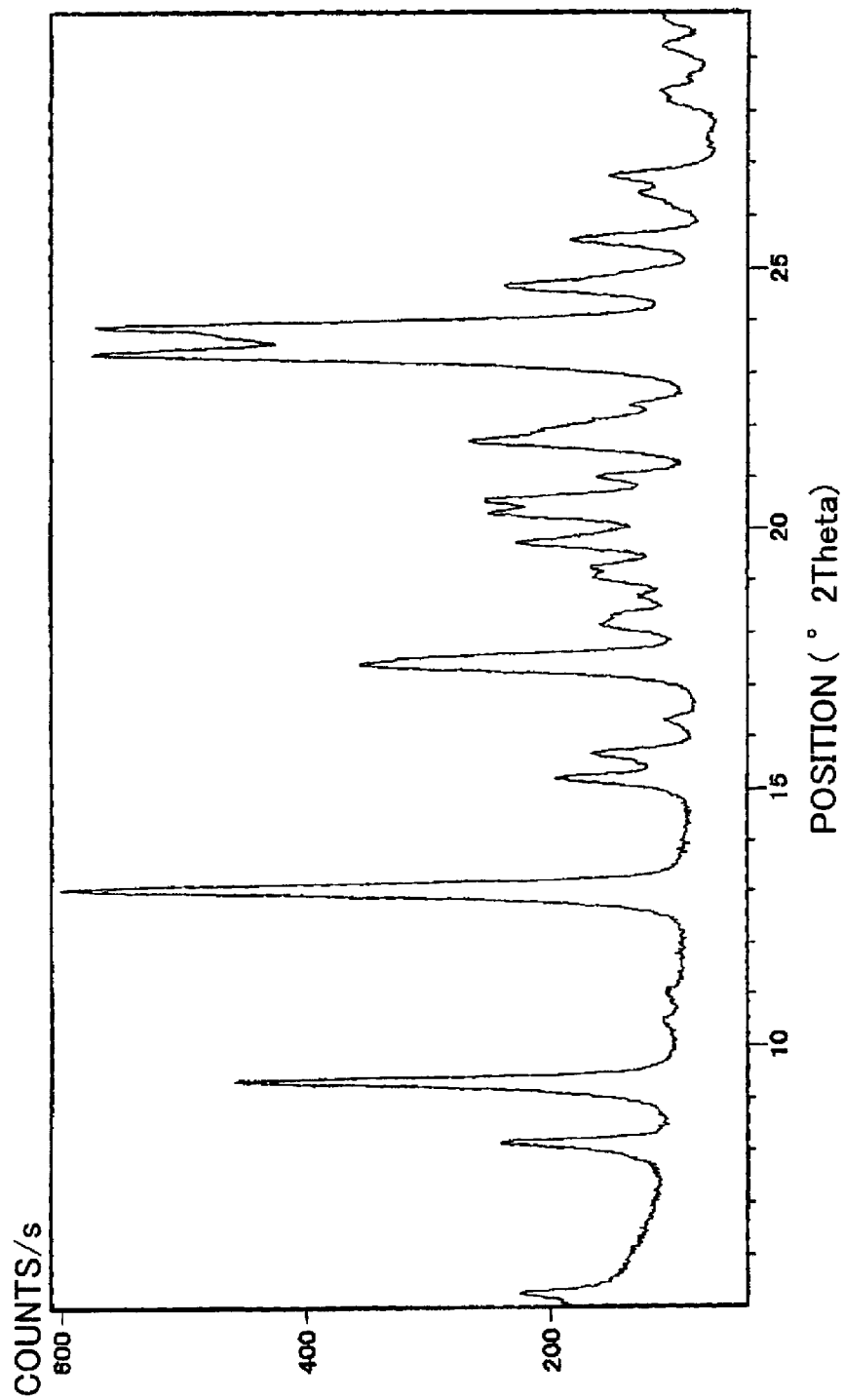
FIG. 48 shows a powder X-ray diffraction pattern of crystal form Ms4 of a methanesulfonate salt of the compound of the formula (I) of the present invention.
Figure 49:
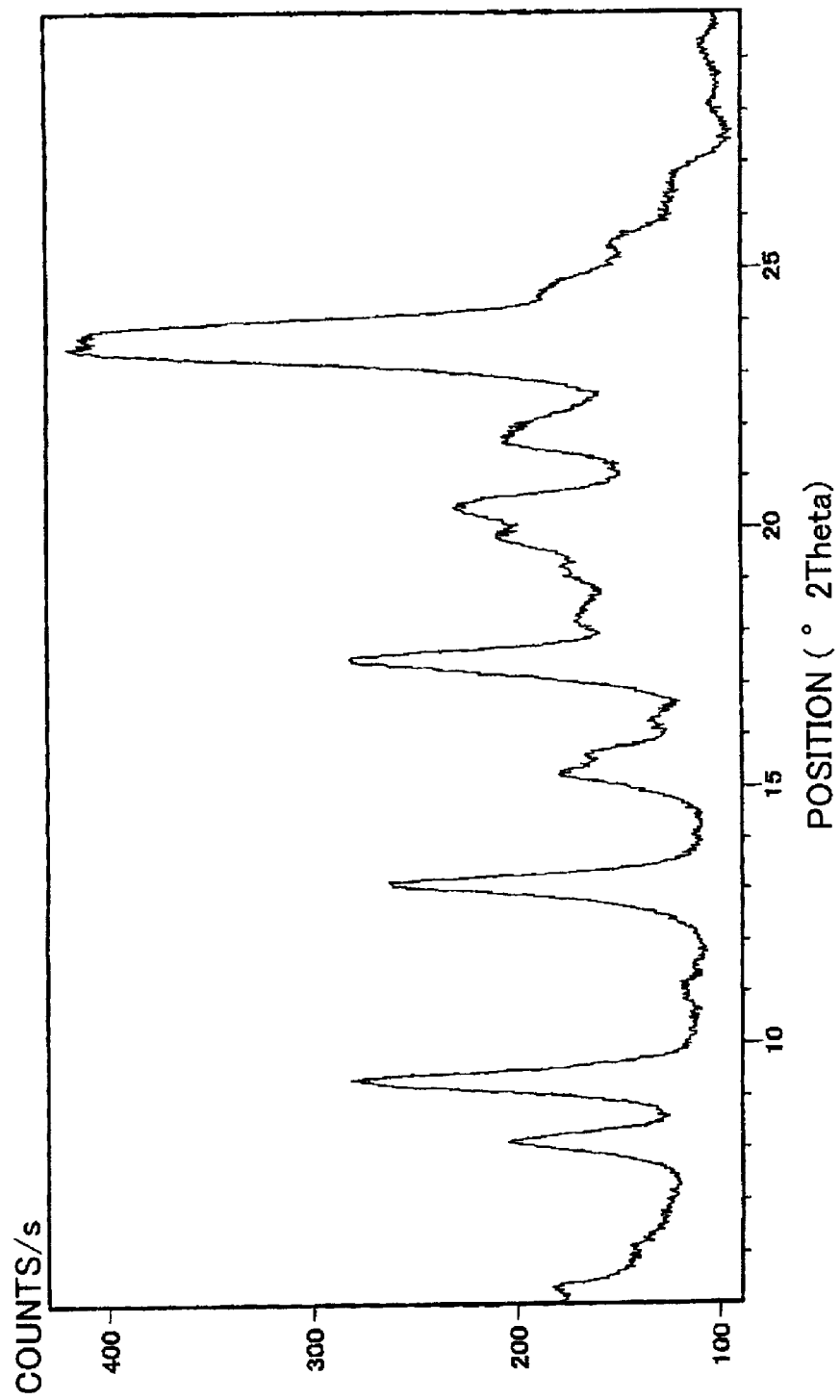
FIG. 49 shows a powder X-ray diffraction pattern of crystal form Ms5 of a methanesulfonate salt of the compound of the formula (I) of the present invention.
Figure 50:
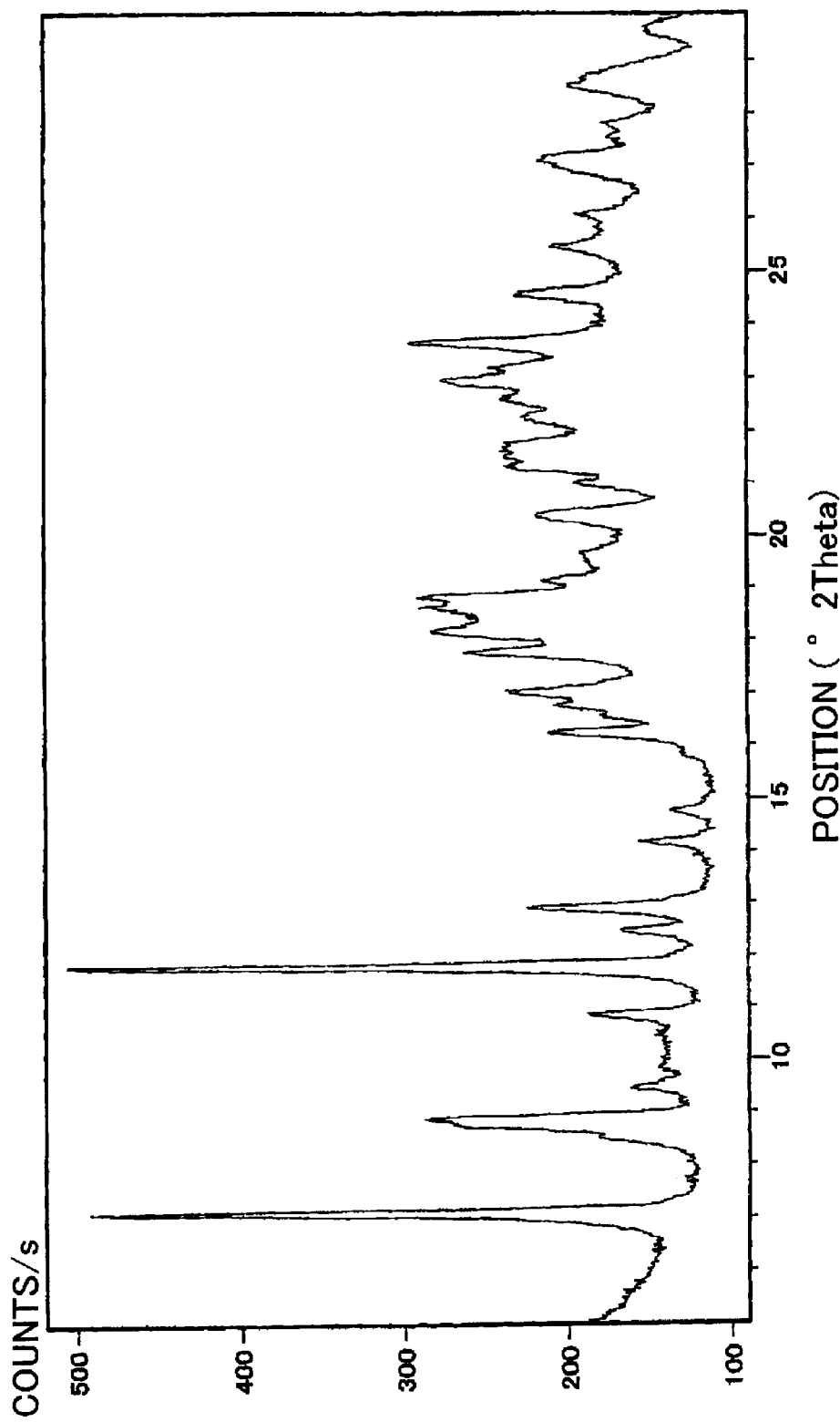
FIG. 50 shows a powder X-ray diffraction pattern of crystal form L-Tar1 of an L-tartrate salt of the compound of the formula (I) of the present invention.
Figure 51:
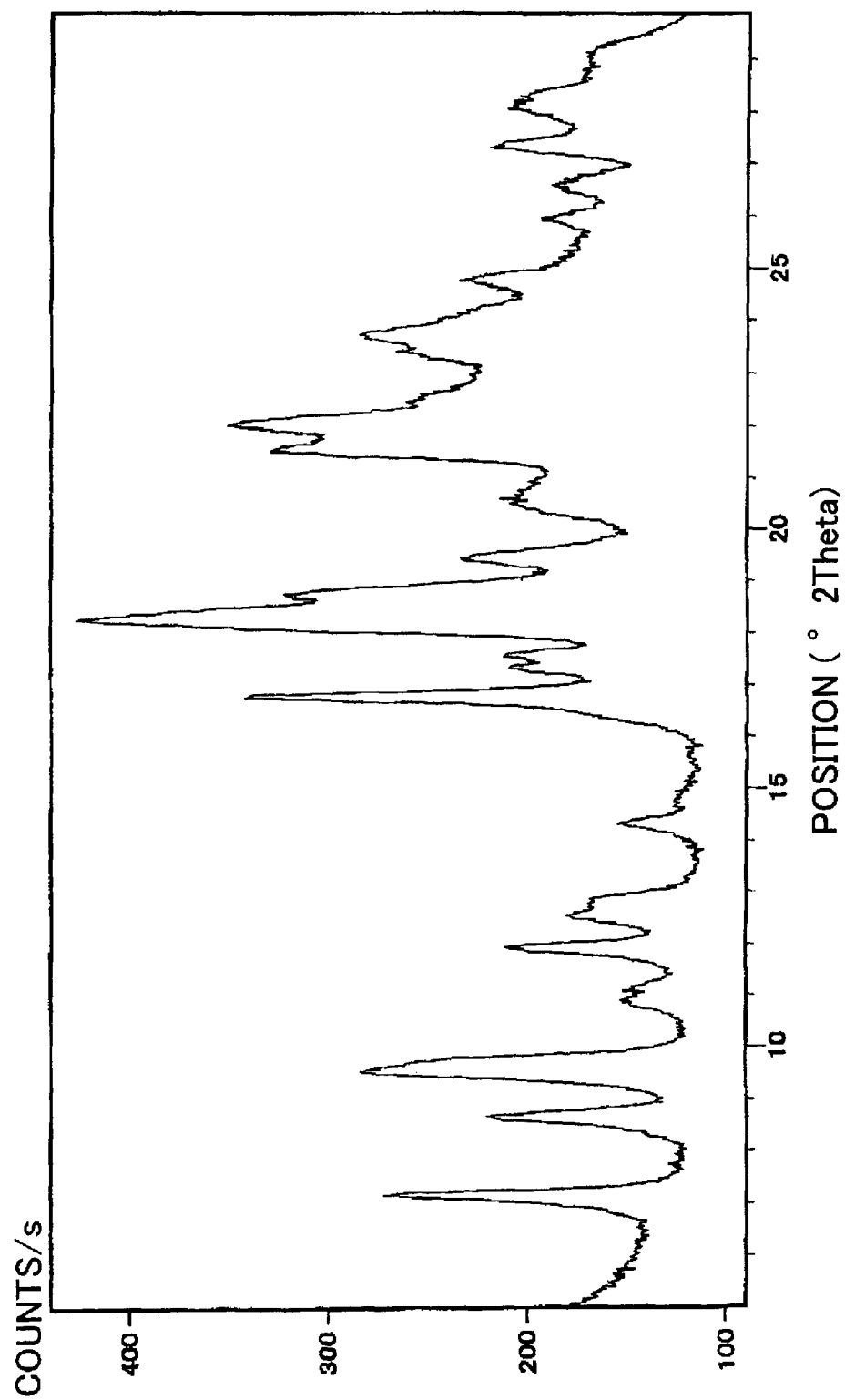
FIG. 51 shows a powder X-ray diffraction pattern of crystal form L-Tar2 of an L-tartrate salt of the compound of the formula (I) of the present invention.
Figure 52:
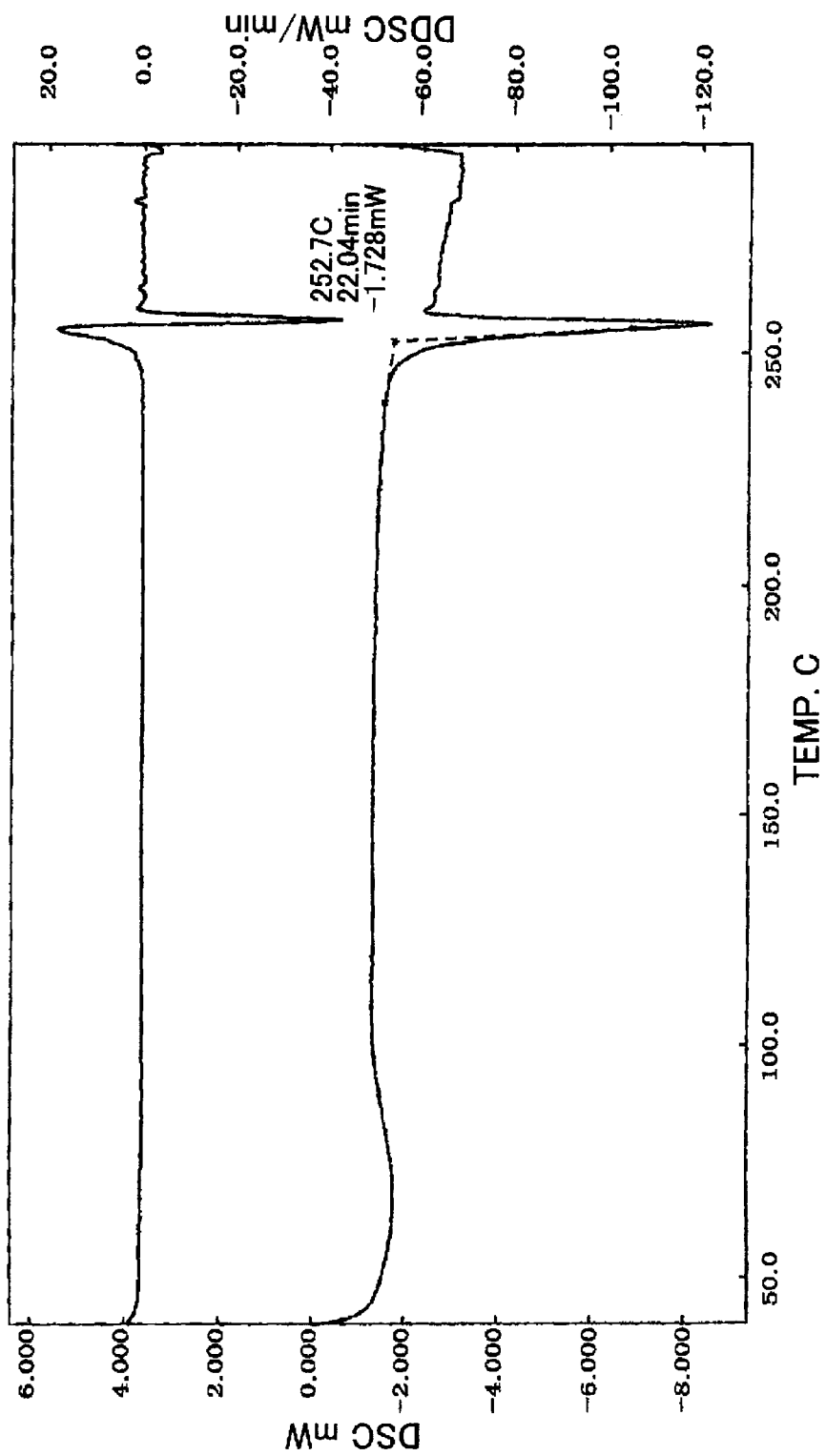
FIG. 52 shows a DSC curve of crystal form Cl6 of a hydrochloride salt of the compound of the formula (I) of the present invention.
Figure 53:
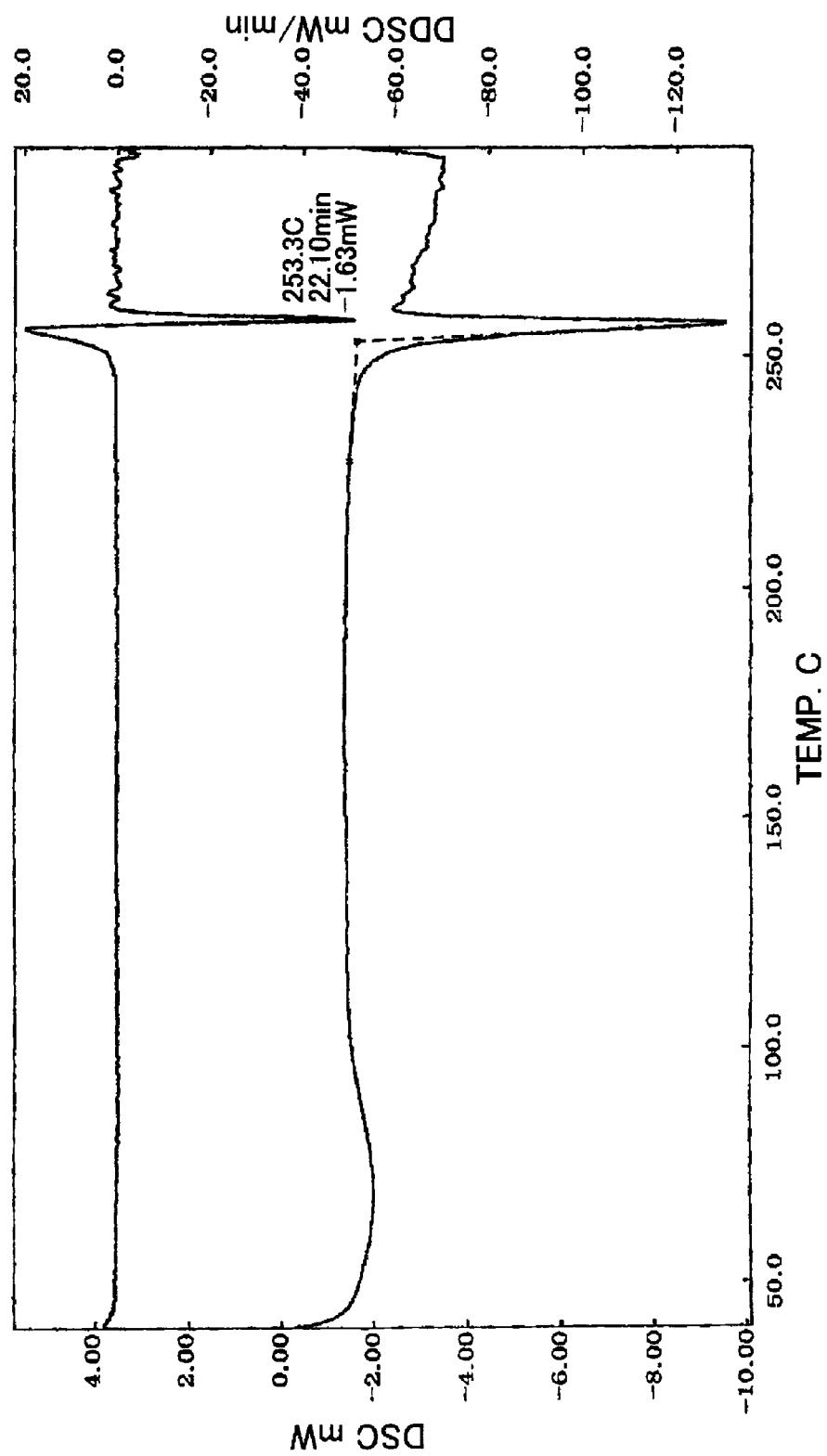
FIG. 53 shows a DSC curve of crystal form Cl7 of a hydrochloride salt of the compound of the formula (I) of the present invention.
Figure 54:
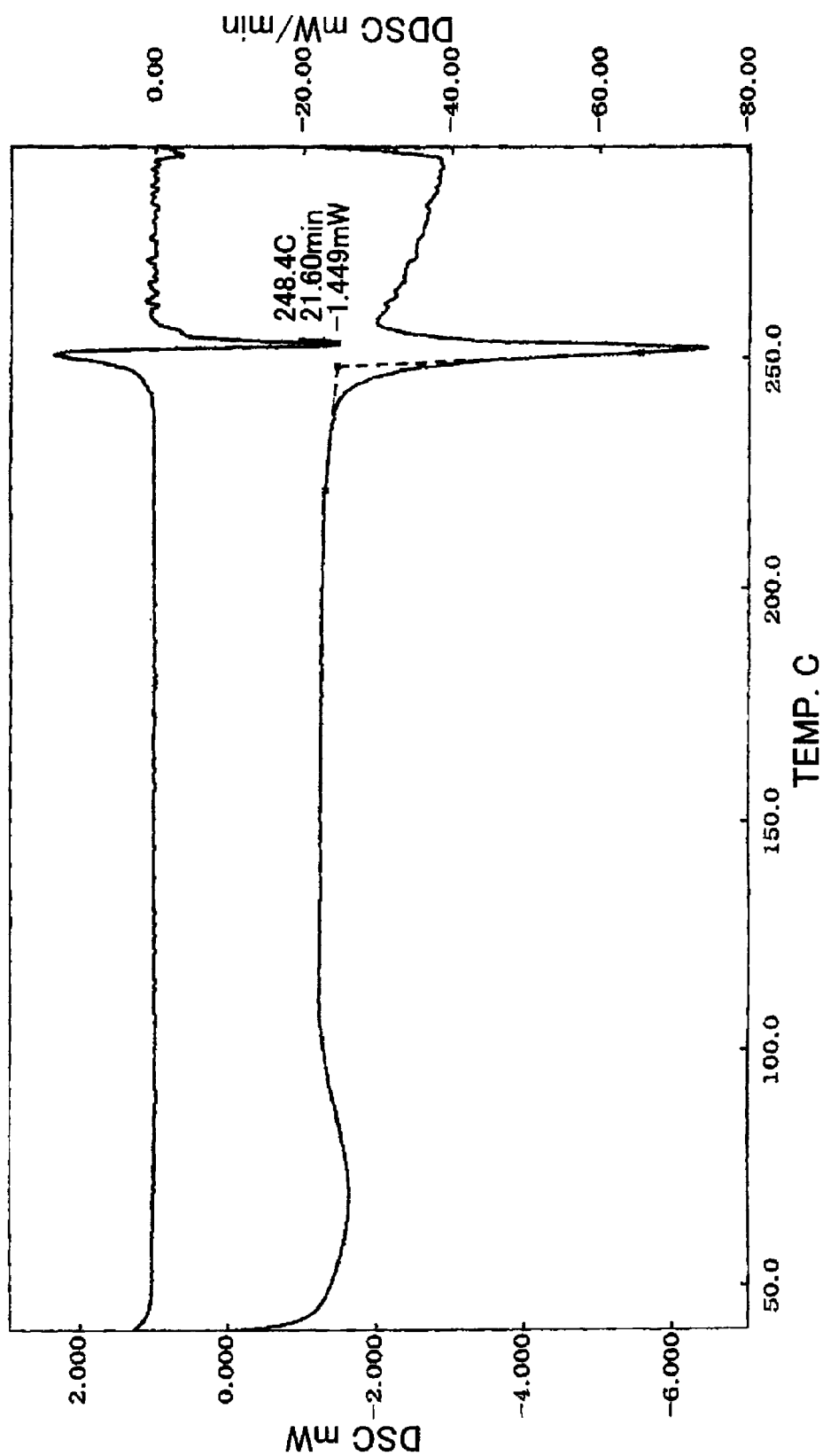
FIG. 54 shows a DSC curve of crystal form Cl8 of a hydrochloride salt of the compound of the formula (I) of the present invention.
Figure 55:
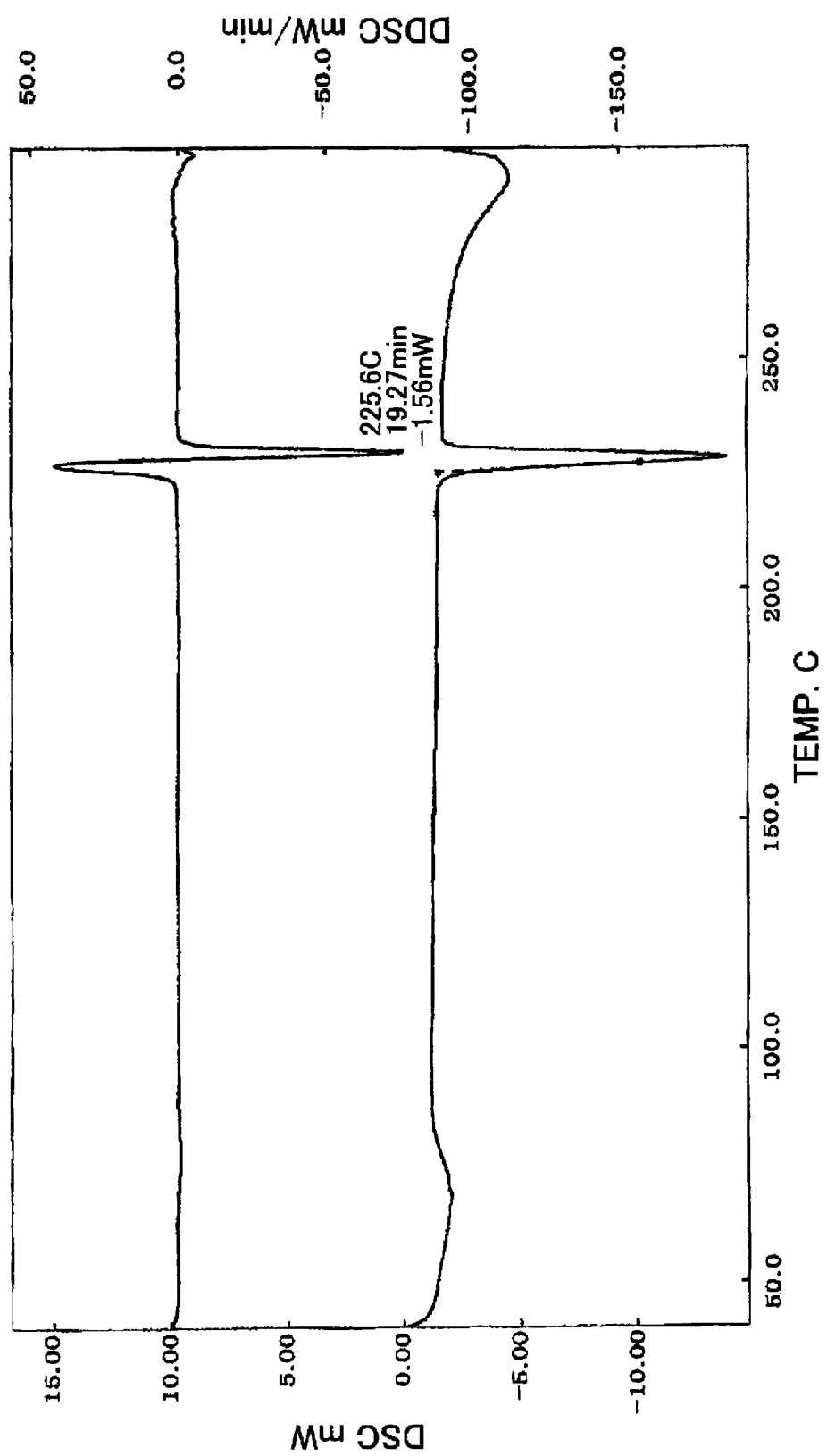
FIG. 55 shows a DSC curve of Crystal form Ms1 of a methanesulfonate salt of the compound of the formula (I) of the present invention.

Reference: An empty aluminum pan
Sampling time: 0.2 sec.
Range: 40 to 300° C.
Heating Time: 10 or 20° C./min The results are shown in FIG. 24 (crystal form N1), FIG. 27 (crystal form N2), FIG. 31 (crystal form N3), FIG. 34 (crystal form N4), FIG. 37 (crystal form N5), FIG. 52 (crystal form Cl6), FIG. 53 (crystal form Cl7), FIG. 54 (crystal form Cl8) and FIG. 55 (crystal form Ms1).

What is claimed is:

1. A crystal of the hydrochloride salt of the compound of formula (I):

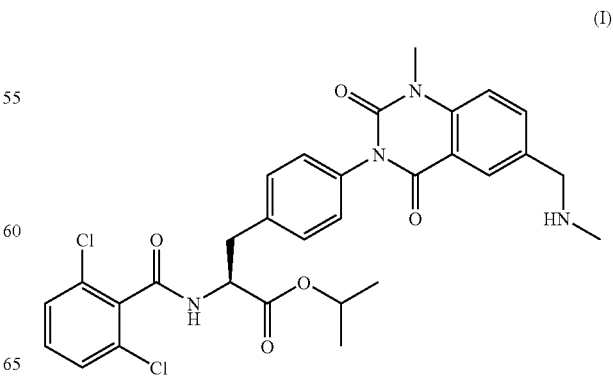

which is either:
- crystal form Cl 1, which has peaks at the diffraction angles (2θ) 2.9°, 7.7°, 11.6°, and 20.3° in its powder X-ray diffraction pattern;
- crystal form Cl 2, which has peaks at the diffraction angles (2θ) 8.5°, 10.5°, 16.0°, 17.0°, and 23.6° in its powder X-ray diffraction pattern;
- crystal form Cl 3, which has peaks at the diffraction angles (2θ) 3.6°, 8.9°, and 12.4° in its powder X-ray diffraction pattern;
- crystal form Cl 4, which has peaks at the diffraction angles (2θ) 4.9° and 17.5° in its powder X-ray diffraction pattern; or
- crystal form Cl 5, which has peaks at the diffraction angles (2θ) 8.2°, 11.2°, 14.3°, and 15.6° in its powder X-ray diffraction pattern.

2. A crystal according to claim 1, which is crystal form Cl 5.

3. A method of making a crystal according to claim 2, which comprises adding hydrogen chloride to a mixture comprising the compound of formula (I) and acetone.

4. A method of making a crystal according to claim 2, which comprises:
- heating the hydrochloride salt of the compound of formula (I) in a solvent comprising acetone and water, to obtain a first heated mixture;
- adding an acetone solvent to said first heated mixture, to obtain a second heated mixture; and
- cooling said second heated mixture.

5. A method of making a crystal according to claim 2, which comprises mixing the hydrochloride salt of the compound of formula (I) and two or more solvents selected from the group consisting of acetone, water, tetrahydrofuran, acetonitrile, methanol, ethanol, propanol and isopropyl acetate to obtain a suspension thereof.

6. A pharmaceutical composition, which comprises a crystal according to claim 1 and a pharmaceutically acceptable carrier.

7. A crystal according to claim 1, which is crystal form Cl 1.

8. A crystal according to claim 1, which is crystal form Cl 2.

9. A crystal according to claim 1, which is crystal form Cl 3.

10. A crystal according to claim 1, which is crystal form Cl 4.

11. A pharmaceutical composition, which comprises a crystal according to claim 2 and a pharmaceutically acceptable carrier.

12. A pharmaceutical composition, which comprises a crystal according to claim 7 and a pharmaceutically acceptable carrier.

13. A pharmaceutical composition, which comprises a crystal according to claim 8 and a pharmaceutically acceptable carrier.

14. A pharmaceutical composition, which comprises a crystal according to claim 9 and a pharmaceutically acceptable carrier.

15. A pharmaceutical composition, which comprises a crystal according to claim 10 and a pharmaceutically acceptable carrier.

* * * * *